US011154428B2

(12) United States Patent
Rosati et al.

(10) Patent No.: US 11,154,428 B2
(45) Date of Patent: Oct. 26, 2021

(54) ABSORBENT ARTICLES WITH INDICIA AND/OR COLOR

(71) Applicant: The Procter & Gamble Company, Cincinnati, OH (US)

(72) Inventors: Rodrigo Rosati, Frankfurt am Main (DE); Aniruddha Chatterjee, Kelkheim (DE); Matthew Steven Ritter, Liberty Township, OH (US); Jill Marlene Orr, Liberty Township, OH (US); John B. Strube, Okeana, OH (US); Adrien Grenier, Frankfurt am Main (DE); James T. Knapmeyer, Cincinnati, OH (US); John Lee Hammons, Hamilton, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 600 days.

(21) Appl. No.: 14/844,047

(22) Filed: Sep. 3, 2015

(65) Prior Publication Data

US 2016/0074259 A1 Mar. 17, 2016

Related U.S. Application Data

(60) Provisional application No. 62/049,516, filed on Sep. 12, 2014, provisional application No. 62/049,521, (Continued)

(51) Int. Cl.
*A61F 13/53* (2006.01)
*A61F 13/551* (2006.01)
(Continued)

(52) U.S. Cl.
CPC .. *A61F 13/15699* (2013.01); *A61F 13/15203* (2013.01); *A61F 13/15707* (2013.01);
(Continued)

(58) Field of Classification Search
CPC .... A61F 13/15699; A61F 13/51; A61F 13/53; A61F 2013/15284
See application file for complete search history.

(56) References Cited

U.S. PATENT DOCUMENTS 4,323,068 A 4/1982 Aziz
4,834,735 A * 5/1989 Alemany .............. A61F 13/533
428/213

(Continued)

FOREIGN PATENT DOCUMENTS

CA 2518857 11/2004
EP 1283028 2/2003
(Continued)

OTHER PUBLICATIONS

International Search Report and Written Opinion, PCT/US2015/048373, dated Nov. 19, 2015.
(Continued)

*Primary Examiner* — Tatyana Zalukaeva
*Assistant Examiner* — Jessica R Arble
(74) *Attorney, Agent, or Firm* — Brian M. Bolam

(57) ABSTRACT

An absorbent article is disclosed, including a three-dimensional material formed of a liquid permeable topsheet and an acquisition material. The acquisition material is positioned beneath the topsheet, and both may be formed of nonwoven material. The three dimensional material may have two surfaces and a plurality of protrusions extending in a z-direction from one of the surfaces, each protrusion having side walls defining an opening in the other of the surfaces. One of the topsheet and the acquisition material may include
(Continued)

fibers spun of polymer resin pigmented with a first color that differs from a second color of fibers of the other of the topsheet and the acquisition material, and the differing colors are visible when viewing a wearer-facing surface of the absorbent article.

2 Claims, 53 Drawing Sheets

Related U.S. Application Data filed on Sep. 12, 2014, provisional application No. 62/049,408, filed on Sep. 12, 2014, provisional application No. 62/049,406, filed on Sep. 12, 2014, provisional application No. 62/049,404, filed on Sep. 12, 2014, provisional application No. 62/049,403, filed on Sep. 12, 2014, provisional application No. 62/049,401, filed on Sep. 12, 2014, provisional application No. 62/049,397, filed on Sep. 12, 2014, provisional application No. 62/049,392, filed on Sep. 12, 2014, provisional application No. 62/210,057, filed on Aug. 26, 2015, provisional application No. 62/210,005, filed on Aug. 26, 2015, provisional application No. 62/210,020, filed on Aug. 26, 2015, provisional application No. 62/210,014, filed on Aug. 26, 2015.

(51) Int. Cl.
*A61F 13/84* (2006.01)
*A61F 13/15* (2006.01)
*A61F 13/511* (2006.01)
*A61F 13/512* (2006.01)
*A61F 13/536* (2006.01)
*A61F 13/537* (2006.01)
*A61F 13/513* (2006.01)
*A61F 13/534* (2006.01)
*A61F 13/45* (2006.01)
*A61F 13/51* (2006.01)
*A61F 13/535* (2006.01)
*A61F 13/538* (2006.01)
*A61F 13/539* (2006.01)
*A61F 13/42* (2006.01)

(52) U.S. Cl.
CPC ........ *A61F 13/15723* (2013.01); *A61F 13/45* (2013.01); *A61F 13/51* (2013.01); *A61F 13/511* (2013.01); *A61F 13/513* (2013.01); *A61F 13/5116* (2013.01); *A61F 13/5121* (2013.01); *A61F 13/51104* (2013.01); *A61F 13/51108* (2013.01); *A61F 13/51394* (2013.01); *A61F 13/53* (2013.01); *A61F 13/534* (2013.01); *A61F 13/535* (2013.01); *A61F 13/536* (2013.01); *A61F 13/537* (2013.01); *A61F 13/551* (2013.01); *A61F 13/55105* (2013.01); *A61F 13/55115* (2013.01); *A61F 13/55145* (2013.01); *A61F 2013/15284* (2013.01); *A61F 2013/15365* (2013.01); *A61F 2013/15463* (2013.01); *A61F 2013/15715* (2013.01); *A61F 2013/421* (2013.01); *A61F 2013/427* (2013.01); *A61F 2013/4568* (2013.01); *A61F 2013/4587* (2013.01); *A61F 2013/51002* (2013.01); *A61F 2013/51007* (2013.01); *A61F 2013/51009* (2013.01); *A61F 2013/51023* (2013.01); *A61F 2013/51026* (2013.01); *A61F 2013/51092* (2013.01); *A61F 2013/51147* (2013.01); *A61F 2013/51355* (2013.01); *A61F 2013/51377* (2013.01); *A61F 2013/5307* (2013.01); *A61F 2013/530007* (2013.01); *A61F 2013/5386* (2013.01); *A61F 2013/5395* (2013.01); *A61F 2013/530131* (2013.01); *A61F 2013/530175* (2013.01); *A61F 2013/53472* (2013.01); *A61F 2013/530481* (2013.01); *A61F 2013/530489* (2013.01); *A61F 2013/530664* (2013.01); *A61F 2013/530715* (2013.01); *A61F 2013/53908* (2013.01); *A61F 2013/8497* (2013.01)

(56) References Cited

U.S. PATENT DOCUMENTS

| | | | |
|---|---|---|---|
| 5,064,492 A * | 11/1991 | Friesch | A61F 13/15577 156/191 |
| 5,518,801 A | 5/1996 | Chappell et al. | |
| 5,599,335 A | 2/1997 | Goldman et al. | |
| 5,628,097 A | 5/1997 | Benson et al. | |
| 5,804,021 A | 9/1998 | Abuto et al. | |
| 5,888,607 A | 3/1999 | Seth et al. | |
| 5,938,650 A | 8/1999 | Baer et al. | |
| 6,136,124 A | 10/2000 | Wagner | |
| 6,274,218 B1 | 8/2001 | Shimizu | |
| 6,344,102 B1 | 2/2002 | Wagner | |
| 6,395,957 B1 | 5/2002 | Chen et al. | |
| 6,440,564 B1 | 8/2002 | Mclain et al. | |
| 6,610,904 B1 | 8/2003 | Thomas | |
| 6,641,902 B1 | 11/2003 | Kobayashi et al. | |
| 6,685,686 B2 | 2/2004 | Hermansson et al. | |
| 6,700,036 B2 | 3/2004 | Thomas et al. | |
| 6,733,626 B2 | 5/2004 | Ruthven et al. | |
| 6,739,024 B1 | 5/2004 | Wagner | |
| 6,818,802 B2 | 11/2004 | Takai et al. | |
| 6,887,349 B2 | 5/2005 | Ruthven et al. | |
| 7,037,406 B2 | 5/2006 | Kershaw et al. | |
| 7,060,344 B2 | 6/2006 | Pourdeyhimi et al. | |
| 7,172,801 B2 | 2/2007 | Hoying et al. | |
| 7,182,838 B2 | 2/2007 | Ruthven et al. | |
| 7,267,860 B2 | 9/2007 | Toyoshima et al. | |
| 7,294,231 B2 | 11/2007 | Kershaw et al. | |
| 7,297,226 B2 | 11/2007 | Schulz | |
| 7,326,322 B2 | 2/2008 | Ruthven et al. | |
| 7,410,683 B2 | 8/2008 | Gray et al. | |
| 7,468,114 B2 | 12/2008 | Sato et al. | |
| 7,531,062 B2 | 5/2009 | Kershaw et al. | |
| 7,553,532 B2 | 6/2009 | Gray et al. | |
| 7,648,752 B2 | 1/2010 | Gray et al. | |
| 7,678,034 B2 | 3/2010 | Wilhelm | |
| 7,682,686 B2 | 3/2010 | Gray et al. | |
| 7,687,679 B2 | 3/2010 | Mishima | |
| 7,799,176 B2 | 9/2010 | Wilhelm | |
| 7,842,849 B2 | 11/2010 | Datta | |
| 7,857,941 B2 | 12/2010 | Ruthven et al. | |
| 7,951,127 B2 | 5/2011 | Sanabria et al. | |
| 8,142,617 B2 | 3/2012 | Ruthven et al. | |
| D662,326 S | 6/2012 | Shanbhag et al. | |
| 8,231,377 B2 | 7/2012 | Wittner et al. | |
| 8,241,543 B2 | 8/2012 | O'Donnell et al. | |
| 8,287,694 B2 | 10/2012 | Schulz | |
| 8,304,600 B2 | 11/2012 | Noda et al. | |
| 8,313,473 B2 | 11/2012 | Nada | |
| D672,152 S | 12/2012 | Shanbhag et al. | |
| 8,393,374 B2 | 3/2013 | Sato et al. | |
| 8,535,481 B2 | 9/2013 | Schulz | |
| 8,574,209 B2 | 11/2013 | Nishitani et al. | |
| 8,585,958 B2 | 11/2013 | Gray et al. | |
| 8,617,449 B2 | 12/2013 | Baker et al. | |
| 2002/0004654 A1 | 1/2002 | Daniels et al. | |
| 2003/0149410 A1 * | 8/2003 | Kudo | A61F 13/15203 604/367 |
| 2003/0195487 A1 | 10/2003 | Thomas | |
| 2003/0211802 A1 | 11/2003 | Keck et al. | |
| 2004/0002688 A1 | 1/2004 | Thomas et al. | |
| 2004/0229008 A1 | 11/2004 | Hoying | |

(56) References Cited

U.S. PATENT DOCUMENTS

| | | | |
|---|---|---|---|
| 2004/0265534 A1 | 12/2004 | Curro et al. | |
| 2005/0008825 A1 | 1/2005 | Casey et al. | |
| 2005/0170726 A1* | 8/2005 | Brunson | A41D 13/11 |
| | | | 442/327 |
| 2006/0111684 A1 | 5/2006 | Berba et al. | |
| 2006/0194027 A1 | 8/2006 | Pourdeyhimi et al. | |
| 2006/0286343 A1 | 12/2006 | Gray et al. | |
| 2007/0212966 A1 | 9/2007 | Wittner et al. | |
| 2008/0221538 A1 | 9/2008 | Zhao et al. | |
| 2008/0227356 A1 | 9/2008 | Poruthoor et al. | |
| 2009/0030390 A1 | 1/2009 | Hammons et al. | |
| 2010/0028621 A1 | 2/2010 | Byrne et al. | |
| 2010/0036338 A1 | 2/2010 | Hammons et al. | |
| 2010/0247844 A1 | 9/2010 | Curro et al. | |
| 2010/0249740 A1 | 9/2010 | Miyamoto et al. | |
| 2010/0297377 A1 | 11/2010 | Buscher et al. | |
| 2010/0310810 A1 | 12/2010 | Bond et al. | |
| 2011/0073513 A1 | 3/2011 | Weisman et al. | |
| 2011/0094669 A1* | 4/2011 | Oetjen | A61F 13/51394 |
| | | | 156/250 |
| 2011/0125120 A1 | 5/2011 | Nishitani et al. | |
| 2011/0130735 A1* | 6/2011 | Weismantel | A61F 13/15203 |
| | | | 604/372 |
| 2011/0152813 A1* | 6/2011 | Ellingson | A61F 13/532 |
| | | | 604/374 |
| 2011/0260371 A1 | 10/2011 | Arora et al. | |
| 2012/0064298 A1 | 3/2012 | Curro et al. | |
| 2012/0136329 A1 | 5/2012 | Carney | |
| 2012/0226249 A1* | 9/2012 | Prodoehl | A61F 13/15 |
| | | | 604/367 |
| 2012/0234475 A1 | 9/2012 | Paldey | |
| 2012/0238984 A1 | 9/2012 | Paldey | |
| 2012/0316529 A1* | 12/2012 | Kreuzer | A61F 13/533 |
| | | | 604/366 |
| 2013/0165883 A1 | 6/2013 | Kimura et al. | |
| 2013/0309439 A1 | 11/2013 | Close et al. | |
| 2014/0039434 A1 | 2/2014 | Xu et al. | |
| 2014/0052088 A1 | 2/2014 | Weisman et al. | |
| 2014/0054827 A1 | 2/2014 | Mullane et al. | |
| 2014/0121621 A1 | 5/2014 | Biggs et al. | |
| 2014/0121623 A1* | 5/2014 | Kirby | A61F 13/51108 |
| | | | 604/383 |
| 2014/0121624 A1 | 5/2014 | Biggs et al. | |
| 2014/0121625 A1 | 5/2014 | Biggs et al. | |
| 2014/0121626 A1 | 5/2014 | Butler et al. | |
| 2014/0163500 A1 | 6/2014 | Roe et al. | |
| 2014/0163501 A1 | 6/2014 | Ehrnsperger et al. | |
| 2014/0170367 A1 | 6/2014 | Turner et al. | |
| 2014/0276517 A1 | 9/2014 | Chester et al. | |
| 2014/0367290 A1 | 12/2014 | Nomoto et al. | |
| 2015/0073366 A1 | 3/2015 | Ehrnsperger et al. | |

FOREIGN PATENT DOCUMENTS

| | | |
|---|---|---|
| EP | 861646 | 5/2003 |
| EP | 1208828 | 7/2005 |
| EP | 1184075 | 1/2007 |
| EP | 1842513 | 10/2007 |
| EP | 1787611 | 9/2011 |
| EP | 2554730 | 2/2013 |
| EP | 1982013 | 6/2013 |
| EP | 1774940 | 9/2013 |
| EP | 2437708 | 9/2013 |
| EP | 2277485 | 5/2014 |
| JP | 02055058 | 5/1996 |
| JP | 3124190 | 1/2001 |
| JP | 3868880 | 1/2007 |
| JP | 3880502 | 2/2007 |
| JP | 4184253 | 11/2008 |
| JP | 4282428 | 6/2009 |
| JP | 2009172354 | 8/2009 |
| JP | 2011200446 | 10/2011 |
| JP | 2012010884 | 1/2012 |
| JP | 4901425 | 3/2012 |
| JP | 4931580 B2 | 5/2012 |
| JP | 4974524 | 7/2012 |
| JP | 5074174 | 11/2012 |
| JP | 5099752 B2 | 12/2012 |
| JP | 5103100 | 12/2012 |
| JP | 5148182 | 2/2013 |
| JP | 2013074978 | 4/2013 |
| JP | 2013126455 | 6/2013 |
| JP | 5268416 | 8/2013 |
| JP | 2013169388 | 9/2013 |
| JP | 5319367 | 10/2013 |
| WO | WO 9301781 | 2/1993 |
| WO | WO 9827904 | 7/1998 |
| WO | WO 200029199 | 5/2000 |
| WO | WO 2000/38604 | 7/2000 |
| WO | WO 200174281 | 10/2001 |
| WO | WO 200224133 | 3/2002 |
| WO | WO 200429349 | 4/2004 |
| WO | WO 2004098869 | 11/2004 |
| WO | WO 2006007149 | 1/2006 |
| WO | WO 2007001270 | 1/2007 |
| WO | WO 2007116944 | 10/2007 |
| WO | WO 2008146594 | 12/2008 |
| WO | WO 2009139255 | 11/2009 |
| WO | WO 201074205 | 7/2010 |
| WO | WO2010118272 | 10/2010 |
| WO | WO 2011142272 | 11/2011 |
| WO | WO 2012176656 | 12/2012 |
| WO | WO 201347890 | 4/2013 |
| WO | WO 201377074 | 5/2013 |
| WO | WO 2013399463 | 7/2013 |
| WO | WO 2013147222 | 10/2013 |
| WO | WO 2013175360 | 11/2013 |
| WO | WO 2014084066 | 6/2014 |
| WO | WO 201545842 | 4/2015 |

OTHER PUBLICATIONS

All Office Actions for U.S. Appl. No. 14/844,018.
All Office Actions for U.S. Appl. No. 14/844,026.
All Office Actions for U.S. Appl. No. 14/844,033.
All Office Actions for U.S. Appl. No. 14/844,037.
All Office Actions for U.S. Appl. No. 14/844,043.
All Office Actions for U.S. Appl. No. 14/844,292.
All Office Actions for U.S. Appl. No. 14/844,343.
All Office Actions for U.S. Appl. No. 14/844,358.
All Office Actions for U.S. Appl. No. 14/844,374.
All Office Actions for U.S. Appl. No. 14/844,385.
All Office Actions for U.S. Appl. No. 14/844,402.
All Office Actions for U.S. Appl. No. 14/844,411.
All Office Actions for U.S. Appl. No. 14/844,256.
All Office Actions for U.S. Appl. No. 14/844,269.
All Office Actions for U.S. Appl. No. 14/844,459.
All Office Actions for U.S. Appl. No. 14/844,499.
All Office Actions for U.S. Appl. No. 14/844,526.
All Office Actions for U.S. Appl. No. 14/844,457.
All Office Actions for U.S. Appl. No. 14/844,507.
All Office Actions for U.S. Appl. No. 14/844,523.
All Office Actions for U.S. Appl. No. 14/844,543.
All Office Actions for U.S. Appl. No. 14/844,582.
All Office Actions for U.S. Appl. No. 14/844,591.
All Office Actions for U.S. Appl. No. 14/844,603.
All Office Actions for U.S. Appl. No. 14/844,613.

* cited by examiner

ABSORBENT ARTICLES WITH INDICIA AND/OR COLOR

RELATED APPLICATIONS

This application claims priority under 35 U.S.C. § 119(e) to U.S. Provisional Patent Application Ser. Nos. 62/049,516, 62/049,521, 62/049,408, 62/049,406, 62/049,404, 62/049,403, 62/049,401, 62/049,397, and 62/049,392, all of which were filed on Sep. 12, 2014, and to U.S. Provisional Patent Application Ser. Nos. 62/210,005, 62/210,014, 62/210,020, and 62/210,057, all of which were filed on Aug. 26, 2015. The entire disclosures of all of the above-referenced U.S. Provisional Patent Applications are fully incorporated herein by reference.

FIELD

The present disclosure relates to absorbent articles, and more particularly relates to absorbent articles with channel configurations in combination with three-dimensional materials. These absorbent articles may have indicia and/or color in various layers. The indicia or color may be used in the various layers with or without the channels configurations.

BACKGROUND

Absorbent articles are used to absorb and contain bodily exudates (e.g., urine, menses, BM). The absorbent articles are often configured as diapers, pants, adult incontinence articles, or sanitary napkins, for example. Consumers in some markets desire three-dimensional materials on wearer-facing surfaces of the absorbent articles, such as topsheets. These three-dimensional materials create depth in absorbent articles and thereby provide consumers with the impression of better absorbency and reduced skin exposure to bodily exudates. The three-dimensional materials also provide improved softness or the impression of improved softness relative to planar materials. The impressions of better absorbency, reduced bodily exudate exposure to skin, and softness, however, are not the only attributes that consumers desire. Consumers also desire the impression that the absorbent article will not only lock away bodily exudates adequately, reduce skin exposure thereto, and have improved softness, but also that the absorbent article will distribute the bodily exudates evenly about the length of the absorbent article to at least inhibit, for example, crotch sagging. Further, consumers desire absorbent articles that are visually appealing and that enhance the impression that the absorbent articles will lock away bodily exudates, reduce skin exposure thereto, and provide the impression of depth and improved softness. What is needed are absorbent articles that provide the impression of depth, improved softness, and reduced skin exposure to bodily exudates, but that also provide the impression of uniform fluid distribution about the length of the absorbent articles. Further, what is needed are absorbent articles with indicia and/or color that provide consumer desired absorbent articles that are aesthetically pleasing and give the desired impressions discussed above.

SUMMARY

The absorbent articles of the present disclosure solve the problems associated with related art absorbent articles by providing not only the impressions of depth, improved softness, and reduced exposure to bodily exudates, but also by providing the impression of uniform fluid distribution about the length of the absorbent articles. The absorbent articles of the present disclosure provide all of these benefits by providing a three-dimensional material in combination with channels in various layers intermediate wearer and garment facing surfaces of the absorbent articles. For example, the channels may be present in an absorbent core and/or in one or more layers of a material positioned intermediate an absorbent core and a topsheet. In some instances, the three-dimensional material may create the impression of channels using one or more designs or one or more elongate designs that are visible from a wearer-facing surface of the absorbent articles. The one or more designs or elongate designs may be positioned so that they at least partially overlap with, fully overlap with, or are free from overlap with (all in the Z-direction) other channels in the absorbent articles. The one or more designs or elongate designs may be formed in the three-dimensional material through the use of non-three dimensional areas, different three dimensional areas compared to a remainder of a three-dimensional material, or may be formed in planar topsheets or acquisition materials using embossing, printing, and/or graphics, for example.

The impressions of depth, improved softness, absorbency, and reduced exposure to bodily exudates may also be enhanced in the absorbent articles by providing indicia and/or color on various layers of the absorbent articles, or portions thereof. The indicia and/or color may be used in combination with three dimensional materials and/or channels in various layer of the present disclosure to achieve all of the consumer desired attributes of absorbent articles.

In addition to providing the benefits specified above, consumers desire their absorbent articles to be packaged in conveniently sized packages that still have an adequate amount of absorbent articles. The packages should be compression packed so that a package of the absorbent articles may be conveniently stored. Further, there are distribution cost benefits to compression packaging the absorbent articles, which cost savings is ultimately passed along to consumers.

In a form, the present disclosure is directed, in part, to an absorbent article comprising a liquid permeable nonwoven material comprising a first surface and a second surface. The nonwoven material comprises a plurality of fibers. The nonwoven material comprises a generally planar first region and a plurality of discrete integral second regions that comprise deformations forming protrusions extending outward from the first surface of the nonwoven material and openings in the second surface of the nonwoven material. The protrusions are formed from the fibers. At least some of the protrusions comprise a base proximate to the first surface of the nonwoven material, an opposed distal end extending outward in the Z-direction from the base, side walls between the base and the distal end of the protrusion, and a cap comprising at least a portion of the side walls and the distal end of the protrusion. The side walls have interior surfaces. Multiple fibers extend from the base of the protrusion to the distal end of the protrusion, and contribute to form a portion of the sides and cap of the protrusion. The fibers at least substantially surround the sides of the protrusion. The absorbent article comprises a liquid impermeable material and an absorbent core positioned at least partially intermediate the nonwoven material and the liquid impermeable material. The absorbent core comprises an absorbent material having one or more channels defined therein. The absorbent article comprises a material positioned at least partially intermediate the nonwoven material and the absorbent core. One or more channels are defined in the material.

In a form, the present disclosure is directed, in part, to an absorbent article comprising a liquid permeable nonwoven material comprising a first surface and a second surface. The nonwoven material comprises a plurality of fibers. The nonwoven material comprises a generally planar first region and a plurality of discrete integral second regions that comprise deformations forming protrusions extending outward from the first surface of the nonwoven material and openings in the second surface of the nonwoven material. The protrusions are formed from the fibers. At least some of the protrusions comprise a base proximate to the first surface of the nonwoven material, an opposed distal end extending outward in the Z-direction from the base, side walls between the base and the distal end of the protrusion, and a cap comprising at least a portion of the side walls and the distal end of the protrusion. The side walls have interior surfaces. Multiple fibers extend from the base of the protrusion to the distal end of the protrusion, and contribute to form a portion of the sides and cap of the protrusion. The fibers at least substantially surround the sides of the protrusion. The absorbent article comprises a liquid impermeable material and an absorbent core positioned at least partially intermediate the nonwoven material and the liquid impermeable material. The absorbent core comprises an absorbent material. A first channel is defined in the absorbent material. The absorbent article comprises a material positioned at least partially intermediate the nonwoven material and the absorbent core. A second channel is defined in the material. The absorbent article comprises an indicia visible from a wearer-facing surface on the nonwoven material or another layer intermediate the nonwoven material and the absorbent core.

In a form, the present disclosure is directed, in part, to an absorbent article comprising a liquid permeable nonwoven material comprising a first surface and a second surface. The nonwoven material comprises a plurality of fibers. The nonwoven material comprises a generally planar first region and a plurality of discrete integral second regions that comprise deformations forming protrusions extending outward from the first surface of the nonwoven material and openings in the second surface of the nonwoven material. The protrusions are formed from the fibers. At least some of the protrusions comprise a base proximate to the first surface of the nonwoven material, an opposed distal end extending outward in the Z-direction from the base, side walls between the base and the distal end of the protrusion, and a cap comprising at least a portion of the side walls and the distal end of the protrusion. The side walls have interior surfaces. Multiple fibers extend from the base of the protrusion to the distal end of the protrusion, and contribute to form a portion of the sides and cap of the protrusion. The fibers at least substantially surround the sides of the protrusion. The nonwoven material comprises an elongate visible design. The absorbent article comprises a liquid impermeable material and an absorbent core positioned intermediate the nonwoven material and the liquid impermeable material. The absorbent core comprises an absorbent material. A first channel is defined in the absorbent material. The absorbent article comprises a material positioned at least partially intermediate the nonwoven material and the absorbent core. A second channel is defined in the material. The elongate visible design, the first channel, and the second channel all at least partially overlap each other in a Z-direction.

In a form, the present disclosure is directed, in part, to a package comprising a plurality of absorbent articles. At least a majority of the absorbent articles comprise a liquid permeable nonwoven material comprising a first surface and a second surface. The nonwoven material comprises a plurality of fibers. The nonwoven material comprises a generally planar first region and a plurality of discrete integral second regions that comprise deformations forming protrusions extending outward from the first surface of the nonwoven material and openings in the second surface of the nonwoven material. The protrusions are formed from the fibers. At least some of the protrusions comprise a base proximate to the first surface of the nonwoven material, an opposed distal end extending outward in the Z-direction from the base, side walls between the base and the distal end of the protrusion, and a cap comprising at least a portion of the side walls and the distal end of the protrusion. The side walls have interior surfaces. Multiple fibers extend from the base of the protrusion to the distal end of the protrusion, and contribute to form a portion of the sides and cap of the protrusion. The fibers at least substantially surround the sides of the protrusion. The absorbent article comprises a liquid impermeable material and an absorbent core positioned intermediate the nonwoven material and the liquid impermeable material. The absorbent core comprises an absorbent material. A first channel is defined in the absorbent material. The absorbent article comprises a material positioned at least partially intermediate the nonwoven material and the absorbent core. A second channel is defined in the material. The first channel at least partially overlaps the second channel in a Z-direction. The package has an in-bag stack height in the range of about 70 mm to about 100 mm, in accordance with the In-Bag Stack Height Test herein.

In a form, the present disclosure is directed, in part, to an absorbent article comprising a liquid permeable topsheet and an acquisition material. The liquid permeable topsheet or the acquisition material forms a three-dimensional material comprising a first, a second surface, a generally planar first region, and a plurality of discrete integral second regions that comprise deformations forming protrusions extending outwardly from the second surface of the three-dimensional material and openings in the first surface of the three-dimensional material. At least some protrusions each comprise a base proximate to the first surface, an opposed distal end extending outwardly in a Z-direction from the base, side walls between the base and the distal end of the protrusion, and a cap comprising at least a portion of the side walls and the distal end of the protrusion. The side walls have interior surfaces. The interior surfaces of the side walls define a base opening at the base of the protrusion. The cap has a portion with a maximum interior width. The base opening has a width measured in the same direction as the maximum interior width. The maximum interior width of the cap of the protrusion is greater than the width of the base opening. The absorbent article comprises a liquid impermeable backsheet, an absorbent core positioned at least partially intermediate the three-dimensional material and the liquid impermeable backsheet. The absorbent core comprises an absorbent material at least partially surrounded by a core bag. The absorbent article comprises one or more indicias on any of the topsheet, the acquisition material, the core bag, or an additional layer positioned at least partially intermediate the topsheet and the core bag. The indicia has a different color than the topsheet, the acquisition material, the core bag, or the additional layer that the indicia is on. The indicia is visible when viewing a wearer-facing surface of the absorbent article.

In a form, the present disclosure is directed, in part, to an absorbent article comprising a liquid permeable topsheet and an acquisition material. The liquid permeable topsheet or the acquisition material forms a three-dimensional material comprising a first surface, a second surface, a generally planar first region, and a plurality of discrete integral second regions that comprise deformations forming bulbous protrusions extending outwardly from the second surface of the three-dimensional material and openings in the first surface of the three-dimensional material. The absorbent article comprises a liquid impermeable backsheet and an absorbent core positioned at least partially intermediate the three-dimensional material and the liquid impermeable backsheet. The absorbent core comprises an absorbent material at least partially surrounded by a nonwoven core bag. The absorbent article comprises one or more indicias on any of the topsheet, the acquisition material, the core bag, or an additional layer positioned at least partially intermediate the topsheet and the core bag. The indicia has a different color than the topsheet, the acquisition material, the core bag, or the additional layer that the indicia is on. The indicia is visible when viewing a wearer-facing surface of the absorbent article.

In a form, the present disclosure is directed, in part, to an absorbent article comprising a liquid permeable topsheet and an acquisition material. The liquid permeable topsheet or the acquisition material forms a three-dimensional material comprising a first, a second surface, a generally planar first region and a plurality of discrete integral second regions that comprise deformations forming protrusions extending outwardly from the second surface of the three-dimensional material and openings in the first surface of the three-dimensional material. At least some of the protrusions each comprise a base proximate to the first surface, an opposed distal end extending outwardly in a Z-direction from the base, side walls between the base and the distal end of the protrusion, and a cap comprising at least a portion of the side walls and the distal end of the protrusion. The side walls have interior surfaces. The interior surfaces of the side walls define a base opening at the base of the protrusion. The cap has a portion with a maximum interior width. The base opening has a width measured in the same direction as the maximum interior width. The maximum interior width of the cap of the protrusion is greater than the width of the base opening. The absorbent article comprises a liquid impermeable backsheet, an absorbent core positioned at least partially intermediate the three-dimensional material and the liquid impermeable backsheet. The absorbent core comprises an absorbent material at least partially surrounded by a core bag. One of a portion of the topsheet, a portion of the acquisition material, a portion of the core bag, or a portion of an additional layer positioned at least partially intermediate the topsheet and the core bag is a different color than a different one of the portion of the topsheet, the portion of the acquisition material, the portion of the core bag, or the portion of the additional layer.

In a form, the present disclosure is directed, in part to an absorbent article comprising a liquid permeable topsheet and an acquisition material. The liquid permeable topsheet or the acquisition material forms a three-dimensional material comprising a first surface, a second surface, a generally planar first region, and a plurality of discrete integral second regions that comprise deformations forming bulbous protrusions extending outwardly from the second surface and openings in the first surface. The absorbent article comprises a liquid impermeable backsheet and an absorbent core positioned at least partially intermediate the three-dimensional material and the liquid impermeable backsheet. The absorbent core comprises an absorbent material at least partially surrounded by a nonwoven core bag. One of a portion of the topsheet, a portion of the acquisition material, a portion of the core bag, or a portion of an additional layer positioned at least partially intermediate the topsheet and the core bag is a different color than a different one of the portion of the topsheet, the portion of the acquisition material, the portion of the core bag, and the portion of the additional layer.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein.

DETAILED DESCRIPTION

Figure 1:
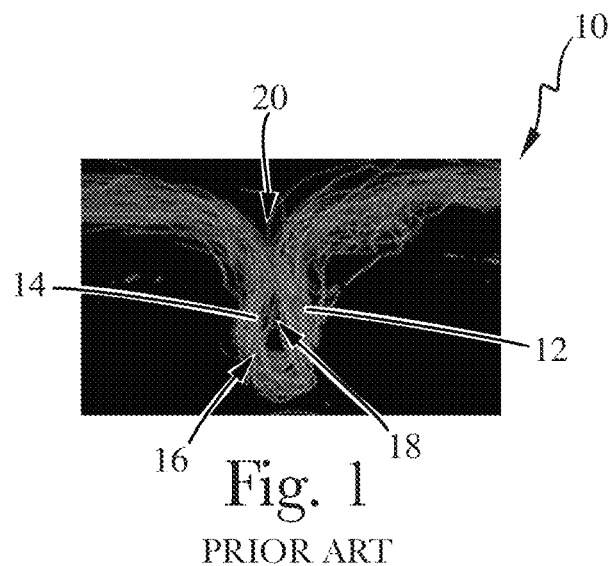
FIG. 1 is a photomicrograph showing the end view of a prior art tuft.

Various non-limiting form of the present disclosure will now be described to provide an overall understanding of the principles of the structure, function, manufacture, and use of the absorbent articles with indicia and/or color disclosed herein. One or more examples of these non-limiting forms are illustrated in the accompanying drawings. Those of ordinary skill in the art will understand that the absorbent articles with indicia and/or color described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Definitions

The term "absorbent article", as used herein, includes disposable articles such as sanitary napkins, panty liners, tampons, interlabial devices, wound dressings, diapers (taped or pants), adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet. The nonwoven materials, nonwoven webs, and/or three-dimensional materials or webs described herein can comprise at least part of other articles such as scouring pads, wet or dry-mop pads (such as SWIFFER® pads), and the like.

The term "aperture", as used herein, refers to a regular or substantially regularly-shaped hole that is intentionally formed and extends completely through a web or structure (that is, a through hole). The apertures can either be punched cleanly through the web so that the material surrounding the aperture lies in the same plane as the web prior to the formation of the aperture (a "two dimensional" aperture), or the holes can be formed such that at least some of the material surrounding the opening is pushed out of the plane of the web. In the latter case, the apertures may resemble a depression with an aperture therein, and may be referred to herein as a "three dimensional" aperture, a subset of apertures.

The term "channel", as used herein, is a region or zone in a material layer that has a substantially lower basis weight (e.g., less than 50%, less than 70%, less than 90%) than the surrounding material in the material layer. The channel may be a region in a material layer that is substantially material-free (e.g., 90% material-free, 95% material-free, or 99% material-free, or completely material-free). A channel may extend through one or more material layers. The channels generally have a lower bending modulus than the surrounding regions of the material layer, enabling the material layer to bend more easily and/or contain more bodily exudates within the channels than in the surrounding areas of the material layer. Thus, a channel is not merely an indentation, compressed portion, or embossment in the material layer that does not create a reduced basis weight in the material layer in the area of the channel.

The term "component" of an absorbent article, as used herein, refers to an individual constituent of an absorbent article, such as a topsheet, acquisition layer, acquisition layer, distribution material, absorbent core or layers of absorbent cores, backsheets, and barriers such as barrier layers and barrier cuffs.

The term "cross-machine direction" or "CD", as used herein, means a path that is perpendicular to a machine direction in a plane of a web.

The term "deformable material", as used herein, is a material which is capable of changing its shape or density in response to applied stresses or strains.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roll, for example).

The term "disposable", as used herein, describes absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

The term "forming elements", as used herein, refers to any elements on a surface of a forming member that are capable of deforming a web.

The term "integral", as used herein as in "integral extension" when used to describe the protrusions, refers to fibers of the protrusions having originated from the fibers of the precursor web(s). Thus, as used herein, "integral" is to be distinguished from fibers introduced to or added to a separate precursor web for the purpose of making the protrusions.

The terms "join", "joined", "joined to", "attach", "attached", "attached to", "bond", "bonded", and "bonded to", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. These terms encompass configurations in which an element is secured to another element at selected locations, as well as configurations in which an element is completely secured to another element across the entire surface of one of the elements. These terms include any known manner in which elements can be secured including, but not limited to mechanical entanglement.

The term "machine direction" or "MD", as used herein, means a path that a material, such as a web, follows through a manufacturing process.

The term "macroscopic", as used herein, refers to structural features or elements that are readily visible and distinctly discernable to a human having 20/20 vision when the perpendicular distance between the viewer's eye and the web is about 12 inches (30 cm). Conversely, the term "microscopic" refers to such features that are not readily visible and distinctly discernable under such conditions.

The term "mechanically deforming", as used herein, refers to processes in which a mechanical force is exerted upon a material in order to permanently deform the material.

The term "permanently deformed", as used herein, refers to the state of a deformable material whose shape or density has been permanently altered in response to applied stresses or strains.

The terms "SELF" and "SELF'ing", as used herein, refer to Procter & Gamble technology in which SELF stands for Structural Elastic Like Film. While the process was originally developed for deforming polymer film to have beneficial structural characteristics, it has been found that the SELF'ing process can be used to produce beneficial structures in other materials. Processes, apparatuses, and patterns produced via SELF are illustrated and described in U.S. Pat. Nos. 5,518,801; 5,691,035; 5,723,087; 5,891,544; 5,916,663; 6,027,483; and 7,527,615 B2.

The term "tuft", as used herein, refers to a particular type of feature that may be formed from fibers in a nonwoven web. Tufts may have a tunnel-like configuration which may be open at both of their ends.

The term "web" is used herein to refer to a material whose primary dimension is X-Y, i.e., along its length (or longitudinal direction) and width (or transverse direction). It should be understood that the term "web" is not necessarily limited to single layers or sheets of material. Thus the web can comprise laminates or combinations of several sheets of the requisite type of materials.

The terms "Z-dimension" or "Z-direction", as used herein, refers to the dimension orthogonal to the length and width of the web or article. The Z-dimension usually corresponds to the thickness of the web or material. As used herein, the term "X-Y dimension" refers to the plane orthogonal to the thickness of the web or material. The X-Y dimension usually corresponds to the length and width, respectively, of the web or material.

Nonwoven Materials

The present disclosure is directed, in part, to high-loft nonwoven materials having discrete three-dimensional deformations, which deformations provide protrusions on one side of the nonwoven material, and openings on the other side of the nonwoven material. Methods of making the nonwoven materials are also disclosed. The nonwoven materials can be used in absorbent articles and other articles, as will be described in further detail below.

As used herein, the term "nonwoven" or "nonwoven material" refers to a web or material having a structure of individual fibers or threads which are interlaid, but not in a repeating pattern as in a woven or knitted fabric, which latter types of fabrics do not typically have randomly oriented or substantially randomly-oriented fibers. Nonwoven webs or materials will have a machine direction (MD) and a cross machine direction (CD) as is commonly known in the art of web manufacture. By "substantially randomly oriented" is meant that, due to processing conditions of the precursor web, there may be a higher amount of fibers oriented in the MD than the CD, or vice versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD.

The nonwoven webs of the present disclosure will first be described and then channels in various layers of the absorbent articles of the present disclosure will be set forth. Next, various color patterns and indicia patterns will be described.

Nonwoven webs and materials are often incorporated into products, such as absorbent articles, at high manufacturing line speeds. Such manufacturing processes can apply compressive and shear forces on the nonwoven webs that may damage certain types of three-dimensional features that have been purposefully formed in such webs. In addition, in the event that the nonwoven material is incorporated into a product (such as a disposable diaper) that is made or packaged under compression, it becomes difficult to preserve the three-dimensional character of some types of prior three-dimensional features after the material is subjected to such compressive forces.

Figure 2:
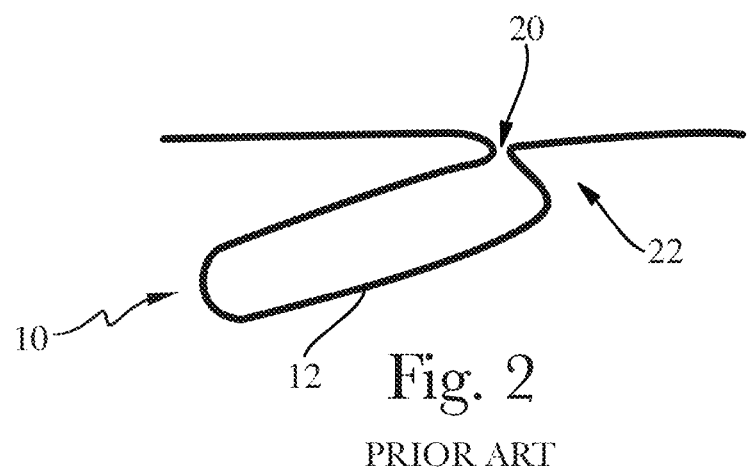
FIG. 2 is a schematic end view of a prior art tuft after it has been subjected to compression.

For example, FIGS. 1 and 2 show a prior art nonwoven material 10 with a tufted structure. The nonwoven material comprises tufts 12 formed from looped fibers 14 that form a tunnel-like structure having two ends 16. The tufts 12 extend outward from the plane of the nonwoven material in the Z-direction. The tunnel-like structure has a width that is substantially the same from one end of the tuft to the opposing end. Often, such tufted structures will have holes or openings 18 at both ends and an opening 20 at their base. Typically, the openings 18 at the ends of the tufts are at the machine direction (MD) ends of the tufts. The openings 18 at the ends of the tufts can be a result of the process used to form the tufts. If the tufts 12 are formed by forming elements in the form of teeth with a relatively small tip and vertical leading and trailing edges that form a sharp point, these leading and/or trailing edges may punch through the nonwoven web at least one of the ends of the tufts. As a result, openings 18 may be formed at one or both ends of the tufts 12.

Figure 3:
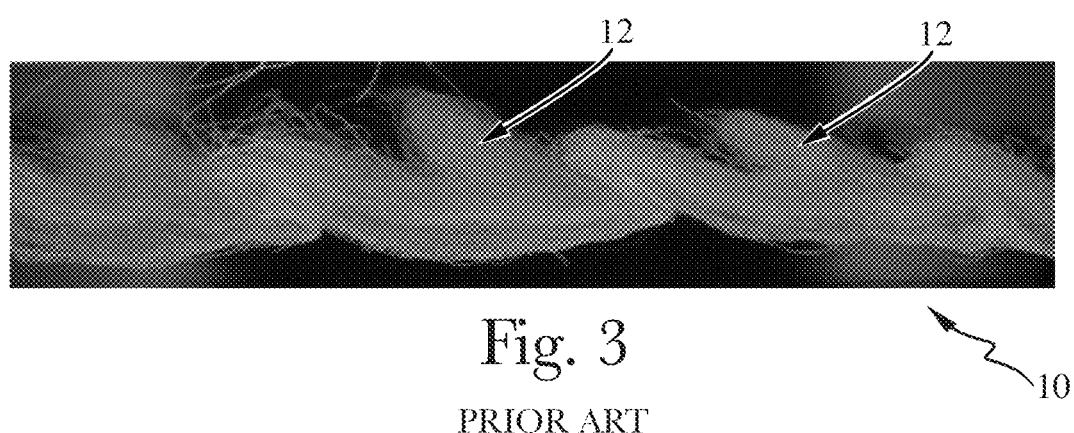
FIG. 3 is a photomicrograph of the end of a prior art nonwoven web showing a plurality of collapsed tufts.

While such a nonwoven material 10 provides well-defined tufts 12, the opening 20 at the base of the tuft structure can be relatively narrow and difficult to see with the naked eye. In addition, as shown in FIG. 2, the material of the tuft 12 surrounding this narrow base opening 20 may tend to form a hinge 22, or pivot point if forces are exerted on the tuft. If the nonwoven material 10 is compressed (such as in the Z-direction), in many cases, the tufts 12 can collapse to one side and close off the opening 20. Typically, a majority of the tufts in such a tufted material will collapse and close off the openings 20. FIG. 2 schematically shows an example of a tuft 12 after it has collapsed. In FIG. 2, the tuft 12 has folded over to the left side. FIG. 3 is an image showing a nonwoven material with several upwardly-oriented tufts, all of which have folded over to the side. However, not all of the tufts 12 will collapse and fold over to the same side. Often, some tufts 12 will fold to one side, and some tufts will fold to the other side. As a result of the collapse of the tufts 12, the openings 20 at the base of the tufts can close up, become slit-like, and virtually disappear.

Figure 4:
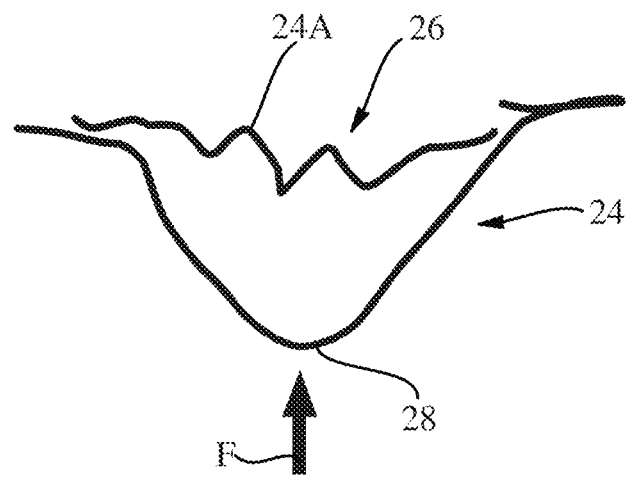
FIG. 4 is a schematic side view of a prior art conical-shaped structure before and after it has been subjected to compression.

Prior art nonwoven materials with certain other types of three dimensional deformations, such as conical structures, may also be subject to collapse when compressed. As shown in FIG. 4, conical structures 24 will not necessarily fold over as will certain tufted structures when subjected to compressive forces F. However, conical structures 24 can be subject to collapse in that their relatively wide base opening 26 and smaller tip 28 causes the conical structure to push back toward the plane of the nonwoven material, such as to the configuration designated 24A.

The nonwoven materials of at least some forms of the present disclosure described herein are intended to better preserve the structure of discrete three-dimensional features in the nonwoven materials after compression.

Figure 5:
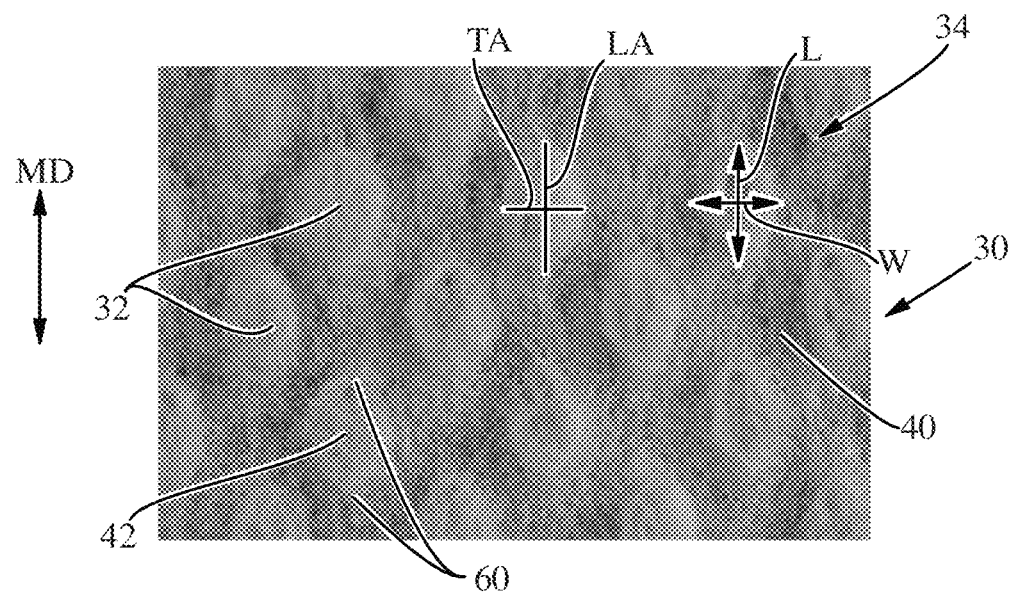
FIG. 5 is a plan view photomicrograph showing one side of a nonwoven material having three-dimensional deformations formed therein, with the protrusions oriented upward in accordance with the present disclosure.
Figure 6:
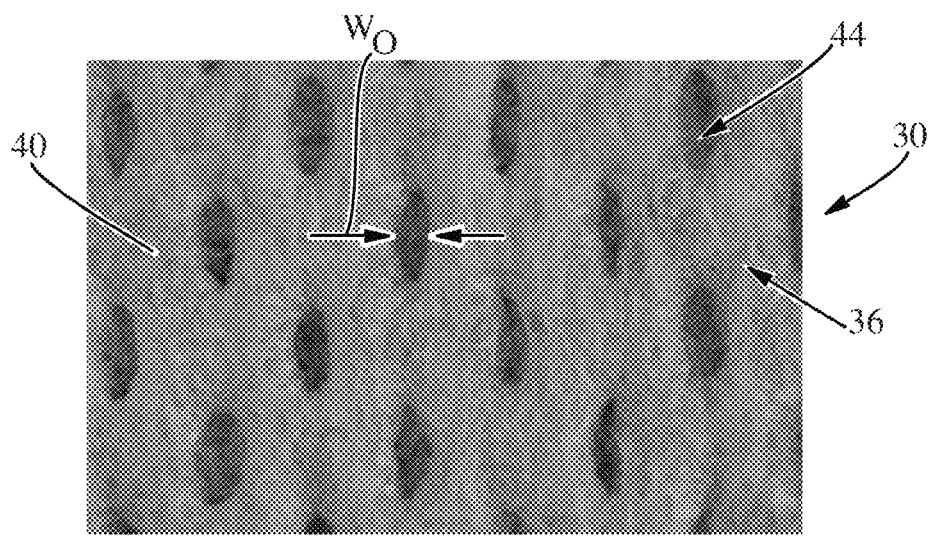
FIG. 6 is a plan view photomicrograph showing the other side of a nonwoven material similar to that shown in FIG. 5, with the openings in the nonwoven facing upward in accordance with the present disclosure.
Figure 7:
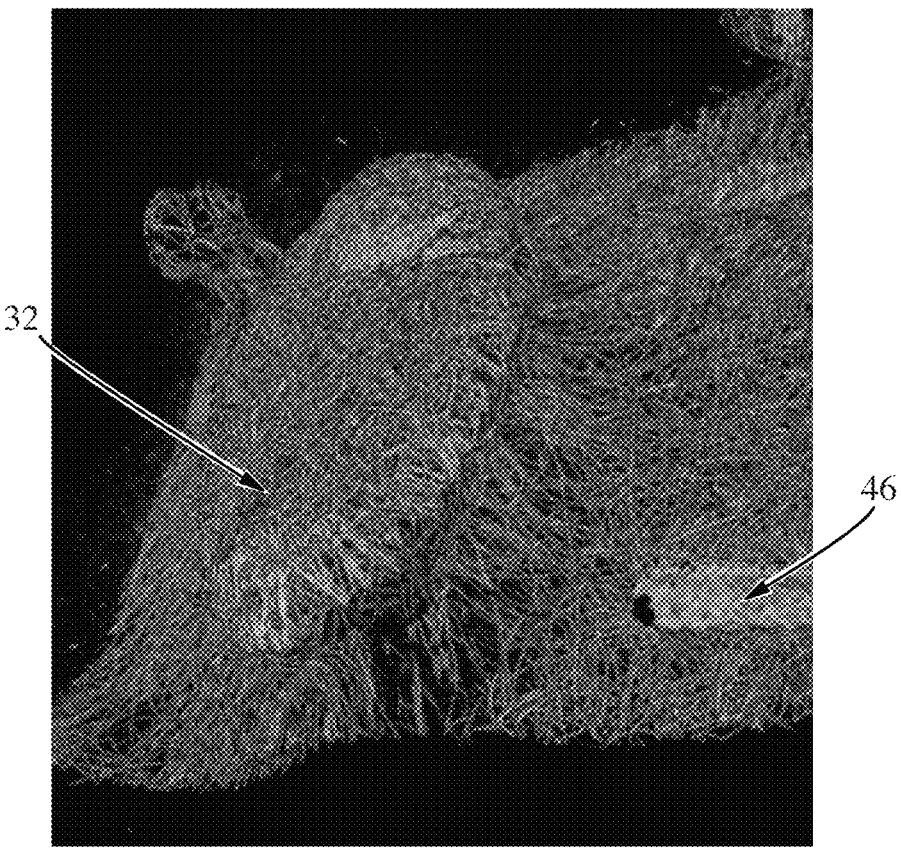
FIG. 7 is a Micro CT scan image showing a perspective view of a protrusion in a single layer nonwoven material in accordance with the present disclosure.
Figure 8:
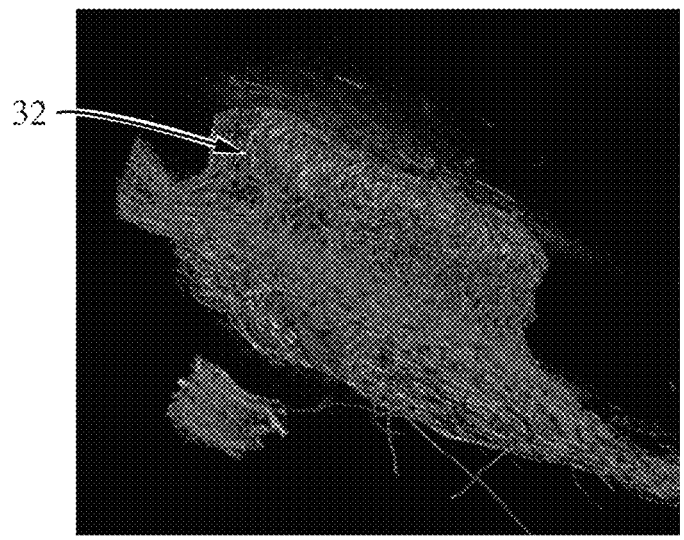
FIG. 8 is a Micro CT scan image showing a side of a protrusion in a single layer nonwoven material in accordance with the present disclosure.
Figure 9:
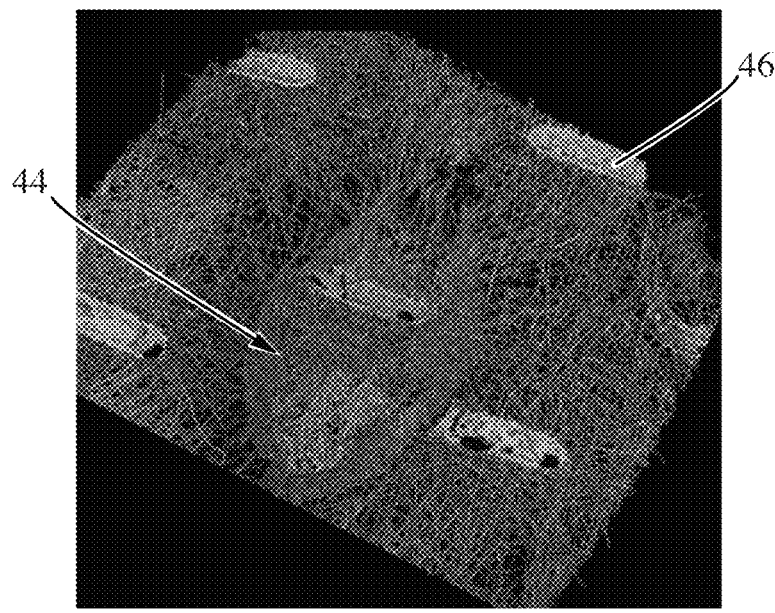
FIG. 9 is a Micro CT scan image showing a perspective view of a deformation with the opening facing upward in a single layer nonwoven material in accordance with the present disclosure.

FIGS. 5-14 show examples of nonwoven materials 30 with three-dimensional deformations comprising protrusions 32 therein. The nonwoven materials 30 have a first surface 34, a second surface 36, and a thickness T therebetween (the thickness being shown in FIG. 12). FIG. 5 shows the first surface 34 of a nonwoven material 30 with the protrusions 32 that extend outward from the first surface 34 of the nonwoven material oriented upward. FIG. 6 shows the second surface 36 of a nonwoven material 30 such as that shown in FIG. 5, having three-dimensional deformations formed therein, with the protrusions oriented downward and the base openings 44 oriented upward. FIG. 7 is a Micro CT scan image showing a perspective view of a protrusion 32. FIG. 8 is a Micro CT scan image showing a side view of a protrusion 32 (of one of the longer sides of the protrusion). FIG. 9 is a Micro CT scan image showing a perspective view of a deformation with the opening 44 facing upward. The nonwoven materials 30 comprise a plurality of fibers 38 (shown in FIGS. 7-11 and 14). As shown in FIGS. 7 and 9, the nonwoven material 30 may have a plurality of bonds 46 therein to hold the fibers 38 together. Any such bonds are typically present in the precursor material.

The protrusions 32 may, in some cases, be formed from looped fibers (which may be continuous) 38 that are pushed outward so that they extend out of the plane of the nonwoven web in the Z-direction. The protrusions 32 will typically comprise more than one looped fiber. In some cases, the protrusions 32 may be formed from looped fibers and at least some broken fibers. In addition, in the case of some types of nonwoven materials (such as carded materials, which are comprised of shorter fibers), the protrusions 32 may be formed from loops comprising multiple discontinuous fibers. Multiple discontinuous fibers in the form of a loop are shown as layer 30A in FIGS. 15A-15F. The looped fibers may either be aligned (that is, oriented in substantially the same direction), or not be aligned within the protrusions 32. Typically, if male/female forming elements are used to form the protrusions, and the female forming elements substantially surround the male forming elements, the fibers in the protrusions 32 may remain substantially randomly oriented (rather than aligned), similar to their orientation in the precursor web(s) from which the nonwoven materials 30 are formed.

The nonwoven material 30 may comprise a generally planar first region 40 and the three-dimensional deformations may comprise a plurality of discrete integral second regions 42. The term "generally planar" is not meant to imply any particular flatness, smoothness, or dimensionality. Thus, the first region 40 can include other features that provide the first region 40 with a topography. Such other features can include, but are not limited to small projections, raised network regions around the base openings 44, and other types of features. Thus, the first region 40 is generally planar when considered relative to the second regions 42.

Figure 10:
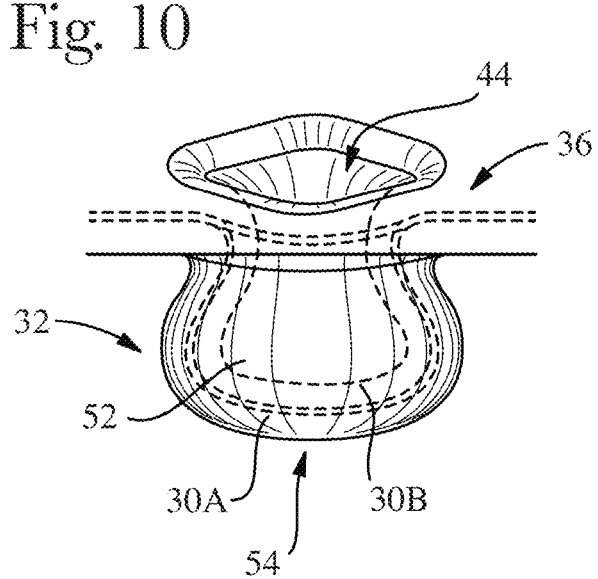
FIG. 10 is a perspective view of a deformation in a two layer nonwoven material with the opening facing upward in accordance with the present disclosure.

The term "deformation", as used herein, includes both the protrusions 32 formed on one side of the nonwoven material and the base openings 44 formed in the opposing side of the material. The base openings 44 are most often not in the form of an aperture or a through-hole. The base openings 44 may instead appear as depressions. The base openings 44 can be analogized to the opening of a bag. A bag has an opening that typically does not pass completely through the bag. In the case of the present nonwoven materials 30, as shown in FIG. 10, the base openings 44 open into the interior of the protrusions 32.

Figure 11:
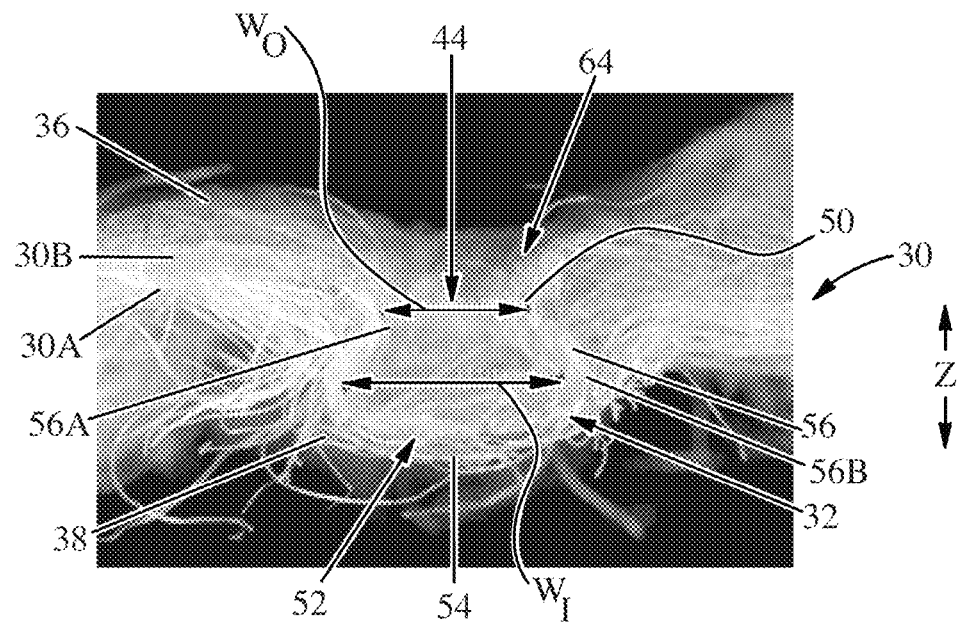
FIG. 11 is a photomicrograph of a cross-section taken along the transverse axis of a deformation showing one example of a multilayer nonwoven material having a three-dimensional deformation in the form of a protrusion on one side of the material that provides a wide opening on the other side of the material, with the opening facing upward in accordance with the present disclosure.

FIG. 11 shows one example of a multilayer nonwoven material 30 having a three-dimensional deformation in the form of a protrusion 32 on one side of the material that provides a wide base opening 44 on the other side of the material. The dimensions of "wide" base openings are described in further detail below. In this case, the base opening 44 is oriented upward in the figure. When there is more than one nonwoven layer, the individual layers can be designated 30A, 30B, etc. The individual layers 30A and 30B each have first and second surfaces, which can be designated similarly to the first and second surfaces 34 and 36 of the nonwoven material (e.g., 34A and 36A for the first and second surfaces of the first layer 30A; and, 34B and 36B for the first and second surfaces of the second layer 30B).

Figure 12:
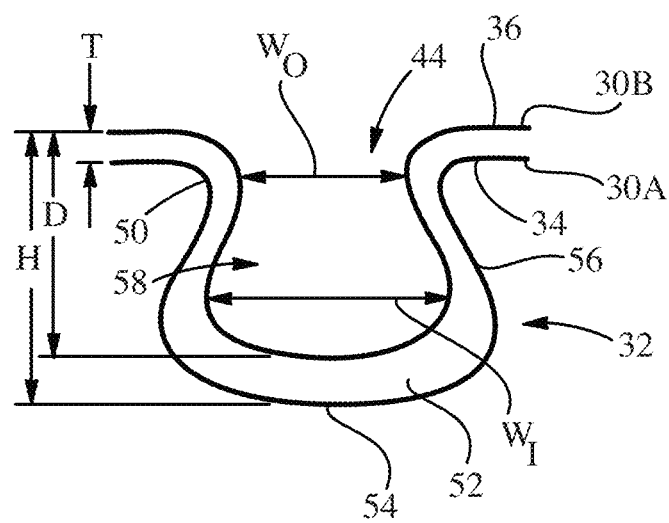
FIG. 12 is a schematic view of the protrusion shown in FIG. 11 in accordance with the present disclosure.

As shown in FIGS. 11 and 12, the protrusions 32 comprise: a base 50 proximate the first surface 34 of the nonwoven material; an opposed enlarged distal portion or cap portion, or "cap" 52, that extends to a distal end 54; side walls (or "sides") 56; an interior 58; and a pair of ends 60 (the latter being shown in FIG. 5). The "base" 50 of the protrusions 32 comprises the narrowest portion of the protrusion when viewed from one of the ends of the protrusion. The term "cap" does not imply any particular shape, other than it comprises the wider portion of the protrusion 32 that includes and is adjacent to the distal end 54 of the protrusion 32. The side walls 56 have an inside surface 56A and an outside surface 56B. As shown in FIGS. 11 and 12, the side walls 56 transition into, and may comprise part of the cap 52. Therefore, it is not necessary to precisely define where the side walls 56 end and the cap 52 begins. The cap 52 will have a maximum interior width, $W_I$, between the inside surfaces 56A of the opposing side walls 56. The cap 52 will also have a maximum exterior width W between the outside surfaces 56B of the opposing side walls 56. The ends 60 of the protrusions 32 are the portions of the protrusions that are spaced furthest apart along the longitudinal axis, L, of the protrusions.

As shown in FIGS. 11 and 12, the narrowest portion of the protrusion 32 defines the base opening 44. The base opening 44 has a width $W_O$. The base opening 44 may be located (in the z-direction) between the plane defined by the second surface 36 of the material and the distal end 54 of the protrusion. As shown in FIGS. 11 and 12, the nonwoven material 30 may have an opening in the second surface 36 (the "second surface opening" 64) that transitions into the base opening 44 (and vice versa), and is the same size as, or larger than the base opening 44. The base opening 44 will, however, generally be discussed more frequently herein since its size will often be more visually apparent to the consumer in those forms where the nonwoven material 30 is placed in an article with the base openings 44 visible to the consumer. It should be understood that in certain forms, such as in forms in which the base openings 44 face outward (for example, toward a consumer and away from the absorbent core in an absorbent article), it may be desirable for the base openings 44 not to be covered and/or closed off by another web.

As shown in FIG. 12, the protrusions 32 have a depth D measured from the second surface 36 of the nonwoven web to the interior of the protrusion at the distal end 54 of the protrusions. The protrusions 32 have a height H measured from the second surface 36 of the nonwoven web to the distal end 54 of the protrusions. In most cases the height H of the protrusions 32 will be greater than the thickness T of the first region 40. The relationship between the various portions of the deformations may be such that as shown in FIG. 11, when viewed from the end, the maximum interior width $W_I$ of the cap 52 of the protrusions is wider than the width, $W_O$, of the base opening 44.

The protrusions 32 may be of any suitable shape. Since the protrusions 32 are three-dimensional, describing their shape depends on the angle from which they are viewed. When viewed from above (that is, perpendicular to the plane of the web, or plan view) such as in FIG. 5, suitable shapes include, but are not limited to: circular, diamond-shaped, rounded diamond-shaped, U.S. football-shaped, oval-shaped, clover-shaped, triangle-shaped, tear-drop shaped, and elliptical-shaped. (The base openings 44 will typically have a shape similar to the plan view shape of the protrusions 32.) In other cases, the protrusions 32 (and base openings 44) may be non-circular. The protrusions 32 may have similar plan view dimensions in all directions, or the protrusions may be longer in one dimension than another. That is, the protrusions 32 may have different length and width dimensions. If the protrusions 32 have a different length than width, the longer dimension will be referred to as the length of the protrusions. The protrusions 32 may, thus, have a ratio of length to width, or an aspect ratio. The aspect ratios can range from about 1:1 to about 10:1.

As shown in FIG. 5, the protrusions 32 may have a width, W, that varies from one end 60 to the opposing end 60 when the protrusions are viewed in plan view. The width W may vary with the widest portion of the protrusions in the middle of the protrusions, and the width of the protrusions decreasing at the ends 60 of the protrusions. In other cases, the protrusions 32 could be wider at one or both ends 60 than in the middle of the protrusions. In still other cases, protrusions 32 can be formed that have substantially the same width from one end of the protrusion to the other end of the protrusion. If the width of the protrusions 32 varies along the length of the protrusions, the portion of the protrusion where the width is the greatest is used in determining the aspect ratio of the protrusions.

When the protrusions 32 have a length L that is greater than their width W, the length of the protrusions may be oriented in any suitable direction relative to the nonwoven material 30. For example, the length of the protrusions 32 (that is, the longitudinal axis, LA, of the protrusions) may be oriented in the machine direction, the cross-machine direction, or any desired orientation between the machine direction and the cross-machine direction. The protrusions 32 also have a transverse axis TA generally orthogonal to the longitudinal axis LA in the MD-CD plane. In the form shown in FIGS. 5 and 6, the longitudinal axis LA is parallel to the MD. In some forms, all the spaced apart protrusions 32 may have generally parallel longitudinal axes LA.

The protrusions 32 may have any suitable shape when viewed from the side. Suitable shapes include those in which there is a distal portion or "cap" with an enlarged dimension and a narrower portion at the base when viewed from at least one side. The term "cap" is analogous to the cap portion of a mushroom. (The cap does not need to resemble that of any particular type of mushroom. In addition, the protrusions 32 may, but need not, have a mushroom-like stem portion.) In some cases, the protrusions 32 may be referred to as having a bulbous shape when viewed from the end 60, such as in FIG. 11. The term "bulbous", as used herein, is intended to refer to the configuration of the protrusions 32 as having a cap 52 with an enlarged dimension and a narrower portion at the base when viewed from at least one side (particularly when viewing from one of the shorter ends 60) of the protrusion 32. The term "bulbous" is not limited to protrusions that have a circular or round plan view configuration that is joined to a columnar portion. The bulbous shape, in the form shown (where the longitudinal axis LA of the deformations 32 is oriented in the machine direction), may be most apparent if a section is taken along the transverse axis TA of the deformation (that is, in the cross-machine direction). The bulbous shape may be less apparent if the deformation is viewed along the length (or longitudinal axis LA) of the deformation such as in FIG. 8.

The protrusions 32 may comprise fibers 38 that at least substantially surround the sides of the protrusions. This means that there are multiple fibers that extend (e.g., in the Z-direction) from the base 50 of the protrusions 32 to the distal end 54 of the protrusions, and contribute to form a portion of the sides 56 and cap 52 of a protrusion. The phrase "substantially surround" does not require that each individual fiber be wrapped in the X-Y plane substantially or completely around the sides of the protrusions. If the fibers 38 are located completely around the sides of the protrusions, this would mean that the fibers are located 360° around the protrusions. The protrusions 32 may be free of large openings at their ends 60, such as those openings 18 at the leading end and trailing end of the tufts shown in FIG. 1. The protrusions 32 also differ from embossed structures such as shown in FIG. 4. Embossed structures typically do not have distal portions that are spaced perpendicularly away (that is, in the Z-direction) from their base that are wider than portions that are adjacent to their base, as in the case of the cap 52 on the present protrusions 32.

The protrusions 32 may have certain additional characteristics. As shown in FIGS. 11 and 12, the protrusions 32 may be substantially hollow. As used herein, the term "substantially hollow" refers to structures which the protrusions 32 are substantially free of fibers in interior of protrusions. The term "substantially hollow", does not, however, require that the interior of the protrusions must be completely free of fibers. Thus, there can be some fibers inside the protrusions. "Substantially hollow" protrusions are distinguishable from filled three-dimensional structures, such as those made by laying down fibers, such as by airlaying or carding fibers onto a forming structure with recesses therein.

The side walls 56 of the protrusions 32 can have any suitable configuration. The configuration of the side walls 56, when viewed from the end of the protrusion such as in FIG. 11, can be linear or curvilinear, or the side walls can be formed by a combination of linear and curvilinear portions. The curvilinear portions can be concave, convex, or combinations of both. For example, the side walls 56 in the form show in FIG. 11, comprise portions that are curvilinear concave inwardly near the base of the protrusions and convex outwardly near the cap of the protrusions. The sidewalls 56 and the area around the base opening 44 of the protrusions may, under 20× magnification, have a visibly significantly lower concentration of fibers per given area (which may be evidence of a lower basis weight or lower opacity) than the portions of the nonwoven in the unformed first region 40. The protrusions 32 may also have thinned fibers in the sidewalls 56. The fiber thinning, if present, will be apparent in the form of necked regions in the fibers 38 as seen in scanning electron microscope (SEM) images taken at 200× magnification. Thus, the fibers may have a first cross-sectional area when they are in the undeformed nonwoven precursor web, and a second cross-sectional area in the side walls 56 of the protrusions 32 of the deformed nonwoven web, wherein the first cross-sectional area is greater than the second cross-sectional area. The side walls 56 may also comprise some broken fibers as well.

In some forms, the distal end 54 of the protrusions 32 may be comprised of original basis weight, non-thinned, and non-broken fibers. If the base opening 44 faces upward, the distal end 54 will be at the bottom of the depression that is formed by the protrusion. The distal end 54 will be free from apertures formed completely through the distal end. Thus, the nonwoven materials may be nonapertured. The term "apertures", as used herein, refers to holes formed in the nonwovens after the formation of the nonwovens, and does not include the pores typically present in nonwovens. The term "apertures" also does not refer to irregular breaks (or interruptions) in the nonwoven material(s) such as shown in FIGS. 15D-15F and FIG. 20 resulting from localized tearing of the material(s) during the process of forming deformations therein, which breaks may be due to variability in the precursor material(s). The distal end 54 may have relatively greater fiber concentration or density in comparison to the remaining portions of the structure that forms the protrusions. As described in greater detail below, however, if the nonwoven web is comprised of more than one layer, the concentration of fibers in the different portions of the protrusions may vary between the different layers.

The protrusions 32 may be of any suitable size. The size of the protrusions 32 can be described in terms of protrusion length, width, caliper, height, depth, cap size, and opening size. (Unless otherwise stated, the length L and width W of the protrusions are the exterior length and width of the cap 52 of the protrusions.) The dimensions of the protrusions and openings can be measured before and after compression (under either a pressure of 7 kPa or 35 KPa, whichever is specified) in accordance with the Accelerated Compression Method described in the Test Methods section. The protrusions have a caliper that is measured between the same points as the height H, but under a 2 KPa load, in accordance with the Accelerated Compression Method. All dimensions of the protrusions and openings other than caliper (that is, length, width, height, depth, cap size, and opening size) are measured without pressure applied at the time of making the measurement using a microscope at 20× magnification.

In some forms, the length of the cap 52 may be in a range from about 1.5 mm to about 10 mm. In some forms, the width of the cap (measured where the width is the greatest) may be in a range from about 1.5 mm to about 5 mm. The cap portion of the protrusions may have a plan view surface area of at least about 3 mm$^2$. In some forms, the protrusions may have a pre-compression height H that is in a range from about 1 mm to about 10 mm, alternatively from about 1 mm to about 6 mm. In some forms, the protrusions may have a post-compression height H that is in a range from about 0.5 mm to about 6 mm, alternatively from about 0.5 mm to about 1.5 mm. In some forms, the protrusions may have a depth D, in an uncompressed state that is in a range from about 0.5 mm to about 9 mm, alternatively from about 0.5 mm to about 5 mm. In some forms, the protrusions may have a depth D, after compression that is in a range from about 0.25 mm to about 5 mm, alternatively from about 0.25 mm to about 1 mm.

The nonwoven material 30 can comprise a composite of two or more nonwoven materials that are joined together. In such a case, the fibers and properties of the first layer will be designated accordingly (e.g., the first layer is comprised of a first plurality of fibers), and the fibers and properties of the second and subsequent layers will be designated accordingly (e.g., the second layer is comprised of a second plurality of fibers). In a two or more layer structure, there are a number of possible configurations the layers may take following the formation of the deformations therein. These will often depend on the extensibility of the nonwoven materials used for the layers. It is desirable that at least one of the layers have deformations which form protrusions 32 as described herein in which, along at least one cross-section, the width of the cap 52 of the protrusions is greater than the width of the base opening 44 of the deformations. For example, in a two layer structure where one of the layers will serve as the topsheet of an absorbent article and the other layer will serve as an underlying layer (such as an acquisition layer), the layer that has protrusions therein may comprise the topsheet layer. The layer that most typically has a bulbous shape will be the one which is in contact with the male forming member during the process of deforming the web. FIG. 15A-FIG. 15E show different alternative forms of three-dimensional protrusions 32 in multiple layer materials.

Figure 15A:
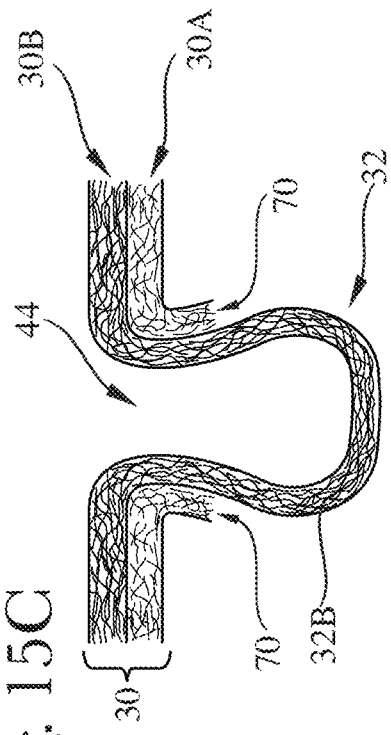
FIG. 15A is a cross-sectional view taken along the transverse axis of a deformation of one form of a multilayer nonwoven web shown with the base opening facing upward in accordance with the present disclosure.

In certain forms, such as shown in FIGS. 11, 12, and 15A, similar-shaped looped fibers may be formed in each layer of multiple layer nonwoven materials, including in the layer 30A that is spaced furthest from the discrete male forming elements during the process of forming the protrusions therein, and in the layer 30B that is closest to the male forming elements during the process. One layer such as 30B fits within the other layer, such as 30A. These layers may be referred to as a "nested" structure. Formation of a nested structure may require the use of two (or more) highly extensible nonwoven precursor webs. In the case of two layer materials, nested structures may form two complete loops, or (as shown in some of the following drawing figures) two incomplete loops of fibers.

As shown in FIG. 15A, a three-dimensional protrusion 32 comprises protrusions 32A formed in the first layer 30A and protrusions 32B formed in the second layer 30B. In a form, the first layer 30A may be incorporated into an absorbent article as an acquisition layer, and the second layer 30B may be a topsheet, and the protrusions formed by the two layers may fit together (that is, are nested). In this form, the protrusions 32A and 32B formed by the first and second layers 30A and 30B fit closely together. The three-dimensional protrusion 32A comprises a plurality of fibers 38A and the three-dimensional protrusion 32B comprises a plurality of fibers 38B. The three-dimensional protrusion 32B is nested into the three-dimensional protrusion 32A. In the form shown, the fibers 38A in the first layer 30A are shorter in length than the fibers 38B in the second layer 30B. In other forms, the relative length of fibers in the layers may be the same, or in the opposite relationship wherein the fibers in the first layer are longer than those in the second layer. In addition, in this form, and any of the other forms described herein, the nonwoven layers can be inverted when incorporated into an absorbent article, or other article, so that the protrusions 32 face upward (or outward). In such a case, the material suitable for the topsheet will be used in layer 30A, and material suitable for the underlying layer will be used in layer 30B.

Figure 15B:
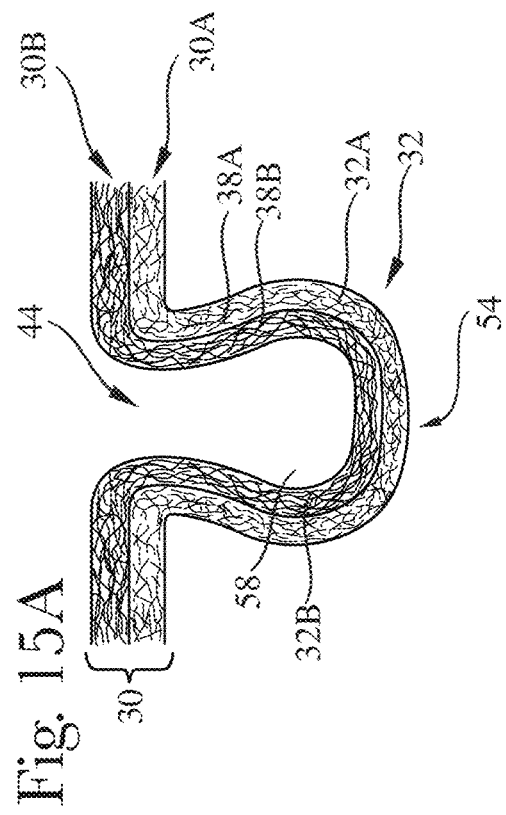
FIG. 15B is a cross-sectional view taken along the transverse axis of a deformation of an alternative form of a multilayer nonwoven web shown with the base opening facing upward in accordance with the present disclosure.

FIG. 15B shows that the nonwoven layers need not be in a contacting relationship within the entirety of the protrusion 32. Thus, the protrusions 32A and 32B formed by the first and second layers 30A and 30B may have different heights and/or widths. The two materials may have substantially the same shape in the protrusion 32 as shown in FIG. 15B (where one of the materials has the same the curvature as the other). In other forms, however, the layers may have different shapes. It should be understood that FIG. 15B shows only one possible arrangement of layers, and that many other variations are possible, but that as in the case of all the figures, it is not possible to provide a drawing of every possible variation.

Figure 15C:
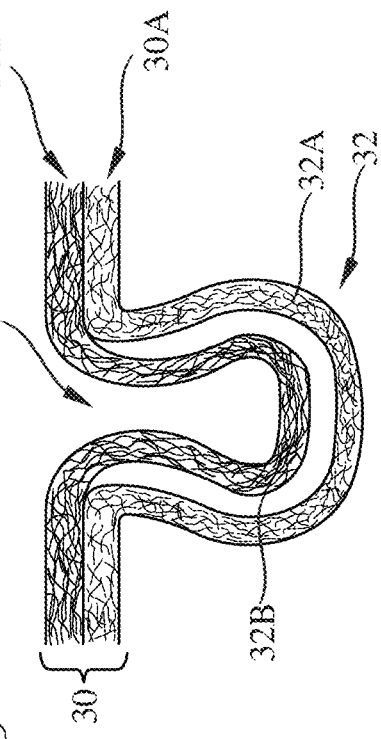
FIG. 15C is a cross-sectional view taken along the transverse axis of a deformation of an alternative form of a multilayer nonwoven web shown with the base opening facing upward in accordance with the present disclosure.

As shown in FIG. 15C, one of the layers, such as first layer 30A (e.g., an acquisition layer) may be ruptured in the area of the three-dimensional protrusion 32. As shown in FIG. 15C, the protrusions 32 are only formed in the second layer 30B (e.g., the topsheet) and extend through openings in the first layer 30A. That is, the three-dimensional protrusion 32B in the second layer 30B interpenetrates the ruptured first layer 30A. Such a structure may place the topsheet in direct contact an underlying distribution material or absorbent core, which may lead to improved dryness. In such a form, the layers are not considered to be "nested" in the area of the protrusion. (In the other forms shown in FIGS. 15D-15F, the layers would still be considered to be "nested".) Such a structure may be formed if the material of the second layer 30B is much more extensible than the material of the first layer 30A. In such a case, the openings can be formed by locally rupturing first precursor web by the process described in detail below. The ruptured layer may have any suitable configuration in the area of the protrusion 32. Rupture may involve a simple splitting open of first precursor web, such that the opening in the first layer 30A remains a simple two-dimensional aperture. However, for some materials, portions of the first layer 30A can be deflected or urged out-of-plane (i.e., out of the plane of the first layer 30A) to form flaps 70. The form and structure of any flaps is highly dependent upon the material properties of the first layer 30A. Flaps can have the general structure shown in FIG. 15C. In other forms, the flaps 70 can have a more volcano-like structure, as if the protrusion 32B is erupting from the flaps.

Figure 15D:
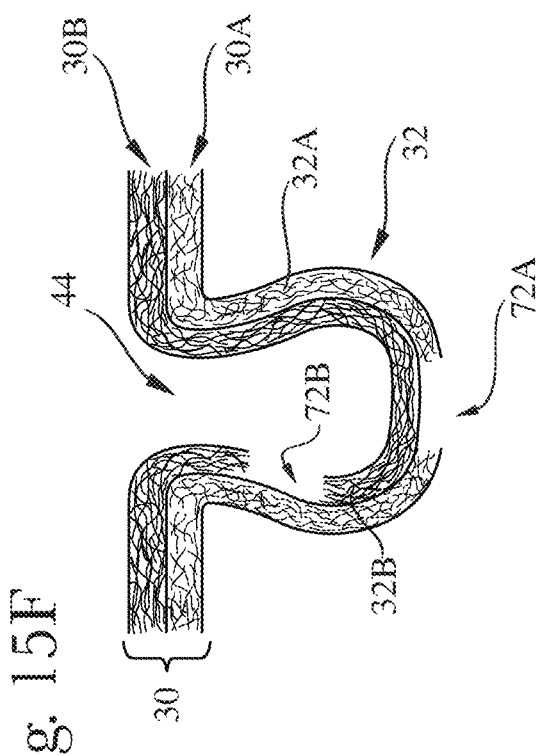
FIG. 15D is a cross-sectional view taken along the transverse axis of a deformation of an alternative form of a multilayer nonwoven web shown with the base opening facing upward in accordance with the present disclosure.
Figure 15F:
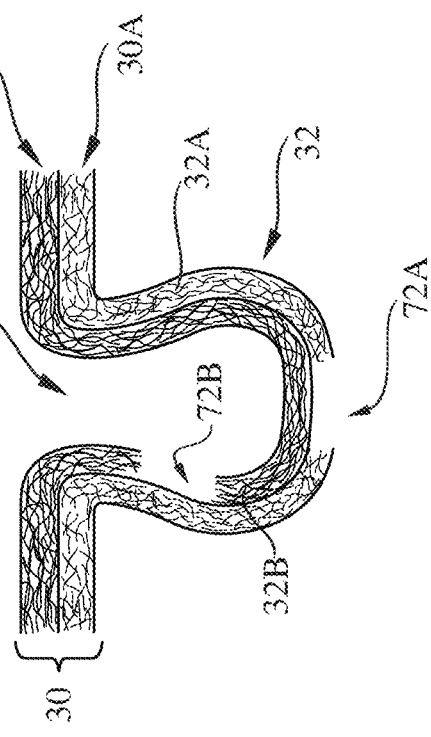
FIG. 15F is a cross-sectional view taken along the transverse axis of a deformation of an alternative form of a multilayer nonwoven web shown with the base opening facing upward in accordance with the present disclosure.
Figure 15E:
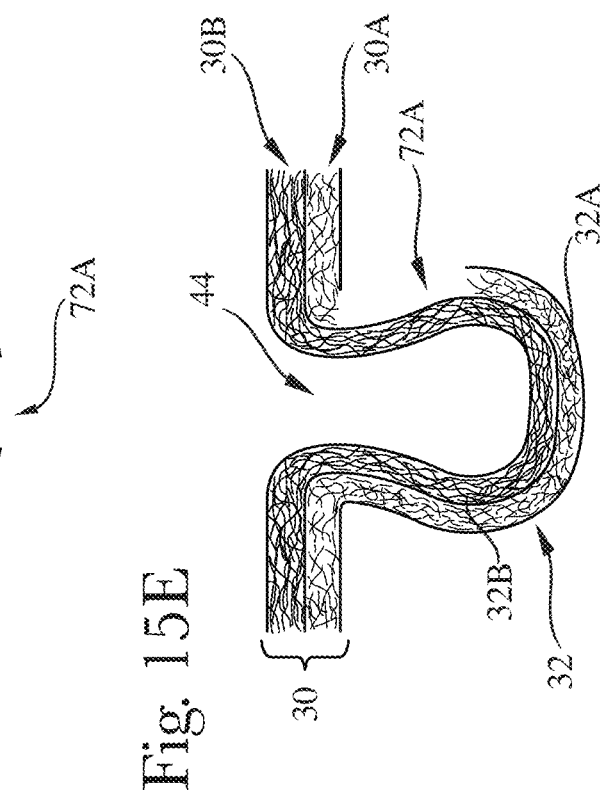
FIG. 15E is a cross-sectional view taken along the transverse axis of a deformation of an alternative form of a multilayer nonwoven web shown with the base opening facing upward in accordance with the present disclosure.

Alternatively, as shown in FIGS. 15D-15F, one or both of the first layer 30A and the second layer 30B may be interrupted (or have a break therein) in the area of the three-dimensional protrusion 32. FIGS. 15D and 15E show that the three-dimensional protrusion 32A of the first layer 30A may have an interruption 72A therein. The three-dimensional protrusion 32B of the non-interrupted second layer 30B may coincide with and fit together with the three-dimensional protrusion 32A of the interrupted first layer 30A. Alternatively, FIG. 15F shows a form in which both the first and second layers 30A and 30B have interruptions, or breaks, therein (72A and 72B, respectively). In this case, the interruptions in the layers 30A and 30B are in different locations in the protrusion 32. FIGS. 15D-15F show unintentional random or inconsistent breaks in the materials typically formed by random fiber breakage, which are generally misaligned and can be in the first or second layer, but are not typically aligned and completely through both layers. Thus, there typically will not be an aperture formed completely through all of the layers at the distal end 54 of the protrusions 32.

Figure 16:
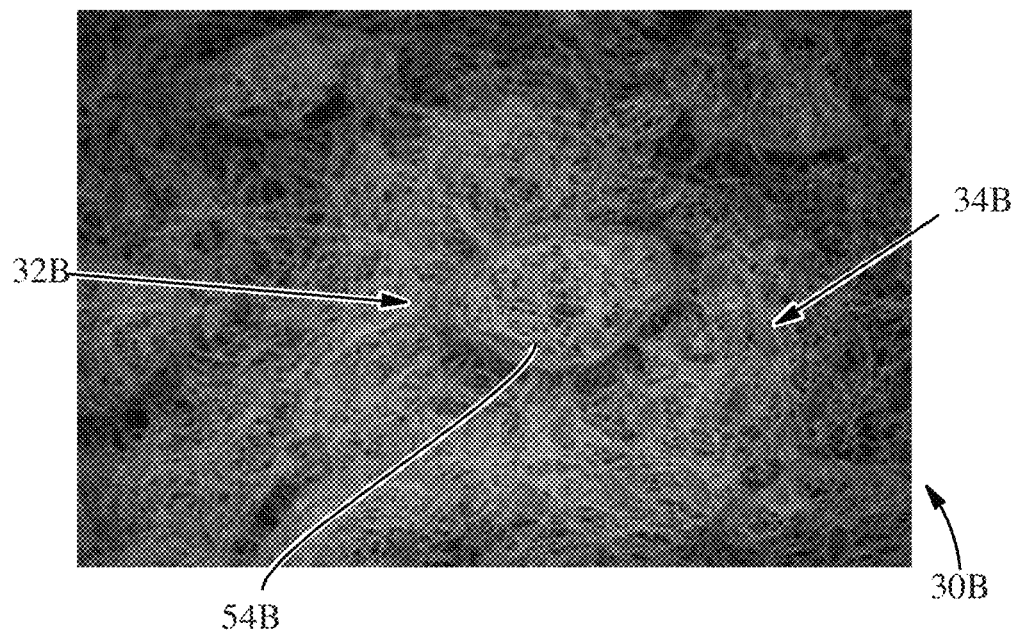
FIG. 16 is a plan view photomicrograph of a nonwoven web with the protrusions oriented upward showing the concentration of fibers in one layer of a two layer structure in accordance with the present disclosure.
Figure 17:
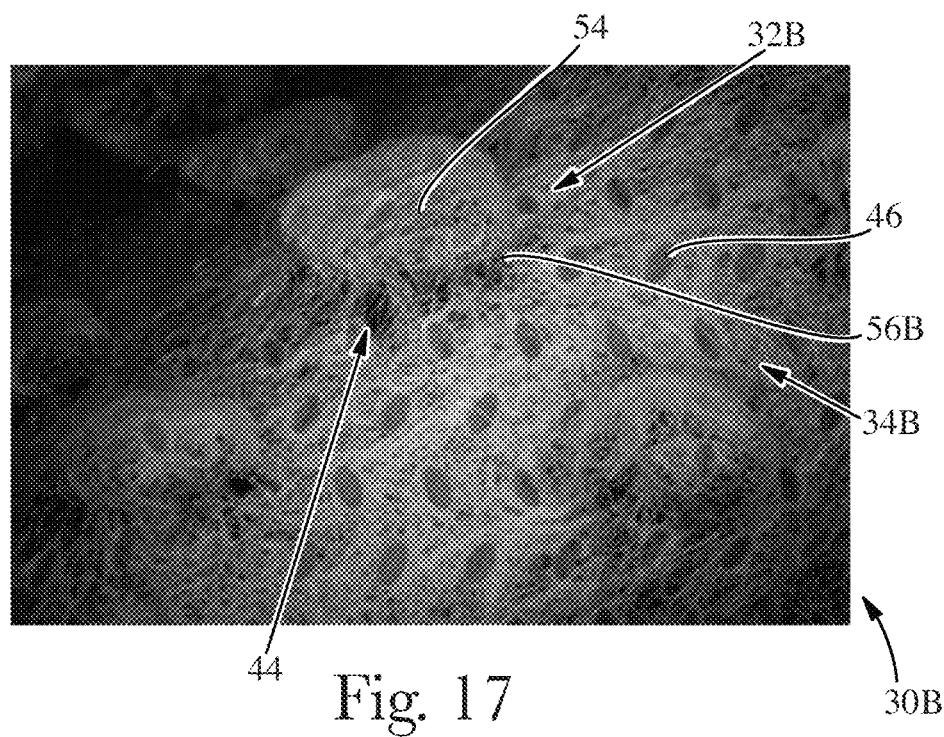
FIG. 17 is a perspective view photomicrograph showing the reduced fiber concentration in the side walls of the protrusions in a layer similar to that shown in FIG. 16 in accordance with the present disclosure.
Figure 18:
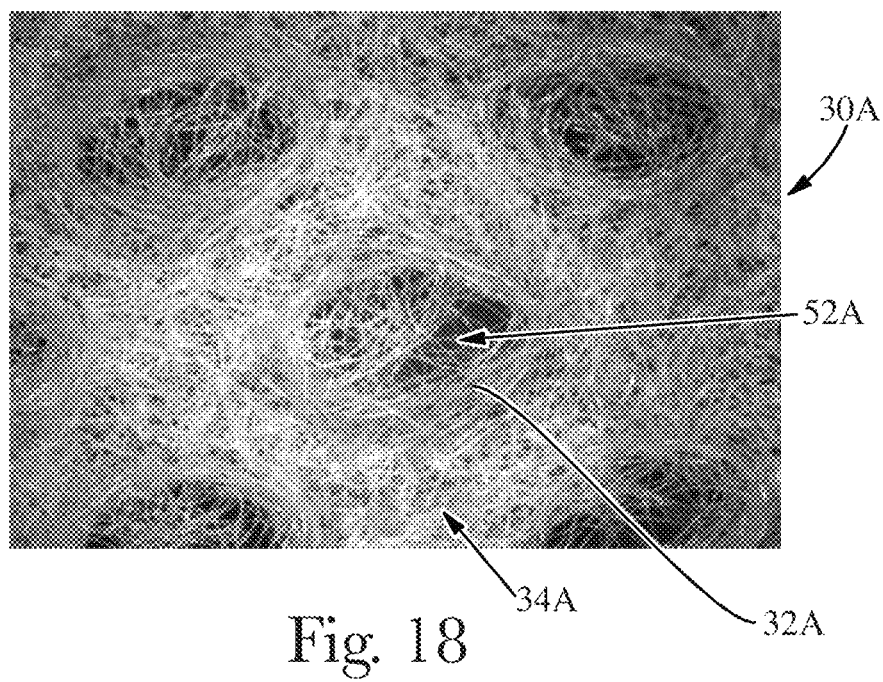
FIG. 18 is a plan view photomicrograph of a nonwoven web with the protrusions oriented upward showing the reduced concentration of fibers in the cap of a protrusion in the other layer of a two layer structure in accordance with the present disclosure.
Figure 19:
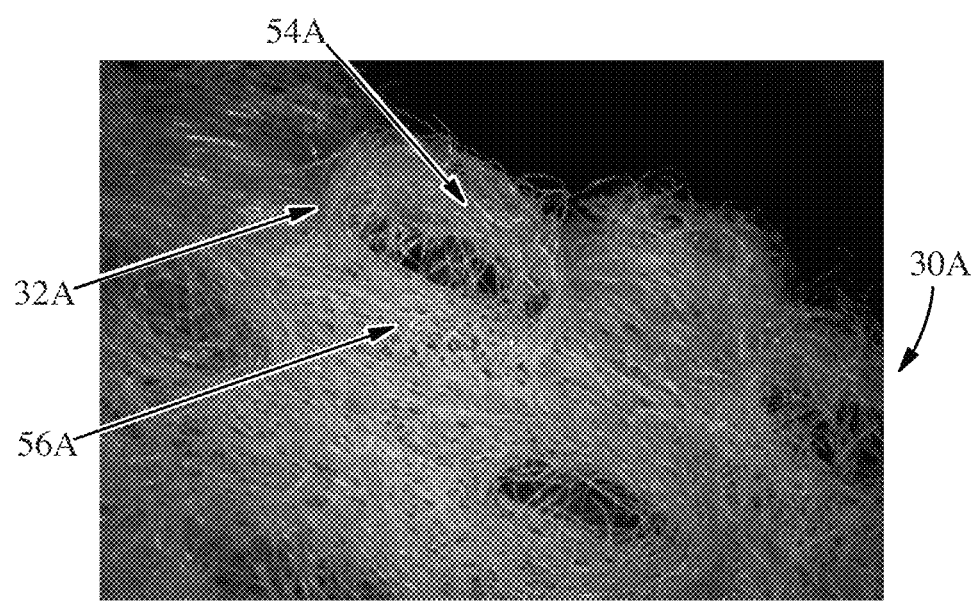
FIG. 19 is a perspective view photomicrograph showing the increased fiber concentration in the side walls of the protrusions in a layer similar to that shown in FIG. 18 in accordance with the present disclosure.

For dual layer and other multiple layer structures, the basis weight distribution (concentration of fibers) within the deformed material 30 can be different between the layers. As shown in FIG. 16, the nonwoven layer in contact with the male forming element (e.g., 30B) may have a large portion at the distal end 54B of the protrusion 32B with a similar basis weight to the original nonwoven. As shown in FIG. 17, the basis weight in the sidewalls 56B of the protrusion 32B and near the base opening 44 may be lower than the basis weight of the original material and the distal end 54 of the protrusion 32B. As shown in FIG. 18, the nonwoven layer in contact with the female forming element (e.g., 30A) may, however, have significantly less basis weight in the cap 52A of the protrusion 32A than in the original nonwoven. As shown in FIG. 19, the sidewalls 56A of the protrusion 32A may have less basis weight than the original nonwoven, but more basis weight than the distal end 54A of the protrusion 32A.

The base openings 44 can be of any suitable shape and size. The shape of the base opening 44 will typically be similar to, or the same as, the plan view shape of the corresponding protrusions 32. The base opening 44 may have a width that is greater than about any of the following dimensions before (and after compression): 0.5 mm, 0.7 mm, 0.8 mm, 0.9 mm, 1 mm, or any 0.1 mm increment above 1 mm. The width of the base opening 44 may be in a range that is from any of the foregoing amounts up to about 4 mm, or more. The base openings 44 may have a length that ranges from about 1.5 mm or less to about 10 mm, or more. The base openings 44 may have an aspect ratio that ranges from about 1:1 to 20:1, alternatively from about 1:1 to 10:1. Measurements of the dimensions of the base opening can be made on a photomicrograph. When the size of the width of the base opening 44 is specified herein, it will be appreciated that if the openings are not of uniform width in a particular direction, the width, $W_O$, is measured at the widest portion as shown in FIG. 6. The nonwoven materials of the present disclosure and the method of making the same may create deformations with a wider opening than certain prior structures which have a narrow base. This allows the base openings 44 to be more visible to the naked eye. The width of the base opening 44 is of interest because, being the narrowest portion of the opening, it will be most restrictive of the size of the opening. The deformations retain their wide base openings 44 after compression perpendicular to the plane of the first region 40.

The deformations may compress under load. In some cases, it may be desirable that the load is low enough so that, if the nonwoven is worn against a wearer's body, with the deformations in contact with the wearer's body, the deformations will be soft and will not imprint the skin. This applies in cases where either the protrusions 32 or the base openings 44 are oriented so that they are in contact with the wearer's body. For example, it may be desirable for the deformations to compress under pressures of 2 kPa or less. In other cases, it will not matter if the deformations imprint the wearer's skin. It may be desirable for at least one of the protrusions 32 in the nonwoven material 30 to collapse or buckle in the controlled manner described below under the 7 KPa load when tested in accordance with the Accelerated Compression Method in the Test Methods section below. Alternatively, at least some, or in other cases, a majority of the protrusions 32 may collapse in the controlled manner described herein. Alternatively, substantially all of the protrusions 32 may collapse in the controlled manner described herein. The ability of the protrusions 32 to collapse may also be measured under a load of 35 kPa. The 7 kPa and 35 kPa loads simulate manufacturing and compression packaging conditions. Wear conditions can range from no or limited pressure (if the wearer is not sitting on the absorbent article) up to 2 kPa, 7 kPa, or more.

Figure 13:
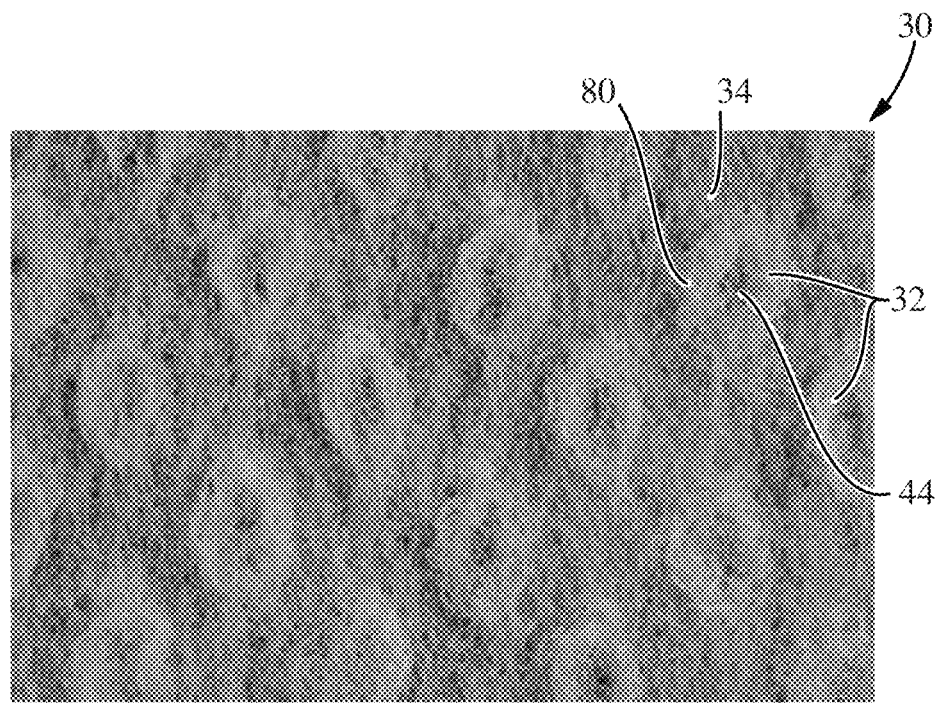
FIG. 13 is a plan view photomicrograph from the protrusion side of a material after it has been subjected to compression showing the high fiber concentration region around the perimeter of the protrusion in accordance with the present disclosure.
Figure 14:
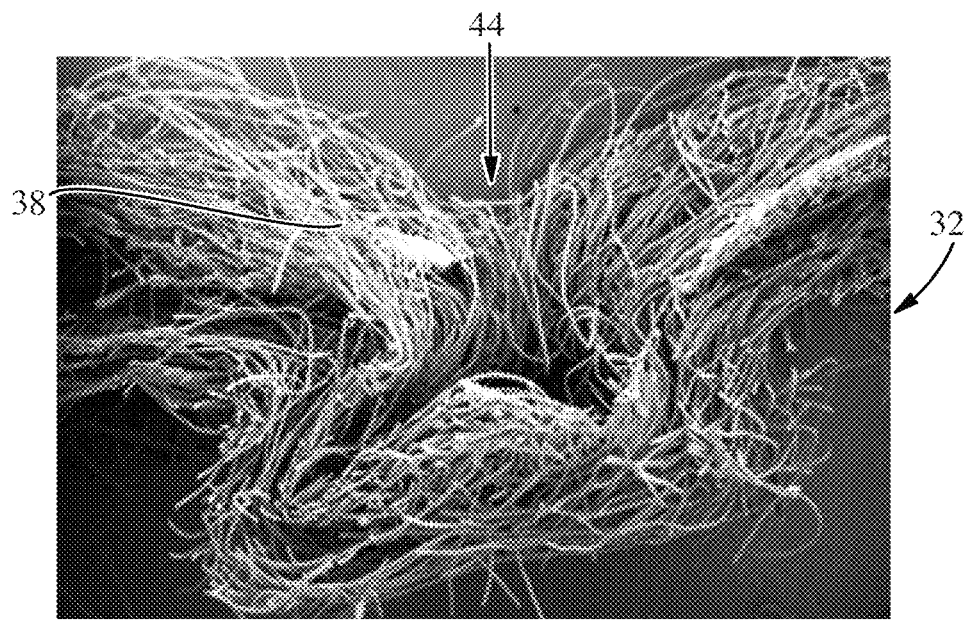
FIG. 14 is a photomicrograph of the cross-section of a protrusion taken along the transverse axis of the protrusion showing the protrusion after it has been subjected to compression in accordance with the present disclosure.

The protrusions 32 may collapse in a controlled manner after compression to maintain the wide opening 44 at the base. FIG. 13 shows the first surface 34 of a nonwoven material 30 according to the present disclosure after it has been subjected to compression. FIG. 14 is a side view of a single downwardly-oriented protrusion 32 after it has been subjected to compression. As shown in FIG. 13, when the protrusions 32 have been compressed, there appears to be a higher concentration of fibers in the form of a ring of increased opacity 80 around the base opening 44. When a compressive force is applied to the nonwoven materials, the side walls 56 of the protrusions 32 may collapse in a more desirable/controlled manner such that the side walls 56 become concave and fold into regions of overlapping layers (such as into an s-shape/accordion-shape). The ring of increased opacity 80 represents folded layers of material. In other words, the protrusions 32 may have a degree of dimensional stability in the X-Y plane when a Z-direction force is applied to the protrusions. It is not necessary that the collapsed configuration of the protrusions 32 be symmetrical, only that the collapsed configuration prevent the protrusions 32 from flopping over or pushing back into the original plane of the nonwoven, and significantly reducing the size of the base opening. For example, as shown in FIG. 14, the left side of the protrusion 32 can form a z-folded structure, and the right side of the protrusion does not, but still appears, when viewed from above, to have higher opacity due to a degree of overlapping of the material in the folded portion. Without wishing to be bound to any particular theory, it is believed that the wide base opening 44 and large cap 52 (greater than the width of the base opening 44), combined with the lack of a pivot point, causes the protrusions 32 to collapse in a controlled manner (prevents the protrusion 32 from flopping over). Thus, the protrusions 32 are free of a hinge structure that would otherwise permit them to fold to the side when compressed. The large cap 52 also prevents the protrusion 32 from pushing back into the original plane of the nonwoven.

The deformations can be disposed in any suitable density across the surface of the nonwoven material 30. The deformations may, for example, be present in a density of: from about 5 to about 100 deformations; alternatively from about 10 to about 50 deformations; alternatively from about 20 to about 40 deformations, in an area of 10 cm$^2$.

The deformations can be disposed in any suitable arrangement across the plane of the nonwoven material. Suitable arrangements include, but are not limited to: staggered arrangements, and zones. In some cases, the nonwoven material 30 may comprise both deformations and other features known in the art such as embossments and apertures. The deformations and other features may be in separate zones, be intermixed, or overlap. Intermixed arrangements can be created in any suitable manner. In some cases, intermixed arrangements can be created by using the techniques described in U.S. Patent Publication No. US 2012/0064298 A1, Orr, et al. In other cases, overlapping arrangements can be created by forming the deformations and then subsequently passing the nonwoven web between a forming member having male forming elements thereon and a compliant surface, and applying pressure to the web with the forming member and compliant surface. These techniques for producing overlapping arrangements enable deformations and other features to be combined so they are disposed in different locations on the nonwoven material or they can cause at least some of the deformations and at least some of the other features to be disposed in the same location on the nonwoven material.

Figure 25:
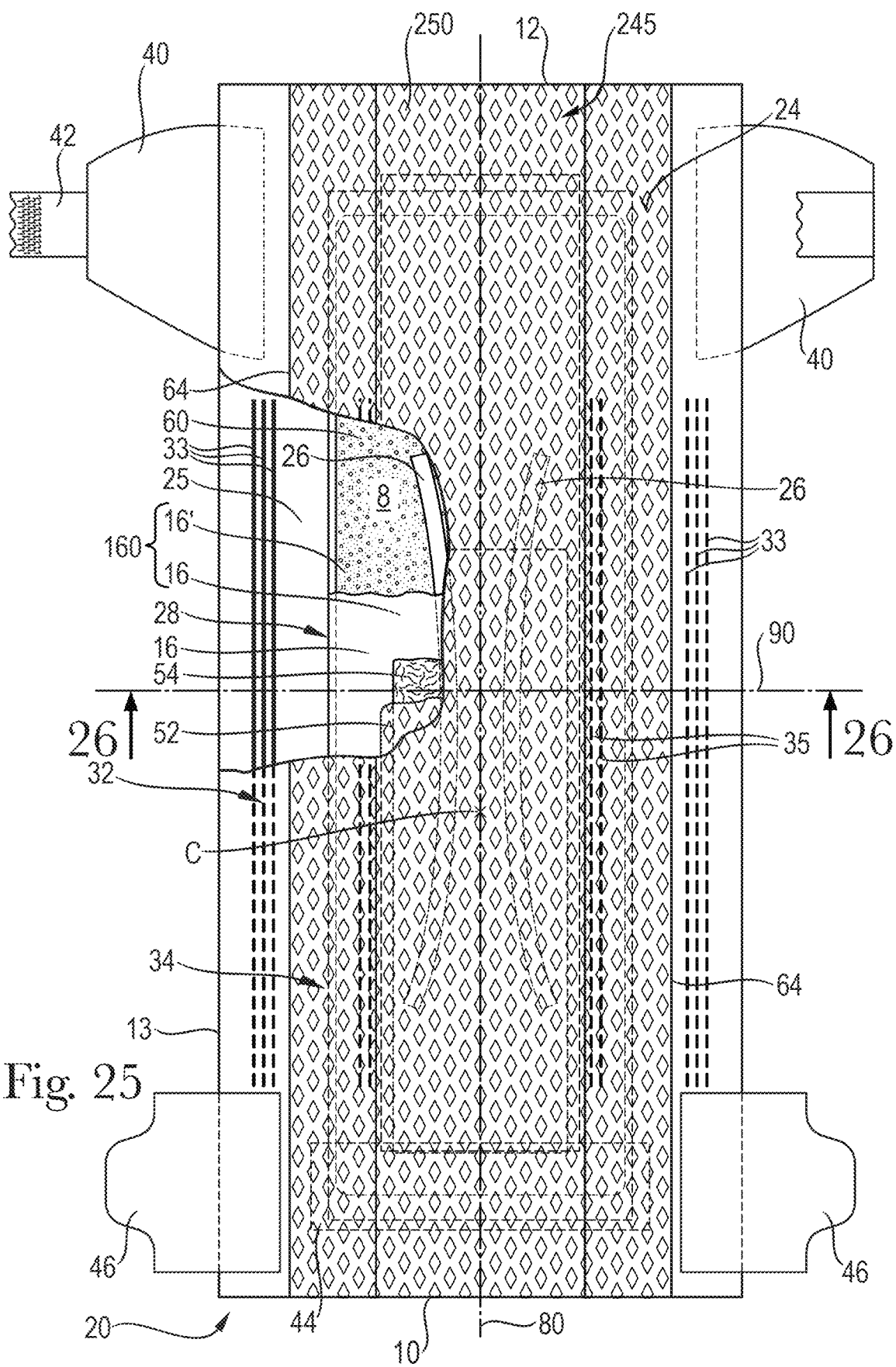
FIG. 25 is an absorbent article in the form of a diaper comprising an example topsheet/acquisition layer composite structure where the length of the acquisition layer is less that the length of the topsheet with some layers partially removed in accordance with the present disclosure.
Figure 26:
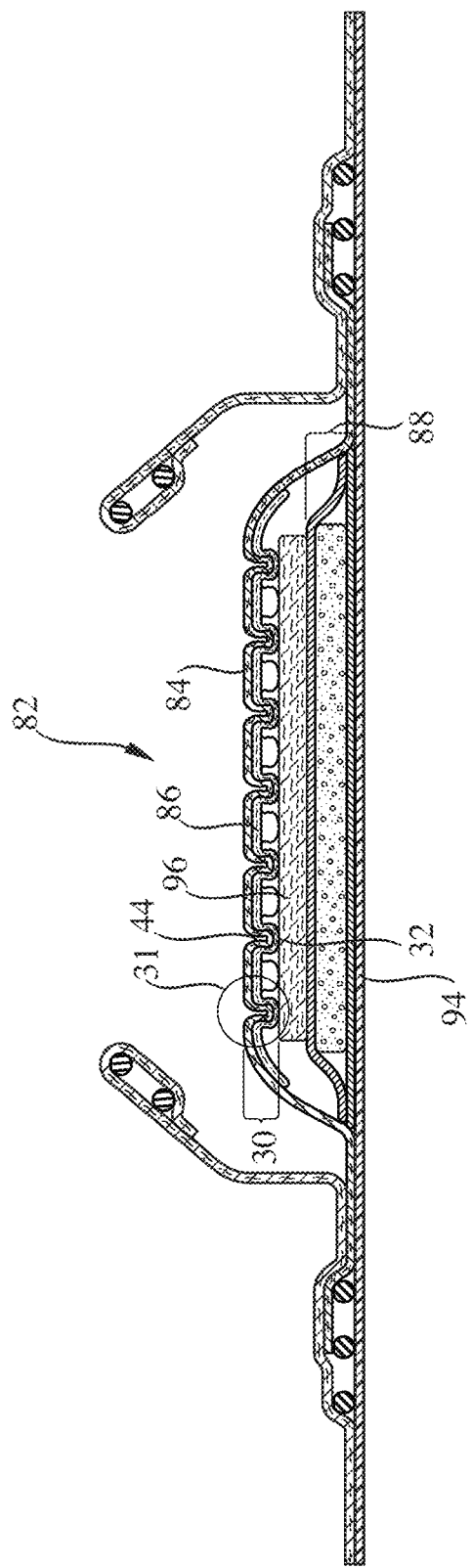
FIG. 26 is one transverse cross-section of the diaper of FIG. 25 taken along line 26-26 in accordance with the present disclosure.
Figure 27:
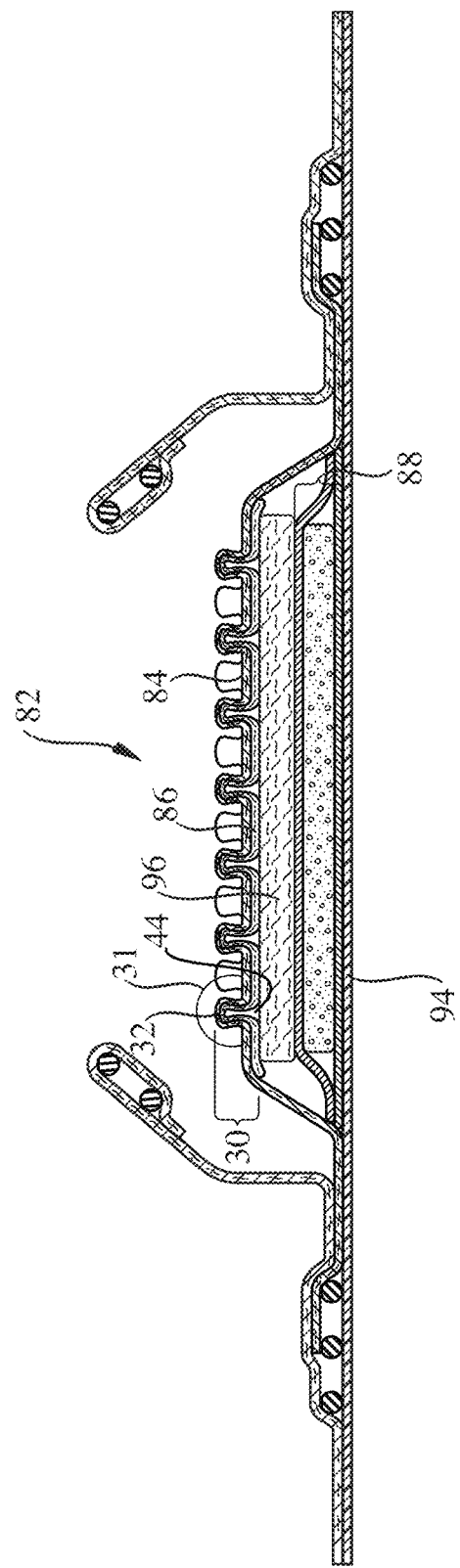
FIG. 27 is an alternative transverse cross-section of the diaper of FIG. 25 in accordance with the present disclosure.

The nonwoven webs or three-dimensional materials 30 described herein can comprise any suitable component or components of an absorbent article. For example, the nonwoven webs can comprise a topsheet of an absorbent article or, as shown in FIG. 25, if the nonwoven web 30 comprises more than one layer, the nonwoven web can comprise a combined topsheet 84 and acquisition layer 86 of an absorbent article, such as diaper 82, for example. The diaper 82 shown in FIGS. 25-27 also comprises an absorbent core 88, a backsheet 94, and a distribution material 96. The nonwoven webs or materials of the present disclosure may also form an outer cover of an absorbent article, such as an outer cover nonwoven material 223 (see FIG. 29). The nonwoven webs 30 can be placed in an absorbent article with the deformations 31 in any suitable orientation. For example, the protrusions 32 may be oriented up or down. In other words, the protrusions 32 may be oriented toward the absorbent core 88 as shown in FIG. 26. Thus, for example, it may be desirable for the protrusions 32 to point inward toward the absorbent core 88 in a diaper (that is, away from the wearer-facing side and toward the garment-facing side), or other absorbent article. Alternatively, the protrusions 32 may be oriented so that they extend away from the absorbent core of the absorbent article as shown in FIG. 27. In still other forms, the nonwoven webs 30 can be made so that they have some protrusions 32 that are oriented upward, and some protrusions 32 that are oriented downward. Without wishing to be bound to any particular theory, it is believed that such a structure may be useful in that the protrusions that are oriented upward may be more effective for cleaning the body from bodily exudates, while the protrusions that are oriented downward can be more effective for absorption of bodily exudates into the absorbent core. Therefore, without being bound to theory, a combination of these two protrusion orientations may offer an advantage that the same product may fulfill the two functions.

A two or more layer nonwoven structure may provide fluid handling benefits. If the layers are integrated together, and the protrusions 32 are oriented toward the absorbent core, they may also provide a dryness benefit. It may be desirable, on the other hand, for the protrusions 32 to point outward, away from the absorbent core in a pad for a wet or dry mop to provide a cleaning benefit. In some forms, when the nonwoven web 30 is incorporated into an absorbent article, the underlying layers can be either substantially, or completely free, of tow fibers. Suitable underlying layers that are free of tow fibers may, for example, comprise a layer or patch of cross-linked cellulose fibers. In some cases, it may be desirable that the nonwoven material 30 is not entangled with (that is, is free from entanglement with) another web.

The layers of the nonwoven structure (e.g., a topsheet and/or acquisition layer) may be colored. Color may be imparted to the webs by color pigmentation. The term "color pigmentation" encompasses any pigments suitable for imparting a non-white color to a web. This term therefore does not include "white" pigments such as $TiO_2$ which are typically added to the layers of conventional absorbent articles to impart them with a white appearance. Pigments are usually dispersed in vehicles or substrates for application, as for instance in inks, paints, plastics or other polymeric materials. The pigments may for example be introduced in a polypropylene masterbatch. A masterbatch comprises a high concentration of pigment and/or additives which are dispersed in a carrier medium which can then be used to pigment or modify the virgin polymer material into a pigmented bicomponent nonwoven. An example of suitable colored masterbatch material that can be introduced is Pantone color 270 Sanylen violet PP 42000634 ex Clariant, which is a PP resin with a high concentration of violet pigment. Typically, the amount of pigments introduced by weight of the webs may be of from 0.3%-2.5%. Alternatively, color may be imparted to the webs by way of impregnation of a colorant into the substrate. Colorants such as dyes, pigments, or combinations may be impregnated in the formation of substrates such as polymers, resins, or nonwovens. For example, the colorant may be added to molten batch of polymer during fiber or filament formation.

Precursor Materials

The nonwoven materials of the present disclosure can be made of any suitable nonwoven materials ("precursor materials"). The nonwoven webs can be made from a single layer, or multiple layers (e.g., two or more layers). If multiple layers are used, they can be comprised of the same type of nonwoven material, or different types of nonwoven materials. In some cases, the precursor materials may be free of any film layers.

The fibers of the nonwoven precursor material(s) can be made of any suitable materials including, but not limited to natural materials, synthetic materials, and combinations thereof. Suitable natural materials include, but are not limited to cellulose, cotton linters, bagasse, wool fibers, silk fibers, etc. Cellulose fibers can be provided in any suitable form, including but not limited to individual fibers, fluff pulp, drylap, liner board, etc. Suitable synthetic materials include, but are not limited to nylon, rayon and polymeric materials. Suitable polymeric materials include, but are not limited to: polyethylene (PE), polyester, polyethylene terephthalate (PET), polypropylene (PP), and co-polyester. In some forms, however, the nonwoven precursor materials can be either substantially, or completely free, of one or more of these materials. For example, in some forms, the precursor materials may be substantially free of cellulose, and/or exclude paper materials. In some forms, one or more precursor materials can comprise up to 100% thermoplastic fibers. The fibers in some cases may, therefore, be substantially non-absorbent. In some forms, the nonwoven precursor materials can be either substantially, or completely free, of tow fibers.

The precursor nonwoven materials can comprise any suitable types of fibers. Suitable types of fibers include, but are not limited to: monocomponent, bicomponent, and/or biconstituent, non-round (e.g., shaped fibers (including but not limited to fibers having a trilobal cross-section) and capillary channel fibers). The fibers can be of any suitable size. The fibers may, for example, have major cross-sectional dimensions (e.g., diameter for round fibers) ranging from 0.1-500 microns. Fiber size can also be expressed in denier, which is a unit of weight per length of fiber. The constituent fibers may, for example, range from about 0.1 denier to about 100 denier. The constituent fibers of the nonwoven precursor web(s) may also be a mixture of different fiber types, differing in such features as chemistry (e.g., PE and PP), components (mono- and bi-), shape (i.e. capillary channel and round) and the like.

The nonwoven precursor webs can be formed from many processes, such as, for example, air laying processes, wetlaid processes, meltblowing processes, spunbonding processes, and carding processes. The fibers in the webs can then be bonded via spunlacing processes, hydroentangling, calendar bonding, through-air bonding and resin bonding. Some of such individual nonwoven webs may have bond sites where the fibers are bonded together.

The basis weight of nonwoven materials is usually expressed in grams per square meter (gsm). The basis weight of a single layer nonwoven material can range from about 8 gsm to about 100 gsm, depending on the ultimate use of the material 30. For example, the topsheet of a topsheet/acquisition layer laminate or composite may have a basis weight from about 8 to about 40 gsm or from about 8 to about 30 gsm, or from about 8 to about 20 gsm. The acquisition layer may have a basis weight from about 10 to about 120 gsm or from about 10 to about 100 gsm, or from about 10 to about 80 gsm. The basis weight of a multilayer material is the combined basis weight of the constituent layers and any other added components. The basis weight of multilayer materials of interest herein can range from about 20 gsm to about 150 gsm, depending on the ultimate use of the material 30. The nonwoven precursor webs may have a density that is between about 0.01 and about 0.4 g/cm$^3$ measured at 0.3 psi (2 KPa).

The precursor nonwoven webs may have certain desired characteristics. The precursor nonwoven web(s) each have a first surface, a second surface, and a thickness. The first and second surfaces of the precursor nonwoven web(s) may be generally planar. It is typically desirable for the precursor nonwoven web materials to have extensibility to enable the fibers to stretch and/or rearrange into the form of the protrusions. If the nonwoven webs are comprised of two or more layers, it is desirable for all of the layers to be as extensible as possible. Extensibility is desirable in order to maintain at least some non-broken fibers in the sidewalls around the perimeter of the protrusions. It may be desirable for individual precursor webs, or at least one of the nonwovens within a multilayer structure, to be capable of undergoing an elongation of greater than or equal to about one of the following amounts: 100% (that is double its unstretched length), 110%, 120%, or 130% up to about 200%, or more, at or before reaching the peak tensile force. It is also desirable for the precursor nonwoven webs to be capable of undergoing plastic deformation to ensure that the structure of the deformations is "set" in place so that the nonwoven web will not tend to recover or return to its prior configuration.

Figure 20:
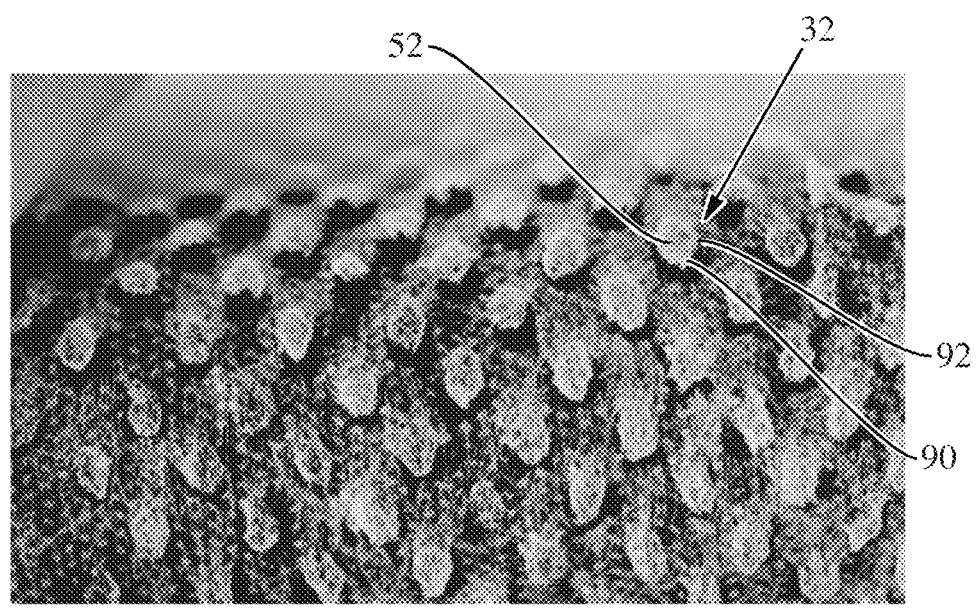
FIG. 20 is a perspective view photomicrograph of one layer of a multiple layer nonwoven material on the surface of a forming roll showing the "hanging chads" that can be formed in one of the layers when some nonwoven precursor web materials are used in accordance with the present disclosure.

Materials that are not extensible enough (e.g., inextensible PP) may form broken fibers around much of the perimeter of the deformation, and create more of a "hanging chad" 90 (i.e., the cap 52 of the protrusions 32 may be at least partially broken from and separated from the rest of the protrusion (as shown in FIG. 20). The area on the sides of the protrusion where the fibers are broken is designated with reference number 92. Materials such as that shown in FIG. 20 will not be suitable for a single layer structure, and, if used, will typically be part of a composite multilayer structure in which another layer has protrusions 32 as described herein.

When the fibers of a nonwoven web are not very extensible, it may be desirable for the nonwoven to be underbonded as opposed to optimally bonded. A thermally bonded nonwoven web's tensile properties can be modified by changing the bonding temperature. A web can be optimally or ideally bonded, underbonded or overbonded. Optimally or ideally bonded webs are characterized by the highest peak tensile strength and elongation at tensile peak with a rapid decay in strength after tensile peak. Under strain, bond sites fail and a small amount of fibers pull out of the bond site. Thus, in an optimally bonded nonwoven, the fibers 38 will stretch and break around the bond sites 46 when the nonwoven web is strained beyond a certain point. Often there is a small reduction in fiber diameter in the area surrounding the thermal point bond sites. Underbonded webs have a lower peak tensile strength and elongation at tensile peak when compared to optimally bonded webs, with a slow decay in strength after tensile peak. Under strain, some fibers will pull out from the thermal point bond sites. Thus, in an underbonded nonwoven, at least some of the fibers 38 can be separated easily from the bond sites 46 to allow the fibers 38 to pull out of the bond sites and rearrange when the material is strained. Overbonded webs also have a lowered peak tensile strength and elongation at tensile peak when compared to optimally bonded webs, with a rapid decay in strength after tensile peak. The bond sites look like films and result in complete bond site failure under strain.

When the nonwoven web comprises two or more layers, the different layers can have the same properties, or any suitable differences in properties relative to each other. In a form, the nonwoven web 30 can comprise a two layer structure that is used in an absorbent article. For convenience, the precursor webs and the material into which they are formed are referred to herein by the same reference numbers. One of the layers, a second layer 30B, can serve as the topsheet of the absorbent article, and the first layer 30A can be an underlying layer (or sub-layer) and serve as an acquisition layer. The acquisition layer 30A receives liquids that pass through the topsheet and distributes them to underlying absorbent layers. In such a case, the topsheet 30B may be less hydrophilic than sub-layer(s) 30A, which may lead to better dewatering of the topsheet. In other forms, the topsheet can be more hydrophilic than the sub-layer(s). In some cases, the pore size of the acquisition layer may be reduced, for example via using fibers with smaller denier or via increasing the density of the acquisition layer material, to better dewater the pores of the topsheet.

The second nonwoven layer 30B that may serve as the topsheet can have any suitable properties. Properties of interest for the second nonwoven layer, when it serves as a topsheet, in addition to sufficient extensibility and plastic deformation may include uniformity and opacity. As used herein, "uniformity" refers to the macroscopic variability in basis weight of a nonwoven web. As used, herein, "opacity" of nonwoven webs is a measure of the impenetrability of visual light, and is used as visual determination of the relative fiber density on a macroscopic scale. As used herein, "opacity" of the different regions of a single nonwoven deformation is determined by taking a photomicrograph at 20× magnification of the portion of the nonwoven containing the deformation against a black background. Darker areas indicate relatively lower opacity (as well as lower basis weight and lower density) than white areas.

Several examples of nonwoven materials suitable for use as the second nonwoven layer 30B include, but are not limited to: spunbonded nonwovens; carded nonwovens; and other nonwovens with high extensibility (strain at peak tensile strength in the ranges set forth above) and sufficient plastic deformation to ensure the structure is set and does not have significant recovery. One suitable nonwoven material as a topsheet for a topsheet/acquisition layer composite structure may be an extensible spunbonded nonwoven comprising polypropylene and polyethylene. The fibers can comprise a blend of polypropylene and polyethylene, or they can be bi-component fibers, such as a sheath-core fiber with polyethylene on the sheath and polypropylene in the core of the fiber. Another suitable material is a bi-component fiber spunbonded nonwoven comprising fibers with a polyethylene sheath and a polyethylene/polypropylene blend core.

The first nonwoven layer 30A that may, for example, serve as the acquisition layer can have any suitable properties. Properties of interest for the first nonwoven layer, in addition to sufficient extensibility and plastic deformation may include uniformity and opacity. If the first nonwoven layer 30A serves as an acquisition layer, its fluid handling properties must also be appropriate for this purpose. Such properties may include: permeability, porosity, capillary pressure, caliper, as well as mechanical properties such as sufficient resistance to compression and resiliency to maintain void volume. Suitable nonwoven materials for the first nonwoven layer when it serves as an acquisition layer include, but are not limited to: spunbonded nonwovens; through-air bonded ("TAB") carded nonwoven materials; spunlace nonwovens; hydroentangled nonwovens; and, resin bonded carded nonwoven materials. Of course, the composite structure may be inverted and incorporated into an article in which the first layer 30A serves as the topsheet and the second layer 30B serves as an acquisition layer. In such cases, the properties and exemplary methods of the first and second layers described herein may be interchanged.

The layers of a two or more layered nonwoven web structure can be combined together in any suitable manner. In some cases, the layers can be unbonded to each other and held together autogenously (that is, by virtue of the formation of deformations therein). For example, both precursor webs 30A and 30B contribute fibers to deformations in a "nested" relationship that "locks" the two precursor webs together, forming a multilayer web without the use or need for adhesives or thermal bonding between the layers. In other forms, the layers can be joined together by other mechanisms. If desired an adhesive between the layers, ultrasonic bonding, chemical bonding, resin or powder bonding, thermal bonding, or bonding at discrete sites using a combination of heat and pressure can be selectively utilized to bond certain regions or all of the precursor webs. If adhesives are used, they can be applied in any suitable manner or pattern including, but not limited to: slots, spirals, spray, and curtain coating. Adhesives can be applied in any suitable amount or basis weight including, but not limited to between about 0.5 and about 30 gsm, alternatively between about 2 and about 5 gsm. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together.

Figure 24:
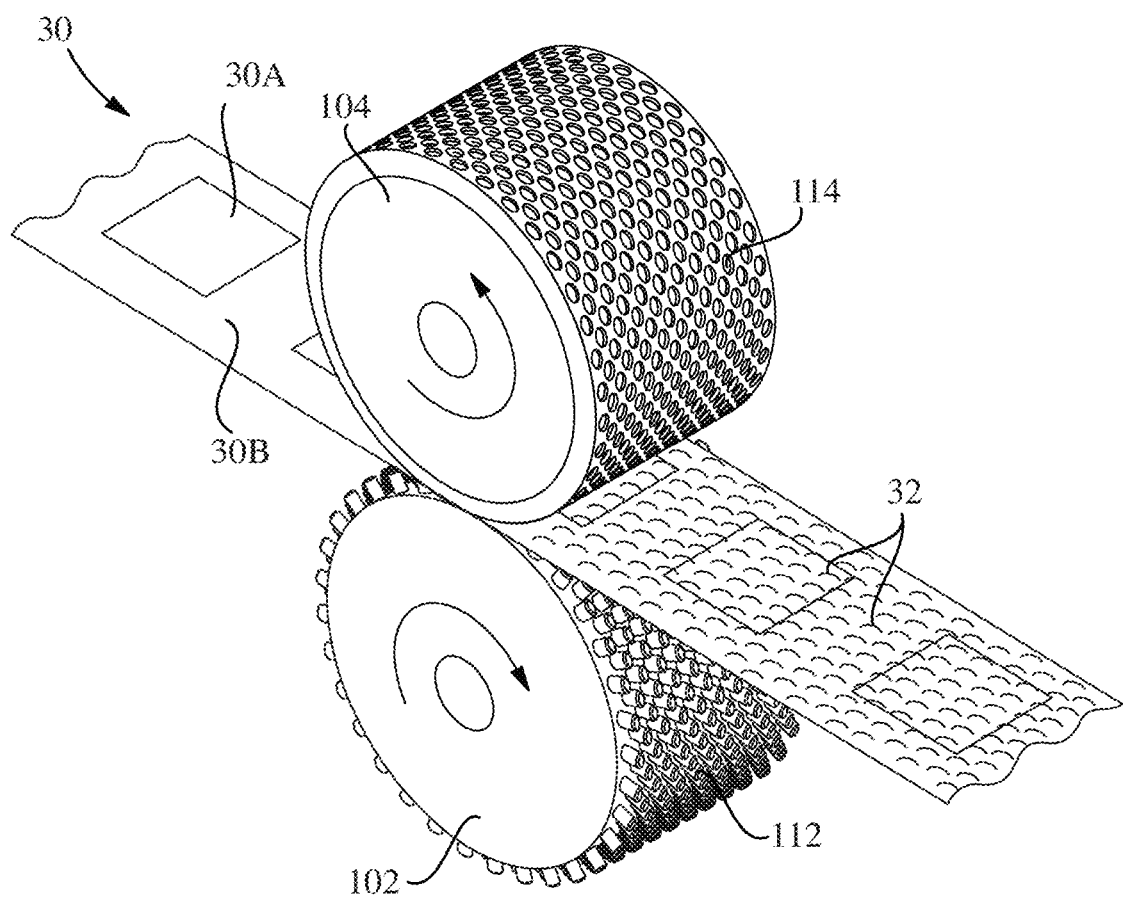
FIG. 24 is a schematic perspective view of one version of a method of making nonwoven materials having deformations therein where two precursor materials are used, one of which is a continuous web and the other of which is in the form of discrete pieces in accordance with the present disclosure.

When the precursor nonwoven web comprises two or more layers, it may be desirable for at least one of the layers to be continuous, such as in the form of a web that is unwound from a roll. In some forms, each of the layers can be continuous. In alternative forms, such as shown in FIG. 24, one or more of the layers can be continuous, and one or more of the layers can have a discrete length. The layers may also have different widths. For example, in making a combined topsheet and acquisition layer for an absorbent article, the nonwoven layer that will serve as the topsheet may be a continuous web, and the nonwoven layer that will serve as the acquisition layer may be fed into the manufacturing line in the form of discrete length (for example, rectangular, or other shaped) pieces that are placed on top of the continuous web. Such an acquisition layer may, for example, have a lesser width than the topsheet layer. The layers may be combined together as described above.

Methods of Making the Nonwoven Materials

The nonwoven materials are made by a method comprising the steps of: a) providing at least one precursor nonwoven web; b) providing an apparatus comprising a pair of forming members comprising a first forming member and a second forming member; and c) placing the precursor nonwoven web(s) between the forming members and mechanically deforming the precursor nonwoven web(s) with the forming members. The forming members have a machine direction (MD) orientation and a cross-machine direction (CD) orientation.

The first and second forming members can be plates, rolls, belts, or any other suitable types of forming members. In some forms, it may be desirable to modify the apparatus for incrementally stretching a web described in U.S. Pat. No. 8,021,591, Curro, et al. entitled "Method and Apparatus for Incrementally Stretching a Web" by providing the activation members described therein with the forming elements of the type described herein. In the form of the apparatus 100 shown in FIG. 21, the first and second forming members 102 and 104 are in the form of non-deformable, meshing, counter-rotating rolls that form a nip 106 therebetween. The precursor web(s) is/are fed into the nip 106 between the rolls 102 and 104. Although the space between the rolls 102 and 104 is described herein as a nip, as discussed in greater detail below, in some cases, it may be desirable to avoid compressing the precursor web(s) to the extent possible.

First Forming Member.

The first forming member 102 has a surface comprising a plurality of first forming elements which comprise discrete, spaced apart male forming elements 112. The male forming elements are spaced apart in the machine direction and in the cross-machine direction. The term "discrete" does not include continuous or non-discrete forming elements such as the ridges and grooves on corrugated rolls (or "ring rolls") which have ridges that may be spaced apart in one, but not both, of the machine direction and in the cross-machine direction.

Figure 21:
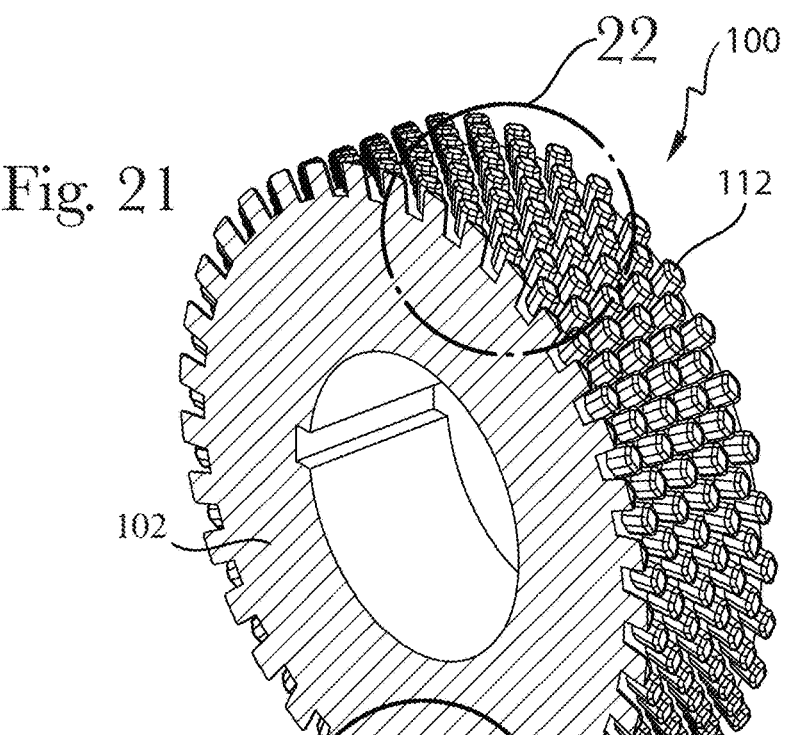
FIG. 21 is a perspective view of one example of an apparatus for forming the nonwoven materials described herein in accordance with the present disclosure.
Figure 22:
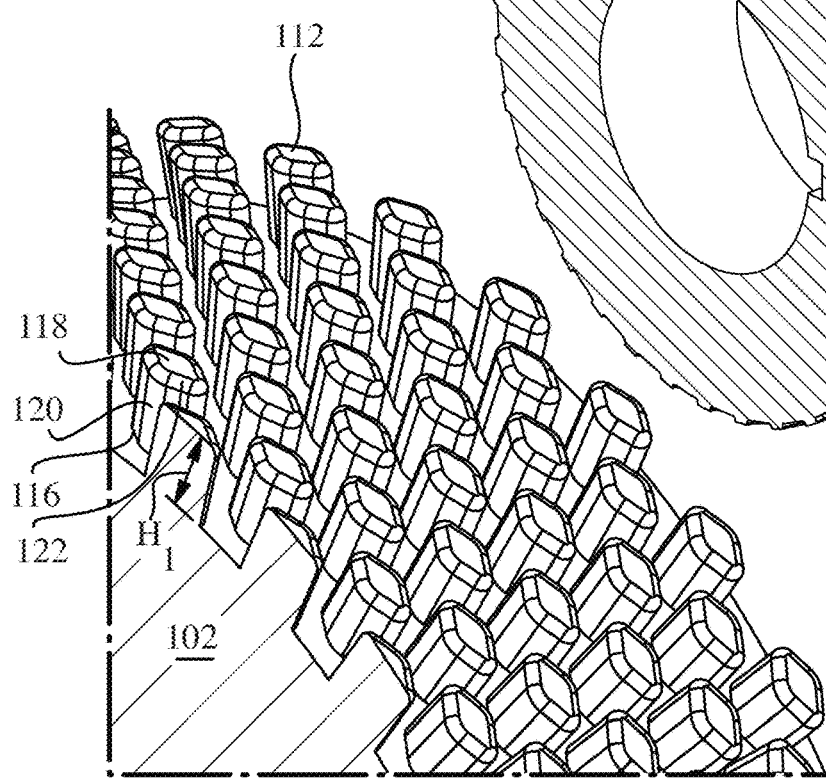
FIG. 22 is an enlarged perspective view of a portion of the male roll shown in FIG. 21 in accordance with the present disclosure.

As shown in FIG. 22, the male forming elements 112 have a base 116 that is joined to (in this case is integral with) the first forming member 102, a top 118 that is spaced away from the base, and sides 120 that extend between the base and the top of the male forming elements. The male elements 112 also have a plan view periphery, and a height $H_1$ (the latter being measured from the base 116 to the top 118). The discrete elements on the male roll have a top 118 with a relatively large surface area (e.g., from about 1 mm to about 10 mm in width, and from about 1 mm to about 20 mm in length) for creating a wide deformation. The male elements 112 may have any suitable configuration. In a form, the male elements 112 have a flat top 118, vertical sidewalls 120, a radiused edge forming the transition 122 between the flat top 118 and vertical sidewalls 120 (by vertical side walls, it is meant that the side walls 120 have zero degree side wall angles relative to the perpendicular from the base of the side wall). The top 118 of the male elements 112 may have any suitable plan view configuration, including but not limited to: a rounded diamond configuration as shown in FIGS. 21 and 22, and an American football-like shape, triangle, clover, teardrop, oval, elliptical.

Numerous other forms of the male forming elements 112 are possible. In other forms, the top 118 of the male forming elements 112 can be rounded. In other forms, the side walls 120 can be tapered inwardly toward the center of the male forming elements 112 so that the side walls form an angle greater than zero. In other forms, the top 118 of the male elements 112 can be of different shapes from those shown in the drawings. In other forms, the male forming elements 112 can be disposed in other orientations on the first forming member 102 rather than having their length oriented in the machine direction (including CD-orientations, and orientations between the MD and CD).

Second Forming Member.

As shown in FIG. 21, the second forming member 104 has a surface 124 having a plurality of cavities or recesses 114 therein. The recesses 114 are aligned and configured to receive the male forming elements 112 therein. Thus, the male forming elements 112 mate with the recesses 114 so that a single male forming element 112 fits within the periphery of a single recess 114, and at least partially within the recess 114 in the z-direction. The recesses 114 have a plan view periphery 126 that is larger than the plan view periphery of the male elements 112. As a result, the recess 114 on the female roll completely encompasses the discrete male element 112 when the rolls 102 and 104 are intermeshed. The recesses 114 have a depth $D_1$ shown in FIG. 23. In some cases, the depth $D_1$ of the recesses may be greater than the height $H_1$ of the male forming elements 112.

The recesses 114 may have a similar plan view configuration as the male elements 112, side walls 128, and an edge 130 around the bottom 132 of the recesses where the side walls 128 meet the bottom 132 of the recesses. The side walls 128 of the recesses 114 may be vertical. The edge 130 of the recesses may be sharp or rounded.

As discussed above, the recesses 114 may be deeper than the height $H_1$ of the male elements 112 so the nonwoven material is not nipped (or squeezed) between the male and female rolls 102 and 104 to the extent possible. However, it is understood that passing the precursor web(s) between two rolls with a relatively small space therebetween will likely apply some shear and compressive forces to the web(s). The present method, however, differs from some embossing processes in which the top of the male elements compress the material to be embossed against the bottom of the female elements, thereby increasing the density of the region in which the material is compressed.

Figure 23:
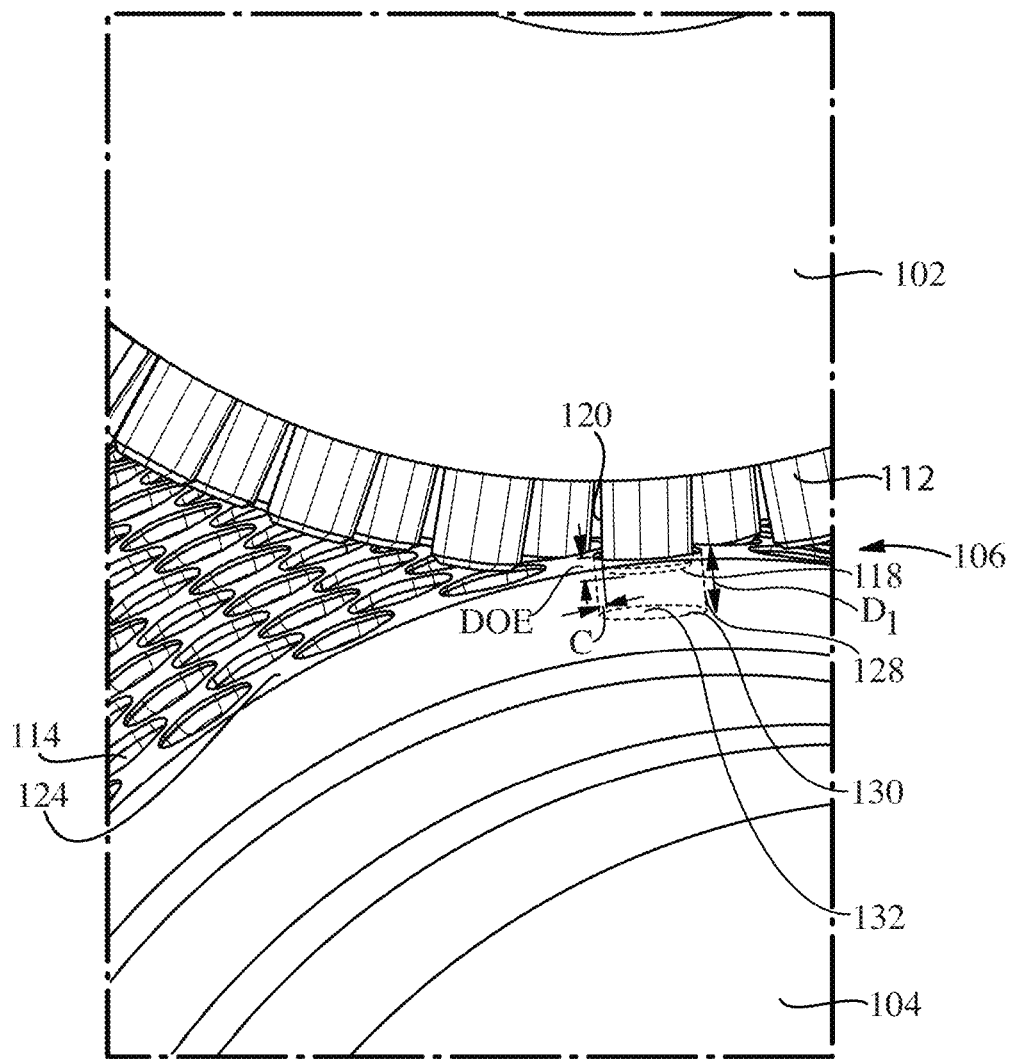
FIG. 23 is an enlarged perspective view showing the nip between the rolls shown in FIG. 21 in accordance with the present disclosure.

The depth of engagement (DOE) is a measure of the level of intermeshing of the forming members. As shown in FIG. 23, the DOE is measured from the top 118 of the male elements 112 to the outermost surface 124 of the female forming member 114 (e.g., the roll with recesses). The DOE should be sufficiently high, when combined with extensible nonwoven materials, to create protrusions 32 having a distal portion or cap 52 with a maximum width that is greater than the width of the base opening 44. The DOE may, for example, range from at least about 1.5 mm, or less, to about 5 mm, or more. In certain forms, the DOE may be between about 2.5 mm to about 5 mm, alternatively between about 3 mm and about 4 mm. The formation of protrusions 32 having a distal portion with a maximum width that is greater than the width of the base opening 44 is believed to differ from most embossing processes in which the embossments typically take the configuration of the embossing elements, which have a base opening that is wider than the remainder of the embossments. As shown in FIG. 23, there is a clearance, C, between the sides 120 of the male elements 112 and the sides (or side walls) 128 of the recesses 114. The clearance, C, between the male and female roll may be the same, or it may vary slightly around the perimeter of the male element. Clearances can range from about 0.005 inches (0.13 mm) to about 0.05 inches (1.3 mm). The clearances and the DOE's are related such that larger clearances can permit higher DOE's to be used.

The precursor nonwoven web is placed between the forming members 102 and 104. The precursor nonwoven web can be placed between the forming members with either side of the precursor web (first surface 34 or second surface 36) facing the first forming member, male forming member 102. For convenience of description, the second surface 36 of the precursor nonwoven web will be described herein as being placed in contact with the first forming member 102. (Of course, in other forms, the second surface 36 of the precursor nonwoven web can be placed in contact with the second forming member 104.) The precursor material is mechanically deformed with the forming members 102 and 104 when a force is applied on the nonwoven web with the forming members 102 and 104. The force can be applied in any suitable manner. If the forming members 102 and 104 are in the form of plates, the force will be applied when the plates are brought together. If the forming members 102 and 104 are in the form of counter-rotating rolls (or belts, or any combination of rolls and belts), the force will be applied when the precursor nonwoven web passes through the nip between the counter-rotating elements. The force applied by the forming members impacts the precursor web and mechanically deforms the precursor nonwoven web.

When deforming multiple webs that are laminated together with an adhesive, it may be desirable to chill the forming members in order to avoid glue sticking to and fouling the forming members. The forming members can be chilled using processes know in the art. One such process could be an industrial chiller that utilizes a coolant, such as propylene glycol. In some cases, it may be desirable to operate the process in a humid environment such that a layer of condensate forms on the forming members.

The precursor nonwoven web forms nonwoven web comprising a generally planar first region and a plurality of discrete integral second regions that comprise deformations comprising protrusions extending outward from the first surface 34 of the nonwoven web and openings in the second surface of the nonwoven web. (Of course, if the second surface 36 of the precursor nonwoven web is placed in contact with the second forming member 104, the protrusions will extend outward from the second surface of the nonwoven web and the openings will be formed in the first surface of the nonwoven web.) Without wishing to be bound by any particular theory, it is believed that the extensibility of the precursor web (or at least one of the layers of the same) when pushed by the male forming elements 112 into the recesses 114 with depth of engagement DOE being less than the depth $D_1$ of the recesses, stretches a portion of the nonwoven web to form a deformation comprising a protrusion with the enlarged cap and wide base opening described above. (This can be analogized to sticking one's finger into an uninflated balloon to stretch and permanently deform the material of the balloon.)

In cases in which the precursor nonwoven material 30 comprises more than one layer, and one of the layers is in the form of discrete pieces of nonwoven material, as shown in FIG. 24, it may be desirable for the deformations to be formed so that the base openings are in the continuous layer (such as 30B) and the protrusions 32 extend toward the discrete layer (such as 30A). Of course, in other forms, the deformations in such a structure can be in the opposite orientation. The deformations can be distributed in any suitable manner over the surfaces of such continuous and discrete layers. For example, the deformations can: be distributed over the full length and/or width of the continuous layer; be distributed in an area narrower than the width of the continuous layer; or be limited to the area of the discrete layer.

The method of making the nonwoven materials described herein may exclude (or be distinguishable from) the following processes: hydroforming (hydroentangling); hydromolding; use of air jets; rigid-to-resilient (e.g., steel/rubber) embossing; and the use of a patterned surface against a flat anvil surface. The method may also exclude (or be distinguishable from) The Procter & Gamble Company's processes for making Structural Elastic-Like Films ("SELF" processes). The forming members used herein differ from the forming members used in SELFing processes to form corrugated structures (and tufted structures) in that the SELF teeth typically have a comparatively small diameter tip, and the ridges of the mating ring roll only border the SELF teeth on the sides, and not the front and back of the teeth.

Absorbent Articles

Three-dimensional nonwoven materials and the method of their manufacture of the present disclosure have been discussed above. The use of those three-dimensional nonwoven materials is now explained in further detail in the context of example absorbent articles. These absorbent articles may comprise various color and indicia designs and/or patterns. The absorbent articles may also comprise channels in one or more layers intermediate the topsheet and the absorbent core.

General Description of an Absorbent Article

Figure 28:
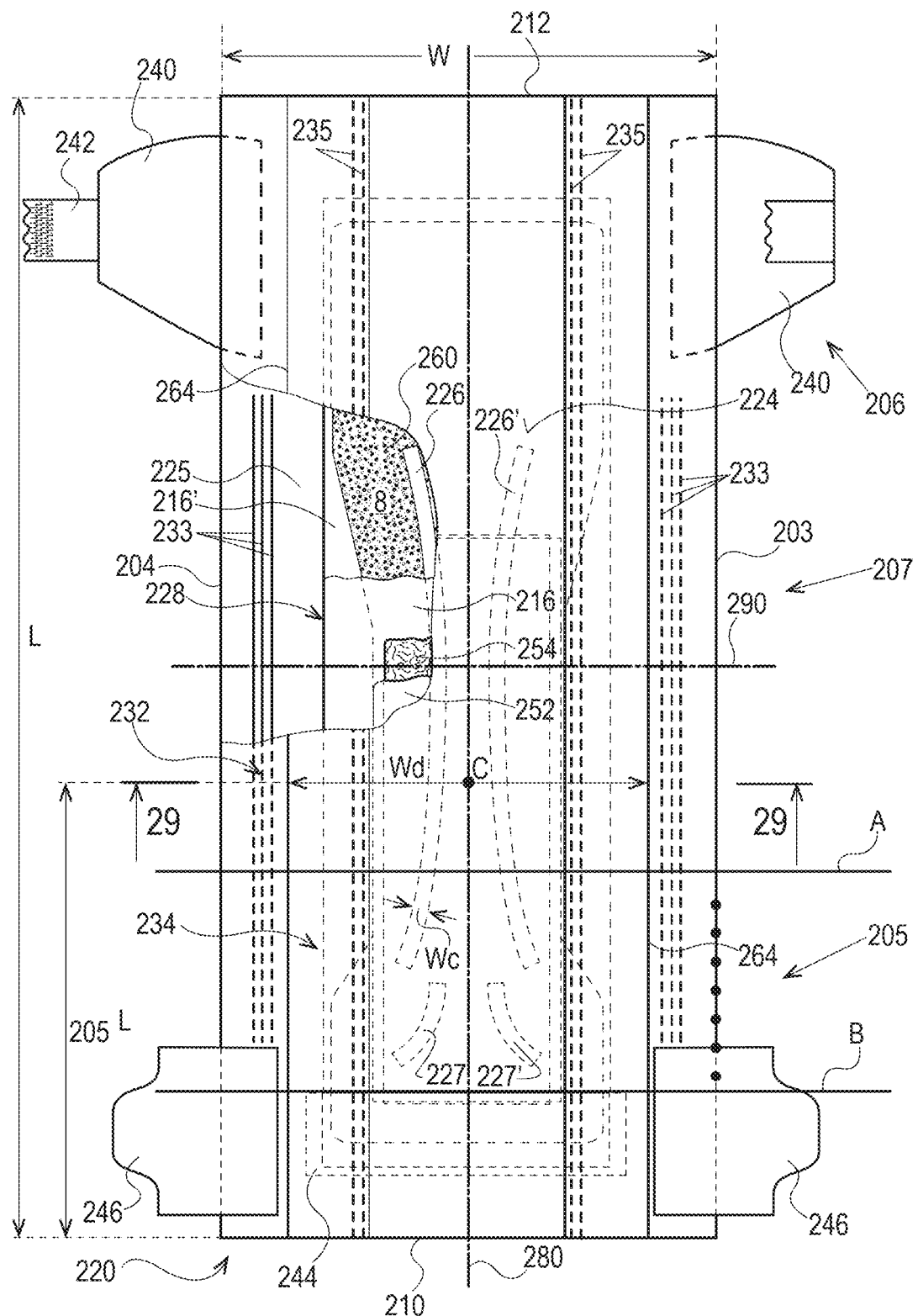
FIG. 28 is a top view of an example absorbent article, wearer-facing surface facing the viewer, with some layers partially removed in accordance with the present disclosure.
Figure 29:
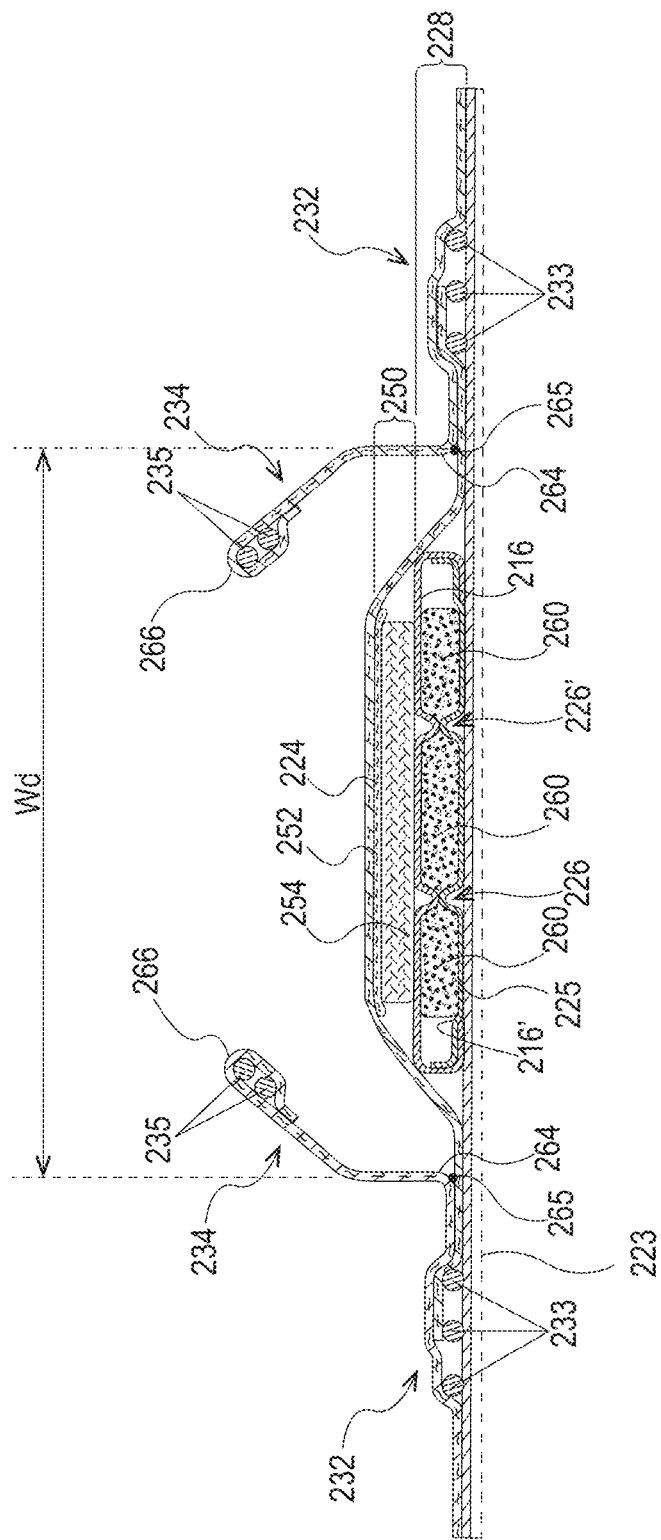
FIG. 29 is a cross-sectional view of the absorbent article taken about line 29-29 of FIG. 28 in accordance with the present disclosure.
Figure 30:
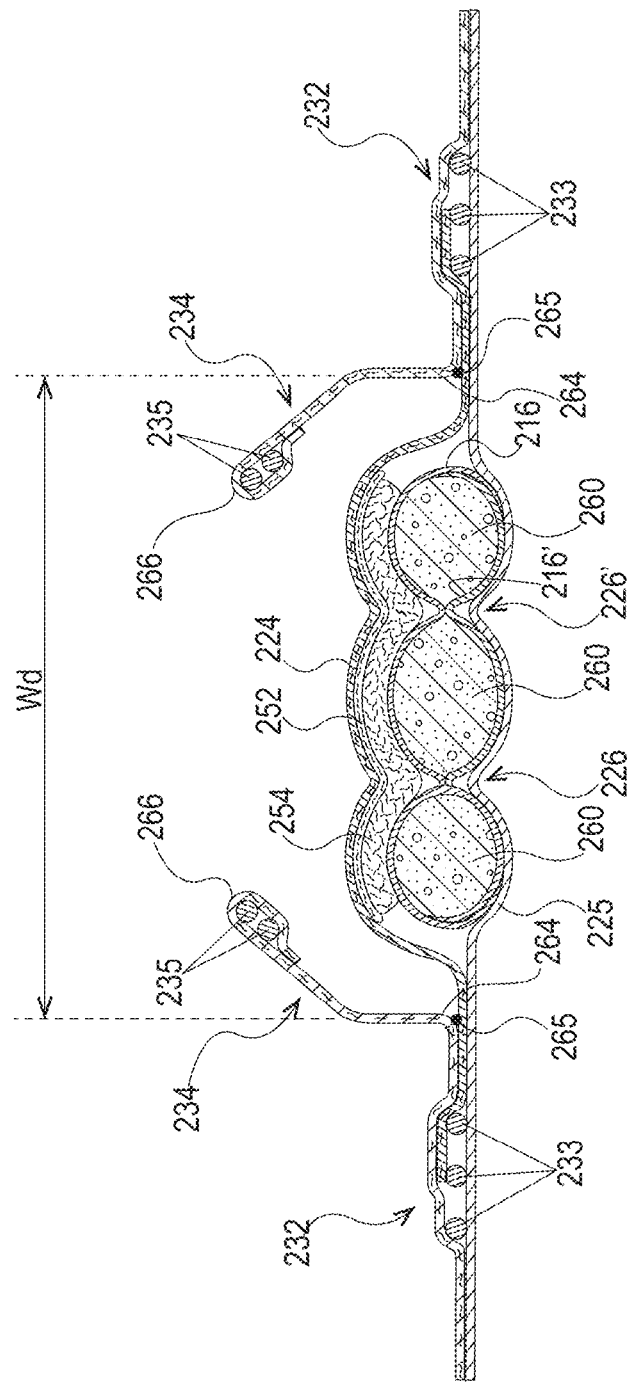
FIG. 30 is a cross-sectional view of the absorbent article taken about line 29-29 of FIG. 28 where the absorbent article has been loaded with fluid in accordance with the present disclosure.

An example absorbent article in the form of a diaper 220 is represented in FIGS. 28-30. FIG. 28 is a plan view of the example diaper 220, in a flat, laid-out state, with portions of the structure being cut-away to more clearly show the construction of the diaper 220. The wearer-facing surface of the diaper 220 of FIG. 28 is facing the viewer. This diaper 220 is shown for illustration purpose only as the three-dimensional nonwoven materials of the present disclosure may be used as one or more components of an absorbent article, such as the topsheet, the acquisition layer, the topsheet and the acquisition layer individually, or a laminate formed of the topsheet and the acquisition layer. In any event, the three-dimensional nonwoven materials of the present disclosure may be liquid permeable. Channels may be present in the absorbent core, the distribution material, and/or the carrier layer (if the carrier layer is provided). Channels may also be present in an acquisition layer if the acquisition layer is not combined with the topsheet. In some instances, a distribution material may not be provided, and the channels may only be in the acquisition layer or another layer intermediate the topsheet and the absorbent core. If channels are provided in more than one of these materials intermediate the topsheet and the absorbent core, the channels may fully overlap each other, partially overlap each other, or be free from any overlap with each other, all with respect to the Z-direction.

The absorbent article 220 may comprise a liquid permeable material or topsheet 224, a liquid impermeable material or backsheet 225, an absorbent core 228 positioned at least partially intermediate the topsheet 224 and the backsheet 225, and barrier leg cuffs 234. The absorbent article may also comprise an ADS, which in the example represented comprises a distribution material 254 and an acquisition layer 252, which will be further discussed below. The acquisition layer 252 may be nested with the topsheet as described herein, and illustrated in various figures. The absorbent article 220 may also comprise elasticized gasketing cuffs 232 comprising elastics 233 joined to a chassis of the absorbent article, typically via the topsheet and/or backsheet, and substantially planar with the chassis of the diaper.

Figure 31:
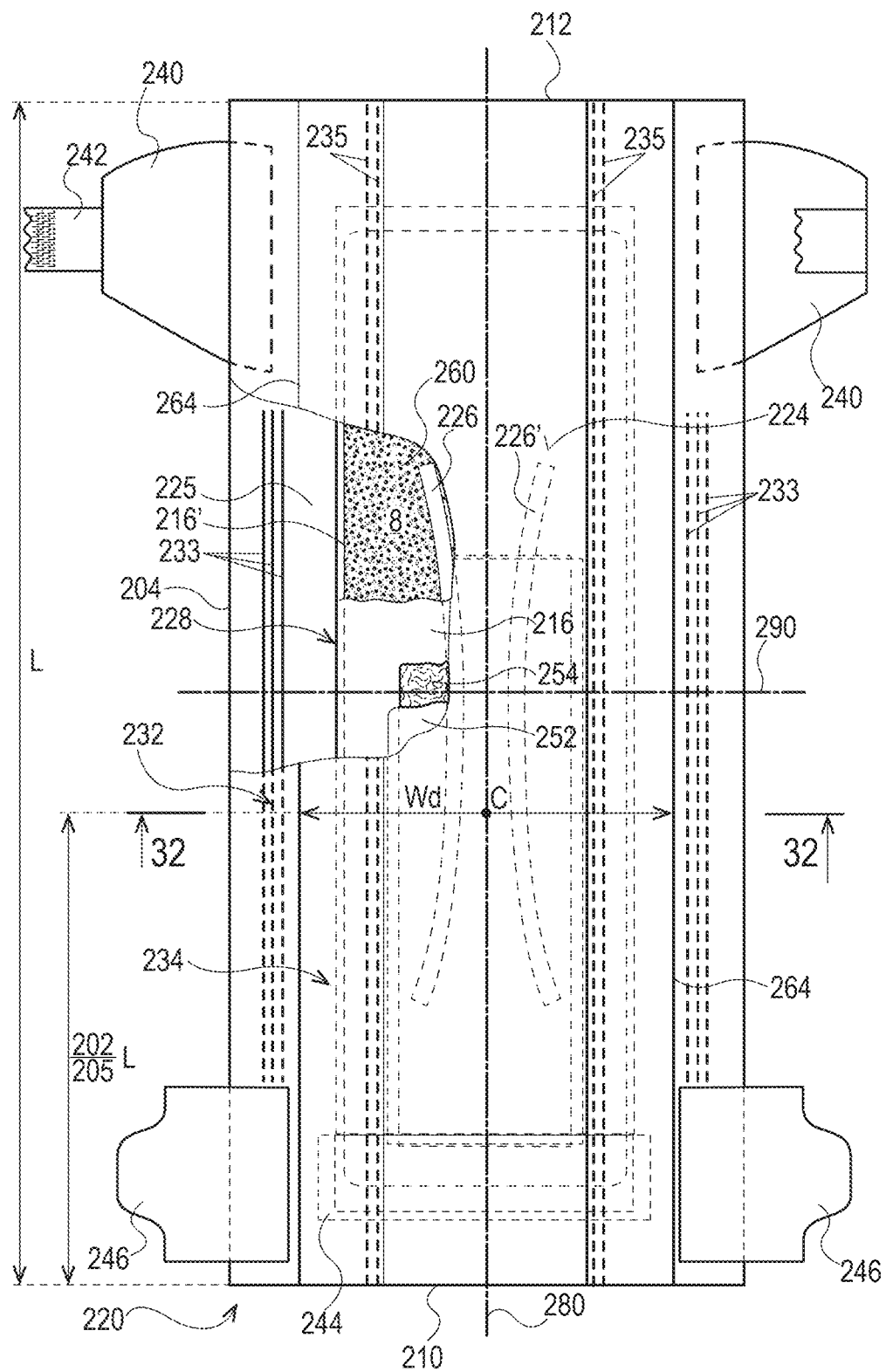
FIG. 31 is a top view of another absorbent article, wearer-facing surface facing the viewer, with some layers partially removed in accordance with the present disclosure.

FIGS. 28 and 31 also show typical taped diaper components such as a fastening system comprising tabs 242 attached towards the rear edge of the article and cooperating with a landing zone 244 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 220 comprises a front waist edge 210, a rear waist edge 212 longitudinally opposing the front waist edge 210, a first side edge 203, and a second side edge 204 laterally opposing the first side edge 203. The front waist edge 210 is the edge of the article which is intended to be placed towards the front of the user when worn, and the rear waist edge 212 is the opposite edge. The absorbent article 220 may have a longitudinal axis 280 extending from the lateral midpoint of the front waist edge 210 to a lateral midpoint of the rear waist edge 212 of the article and dividing the article in two substantially symmetrical halves relative to the longitudinal axis 280, with the article placed flat, laid-out and viewed from above as in FIG. 28. The absorbent article 220 may also have a lateral axis 290 extending from the longitudinal midpoint of the first side edge 203 to the longitudinal midpoint of the second side edge 204. The length, L, of the article may be measured along the longitudinal axis 280 from the front waist edge 210 to the rear waist edge 212. The width, W, of the absorbent article may be measured along the lateral axis 290 from the first side edge 203 to the second side edge 204. The absorbent article may comprise a crotch point C defined herein as the point placed on the longitudinal axis at a distance of two fifth (⅖) of L starting from the front edge 210 of the article 220. The article may comprise a front waist region 205, a rear waist region 206, and a crotch region 207. The front waist region 205, the rear waist region 206, and the crotch region 207 may each define ⅓ of the longitudinal length, L, of the absorbent article.

The topsheet 224, the backsheet 225, the absorbent core 228, and the other article components may be assembled in a variety of configurations, in particular by gluing or heat embossing, for example.

The absorbent core 228 may comprise an absorbent material comprising at least 80% by weight, at least 85% by weight, at least 90% by weight, at least 95% by weight, or at least 99% by weight of superabsorbent polymers, and a core wrap enclosing the superabsorbent polymers. The core wrap may typically comprise two materials, substrates, or nonwoven materials 216 and 216' for the top side and the bottom side of the core. These types of cores are known as airfelt-free cores. The core may comprise one or more channels, represented in FIG. 28 as the four channels 226, 226' and 227, 227'. The channels 226, 226', 227, and 227' are optional features. Instead, the core may not have any channels or may have any number of channels, such as two.

These and other components of the example absorbent articles will now be discussed in more details.

Topsheet

In the present disclosure, the topsheet (the portion of the absorbent article that contacts the wearer's skin and receives the fluids) may be formed of a portion of, or all of, one or more of the three-dimensional nonwoven materials described herein and/or have one or more of the nonwoven materials positioned thereon and/or joined thereto, so that the nonwoven material(s) contact(s) the wearer's skin. Other portions of the topsheet (other than the three-dimensional nonwoven materials) may also contact the wearer's skin. The three-dimensional nonwoven materials may be positioned as a strip or a patch on top of a typical topsheet. Alternatively, the three-dimensional nonwoven material may only form a central CD area of the topsheet. The central CD area may extend the full MD length of the topsheet or less than the full MD length of the topsheet. In some instances, the topsheet may be generally planar.

The topsheet 224 may be joined to the backsheet 225, the acquisition layer 252, the absorbent core 228 and/or any other layers as is known to those of skill in the art. Usually, the topsheet 224 and the backsheet 225 are joined directly to each other in some locations (e.g., on or close to the periphery of the absorbent article) and are indirectly joined together in other locations by directly joining them to one or more other elements of the article 220.

The topsheet 224 may be compliant, soft-feeling, and non-irritating to the wearer's skin. Further, a portion of, or all of, the topsheet 224 may be liquid permeable, permitting liquids to readily penetrate through its thickness. Any portion of the topsheet 224 may be coated with a lotion and/or a skin care composition as is generally disclosed in the art. The topsheet 224 may also comprise or be treated with antibacterial agents.

Backsheet

The backsheet 225 is generally that portion of the absorbent article 220 positioned adjacent the garment-facing surface of the absorbent core 228 and which prevents, or at least inhibits, the fluids and bodily exudates absorbed and contained therein from soiling articles such as bedsheets and undergarments. The backsheet 225 is typically impermeable, or at least substantially impermeable, to fluids (e.g., urine). The backsheet may, for example, be or comprise a thin plastic film such as a thermoplastic film having a thickness of about 0.012 mm to about 0.051 mm. Other suitable backsheet materials may include breathable materials which permit vapors to escape from the absorbent article 220, while still preventing, or at least inhibiting, fluids from passing through the backsheet 225.

The backsheet 225 may be joined to the topsheet 224, the absorbent core 228, and/or any other element of the absorbent article 220 by any attachment methods known to those of skill in the art.

An outer cover 223 of the absorbent article 220 may cover at least a portion of, or all of, the backsheet 225 to form a soft garment-facing surface of the absorbent article. The outer cover 223 may be formed of the high loft, three-dimensional nonwoven materials described herein. Alternatively, the outer cover 223 may comprise one or more known outer cover materials, such as conventional nonwoven materials. If the outer cover 223 comprises one or more of the three-dimensional nonwoven materials of the present disclosure, the three-dimensional nonwoven material of the outer cover 223 may or may not match (e.g., same material and/or same pattern, or similar material and/or similar pattern) a three-dimensional nonwoven material used as the topsheet, the acquisition layer, or a laminate of the topsheet and the acquisition layer of the absorbent article. In other instances, the outer cover 223 comprising one or more of the three-dimensional nonwoven materials may compliment or coordinate with one or more three-dimensional nonwoven materials used as the topsheet, the acquisition layer, or as a combined topsheet and acquisition layer. In other instances, the outer cover may have a printed or otherwise applied pattern that matches, visually resembles, compliments, or coordinates with the pattern of the three-dimensional nonwoven materials used as the topsheet, the acquisition layer, or the topsheet and the acquisition layer laminate of the absorbent article. The outer cover 223 is illustrated in dash in FIG. 29, as an example. The outer cover 223 may be joined to at least a portion of the backsheet 225 through mechanical bonding, adhesive bonding, or other suitable methods of attachment.

Absorbent Core

The absorbent core is the component of the absorbent article that has the most absorbent capacity and that comprises an absorbent material and a core wrap or core bag enclosing the absorbent material. The absorbent core does not include the acquisition and/or distribution system or any other components of the absorbent article which are not either integral part of the core wrap or core bag or placed within the core wrap or core bag. The absorbent core may comprise, consist essentially of, or consist of, a core wrap, an absorbent material (e.g., superabsorbent polymers and little or no cellulose fibers) as discussed, and glue. In other instances, the absorbent material may comprise a mixture of superabsorbent polymers and air-felt or cellulose fibers. This mixture of superabsorbent polymers and air-felt or cellulose fibers may be positioned within the core bag. The core bag may form a C-wrap around the mixture or may be otherwise formed. Glue may also be present within the core bag to at least partially hold the mixture in place during manufacture and wear. Channels may be present in this absorbent material comprising superabsorbent polymers and air-felt. In other instances, embossed areas may form compressed areas in the absorbent core.

The absorbent core 228 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This airfelt-free core is relatively thin compared to a conventional core typically comprising between 40-60% SAP by weight and a high content of cellulose fibers. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

The airfelt-free cores with very little or no natural, cellulosic and/or synthetic fibers are quite thin compared to conventional cores, thereby making the overall absorbent article thinner than absorbent articles with cores comprising mixed SAP and cellulosic fibers (e.g., 40-60% cellulose fibers). This core thinness can lead to consumer perceptions of reduced absorbency and performance, although technically this is not the case. Presently, these thin cores have typically been used with substantially planer or apertured topsheets. Furthermore, absorbent articles having these thin airfelt-free cores have reduced capillary void space since there is little or no natural, cellulosic, or synthetic fibers in the cores. Thus, there may sometimes not be enough capillary void space in the absorbent article to fully accept multiple insults of bodily exudates or a single large insult.

To solve such problems, the present disclosure provides absorbent articles with these thin airfelt-free cores in combination with one of the high-loft, three-dimensional nonwoven materials described herein as a topsheet, an acquisition layer, or as a topsheet and acquisition layer laminate. In such an instance, consumer perception of absorbency and performance, through the increased thickness of the absorbent article owing to the additional thickness provided by the high-loft, three-dimensional nonwoven material, is increased. Furthermore, the three-dimensional nonwoven materials, when used with these thin airfelt-free cores and as the topsheet, the acquisition layer, or the topsheet and acquisition layer laminate, add capillary void space back into the absorbent articles, while still allowing for minimal in-bag stack heights, thereby passing cost savings onto consumers and manufactures. As such, the absorbent articles of the present disclosure may easily absorb multiple bodily exudate insults or single large insults owing to this increased capillary void space. Additionally, absorbent articles that comprise the nonwoven materials as the topsheet, the acquisition layer, or the topsheet and acquisition layer laminate provide consumers with an aesthetically pleasing topsheet relative to a planer topsheet or an apertured topsheet with an increased thickness and thus the consumer perceptions of absorbency and performance.

Figure 32:
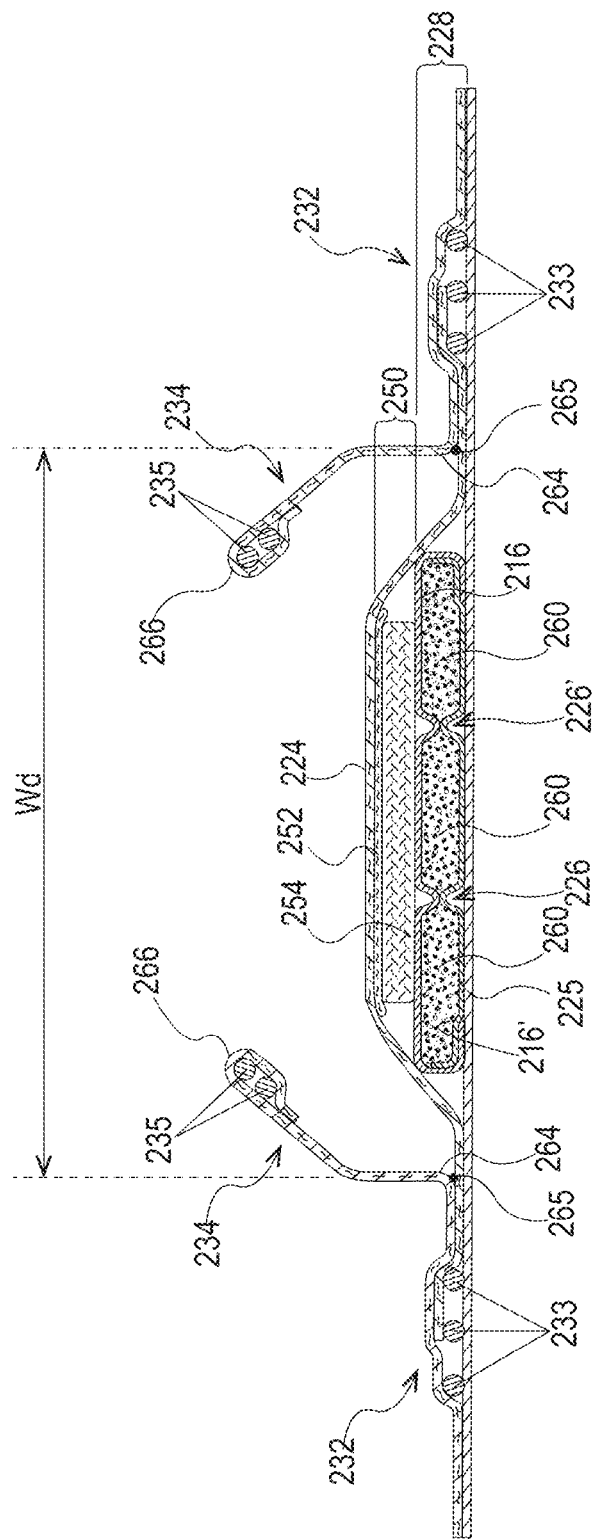
FIG. 32 is a cross-sectional view of the absorbent article taken about line 32-32 of FIG. 31 in accordance with the present disclosure.
Figure 33:
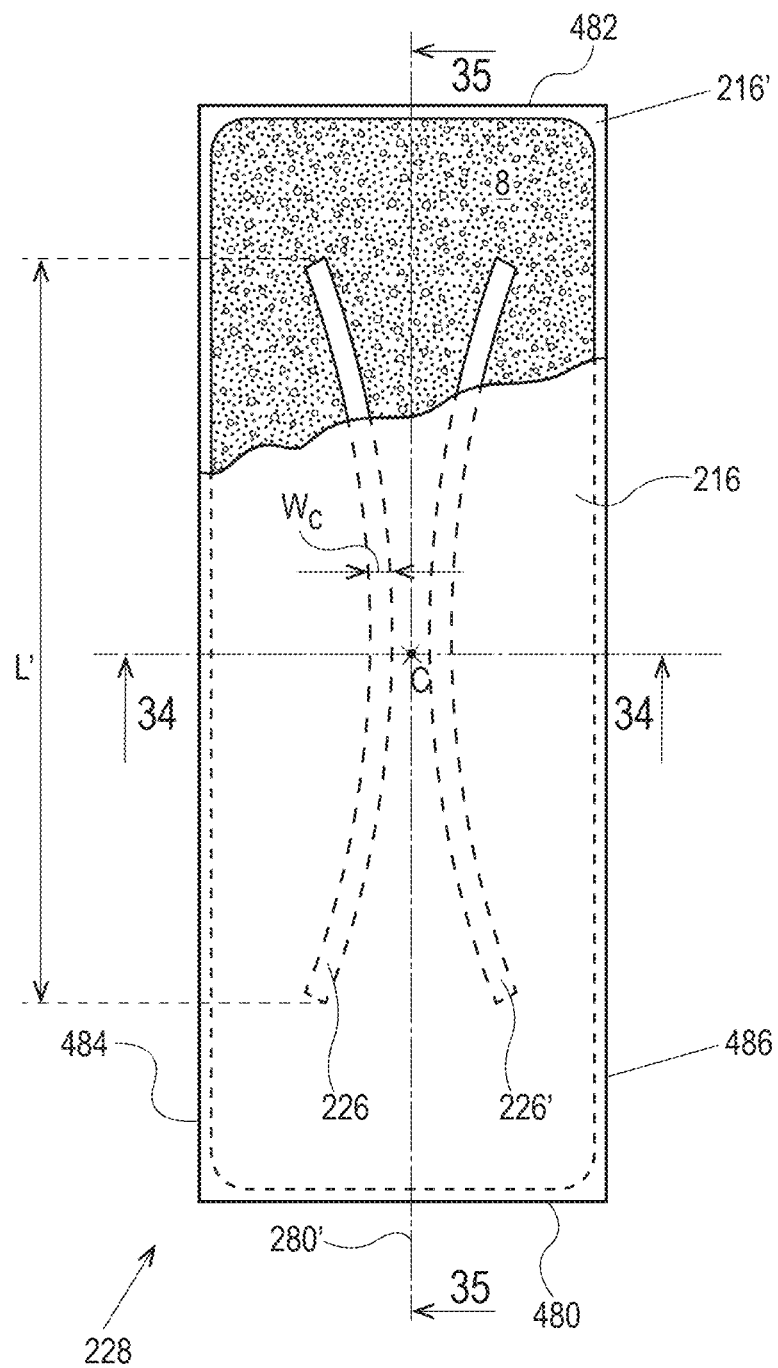
FIG. 33 is a top view of an example absorbent core of the absorbent article of FIG. 31 with some layers partially removed in accordance the present disclosure.
Figure 34:
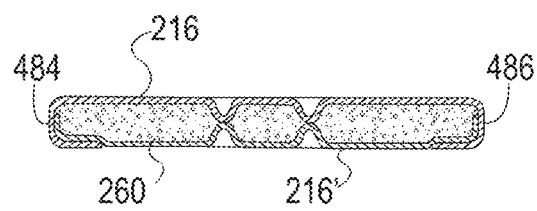
FIG. 34 is a cross-sectional view of the absorbent core taken about line 34-34 of FIG. 33 in accordance with the present disclosure.
Figure 35:
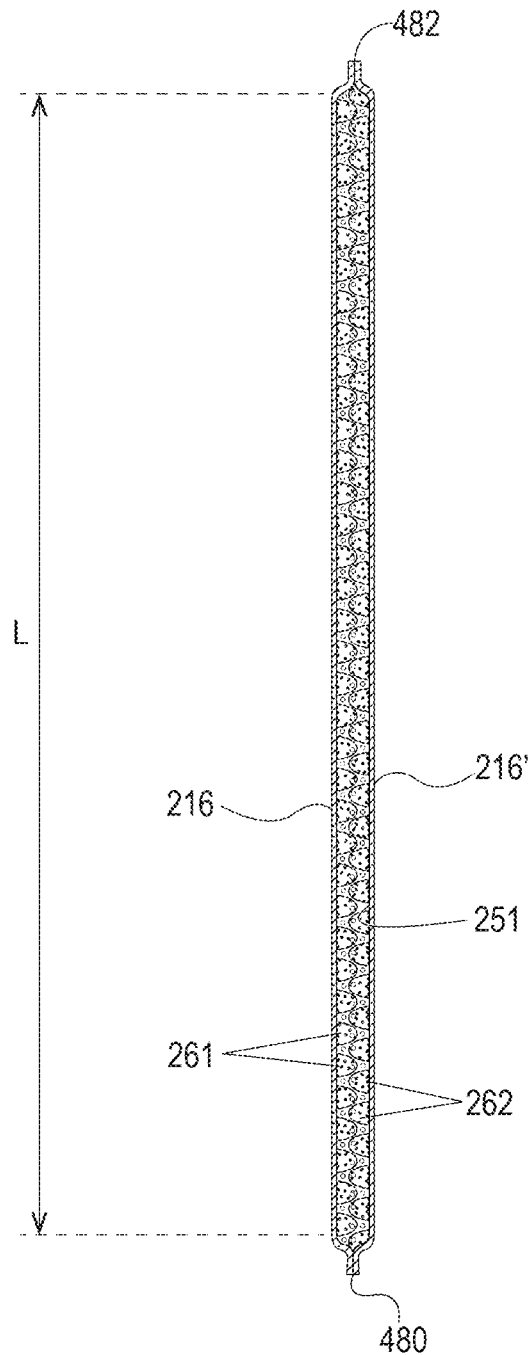
FIG. 35 is a cross-sectional view of the absorbent core taken about line 35-35 of FIG. 33 in accordance with the present disclosure.

The example absorbent core 228 of the absorbent article 220 of FIGS. 31-32 is shown in isolation in FIGS. 33-35. The absorbent core 228 may comprises a front side 480, a rear side 482, and two longitudinal sides 484, 486 joining the front side 480 and the rear side 482. The absorbent core 228 may also comprise a generally planar top side and a generally planar bottom side. The front side 480 of the core is the side of the core intended to be placed towards the front waist edge 210 of the absorbent article. The core 228 may have a longitudinal axis 280' corresponding substantially to the longitudinal axis 280 of the absorbent article 220, as seen from the top in a planar view as in FIG. 28. The absorbent material may be distributed in higher amount towards the front side 480 than towards the rear side 482 as more absorbency may be required at the front in particular absorbent articles. The front and rear sides 480 and 482 of the core may be shorter than the longitudinal sides 484 and 486 of the core. The core wrap may be formed by two nonwoven materials, substrates, laminates, or other materials, 216, 216' which may be at least partially sealed along the sides 484, 486 of the absorbent core 228. The core wrap may be at least partially sealed along its front side 480, rear side 482, and two longitudinal sides 484, 486 so that substantially no absorbent material leaks out of the absorbent core wrap. The first material, substrate, or nonwoven 216 may at least partially surround the second material, substrate, or nonwoven 216' to form the core wrap, as illustrated in FIG. 34. The first material 216 may surround a portion of the second material 216' proximate to the first and second side edges 484 and 486.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H.B. Fuller, for example. The core wrap may extend to a larger area than strictly needed for containing the absorbent material within.

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 228 may comprise a first absorbent layer and a second absorbent layer. The first absorbent layer may comprise the first material 216 and a first layer 261 of absorbent material, which may be 100% or less of SAP. The second absorbent layer may comprise the second material 216' and a second layer 262 of absorbent material, which may also be 100% or less of SAP. The absorbent core 228 may also comprise a fibrous thermoplastic adhesive material 251 at least partially bonding each layer of absorbent material 261, 262 to its respective material 216 or 216'. This is illustrated in FIGS. 34-35, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 280. The first material 216 and the second material 216' may form the core wrap.

The fibrous thermoplastic adhesive material 251 may be at least partially in contact with the absorbent material 261, 262 in the land areas and at least partially in contact with the materials 216 and 216' in the junction areas. This imparts an essentially three-dimensional structure to the fibrous layer of thermoplastic adhesive material 251, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell.

Superabsorbent Polymer (SAP)

The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 210 or rear waist edge 212 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g. The average SAP basis weight within the (or "at least one", if several are present) deposition area 8 of the SAP may be at least 50, 100, 200, 300, 400, 500 or more g/m². The areas of the channels (e.g., 226, 226', 227, 227') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 29 and 34, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 216, 216', four seals may be used to enclose the absorbent material 260 within the core wrap. For example, a first substrate 216 may be placed on one side of the core (the top side as represented in FIGS. 33-35) and extend around the core's longitudinal edges to at least partially wrap the opposed bottom side of the core. The second substrate 216' may be present between the wrapped flaps of the first substrate 216 and the absorbent material 260. The flaps of the first substrate 216 may be glued to the second substrate 216' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are also within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 208 may be defined by the periphery of the layer formed by the absorbent material 260 within the core wrap, as seen from the top side of the absorbent core. The absorbent material deposition area 208 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 28. This may provide better wearing comfort. The absorbent material deposition area 8 may also be generally rectangular, for example as shown in FIGS. 31-33, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels in Absorbent Core

The absorbent material deposition area 208 may comprise at least one channel 226, which is at least partially oriented in the longitudinal direction of the article 280 (i.e., has a longitudinal vector component). Other channels may be at least partially oriented in the lateral direction (i.e., has a lateral vector component) or in any other direction. In the following, the plural form "channels" will be used to mean "at least one channel". The channels may have a length L' projected on the longitudinal axis 280 of the article that is at least 10% of the length L of the article. The channels may be formed in various ways. For example, the channels may be formed by zones within the absorbent material deposition area 208 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 208. The channels may be continuous, but it is also envisioned that the channels may be intermittent. The acquisition-distribution system or layer 240, or another layer of the article, may also comprise channels, which may or not correspond to the channels of the absorbent core.

In some instances, the channels may be present at least at the same longitudinal level as the crotch point C or the lateral axis 260 in the absorbent article, as represented in FIG. 28 with the two longitudinally extending channels 226, 226'. The channels may also extend from the crotch region 207 or may be present in the front waist region 205 and/or in the rear waist region 206 of the article.

The absorbent core 228 my also comprise more than two channels, for example, at least 3, at least 4, at least 5, or at least 6 or more. Shorter channels may also be present, for example in the rear waist region 206 or the front waist region 205 of the core as represented by the pair of channels 227, 227' in FIG. 28 towards the front of the article. The channels may comprise one or more pairs of channels symmetrically arranged, or otherwise arranged relative to the longitudinal axis 280.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 208, and may therefore be fully encompassed within the absorbent material deposition area 208 of the core. The smallest distance between a channel and the closest edge of the absorbent material deposition area 208 may be at least 5 mm.

The channels may have a width We along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 208, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 216 and the second substrate 216') and/or the topsheet 224 to the backsheet 225 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 224 and the backsheet 225 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 224 and/or the backsheet 225 and a free terminal edge 266, which is intended to contact and form a seal with the wearer's skin. The barrier leg cuffs 234 extend at least partially between the front waist edge 210 and the rear waist edge 212 of the absorbent article on opposite sides of the longitudinal axis 280 and are at least present at the level of the crotch point (C) or crotch region. The barrier leg cuffs may be joined at the proximal edge 264 with the chassis of the article by a bond 265 which may be made by gluing, fusion bonding, or a combination of other suitable bonding processes. The bond 265 at the proximal edge 264 may be continuous or intermittent. The bond 265 closest to the raised section of the leg cuffs delimits the proximal edge 264 of the standing up section of the leg cuffs.

The barrier leg cuffs may be integral with the topsheet 224 or the backsheet 225 or may be a separate material joined to the article's chassis. Each barrier leg cuff 234 may comprise one, two or more elastic strings 235 close to the free terminal edge 266 to provide a better seal.

In addition to the barrier leg cuffs 234, the article may comprise gasketing cuffs 232, which are joined to the chassis of the absorbent article, in particular to the topsheet 224 and/or the backsheet 225 and are placed externally relative to the barrier leg cuffs. The gasketing cuffs 232 may provide a better seal around the thighs of the wearer. Each gasketing leg cuff may comprise one or more elastic strings or elastic elements 233 in the chassis of the absorbent article between the topsheet 224 and backsheet 225 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution material 254 and an acquisition layer 252 disposed between the absorbent core and the topsheet, but the present disclosure is not so limited.

In one example, the high loft, three-dimensional nonwoven materials of the present disclosure may comprise the topsheet and the acquisition layer as a laminate or just as the topsheet or the acquisition layer individually. A distribution material may also be provided on the garment-facing side of the topsheet/acquisition layer laminate, on the garment-facing side of the acquisition layer, or on a garment-facing side of a carrier layer, as is discussed below.

Carrier Layer

In an instance where the high loft, three-dimensional nonwoven materials of the present disclosure encompass a topsheet and acquisition layer laminate or just the acquisition layer, the distribution material may need to be supported by a carrier layer (illustrated in later figures) that may comprise one or more nonwoven materials, cellulose materials, and/or other materials, as will be further detailed below. The material of the distribution material may be applied to or positioned on the carrier layer. As such, the carrier layer may be positioned intermediate the acquisition layer and the distribution material and be in a facing relationship with the acquisition layer and the distribution material. The carrier layer may also be positioned intermediate the distribution material and a wearer-facing surface of the core bag.

Distribution Material

The distribution material of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution material comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents).

In other instances, the distribution material may comprise cellulose fibers or pulp. In some instances, the distribution material may comprise at least 80%, at least 90%, at least 99% or 100% cellulose fibers or pulp. In certain instances, such a distribution material may be formed of a single layer or multiple layers. In still other instances, such a distribution material may comprise a single layer folded any suitable number of times over itself. The cellulose fiber or pulp based distribution materials may be three-dimensional materials. In still other instances, the distribution material may be formed of any suitable distribution materials.

Acquisition Layer

The acquisition layer may be disposed between the distribution material 254 or carrier layer and the topsheet 224. The acquisition layer may or may not be nested with the topsheet as explained herein. If the acquisition layer is not nested with the topsheet it may be planer or three-dimensional. The acquisition layer 252 may comprise any suitable material, such as a high elongation spunbond material, for example.

Fastening System

The absorbent article may comprise a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 244 is normally provided on the garment-facing surface of the front waist region 205 for the fastener to be releasably attached thereto.

Front and Rear Ears

The absorbent article may comprise front ears 246 and rear ears 240. The ears may be an integral part of the chassis, such as formed from the topsheet 224 and/or backsheet 226 as side panels. Alternatively, as represented on FIG. 28, the ears may be separate elements attached by gluing, heat embossing, and/or pressure bonding. The rear ears 240 may be stretchable to facilitate the attachment of the tabs 242 to the landing zone 244 and maintain the taped diapers in place around the wearer's waist. The rear ears 240 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 220 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 228 and generally forms at least a portion of the end edge of the absorbent article. Disposable diapers may be constructed so as to have two elastic waist features, one positioned in the front waist region and one positioned in the rear waist region.

Channels in Layers Other Than the Absorbent Core

Various channels e.g., 226, 226' in the absorbent core were described in detail above. To achieve fluid distribution along a longitudinal direction of an absorbent article and/or a consumer impression of the same, the present disclosure provides one or more channels in one or more other layers intermediate the core bag and the acquisition layer in addition to the one or more channels in the absorbent core. Namely, in some instances, these one or more additional channels may be provided in a distribution material, a carrier layer, and/or any other suitable layer intermediate the absorbent core and the acquisition layer. If some instances, if the acquisition layer is not formed into a laminate with the topsheet and is generally planar, channels may also be formed in the acquisition layer. In such an instance, the topsheet may comprise the three-dimensional materials of the present disclosure. In this example, the acquisition layer may be positioned intermediate the topsheet and the absorbent core or may have other layers intermediate itself and the absorbent core.

Figure 43:
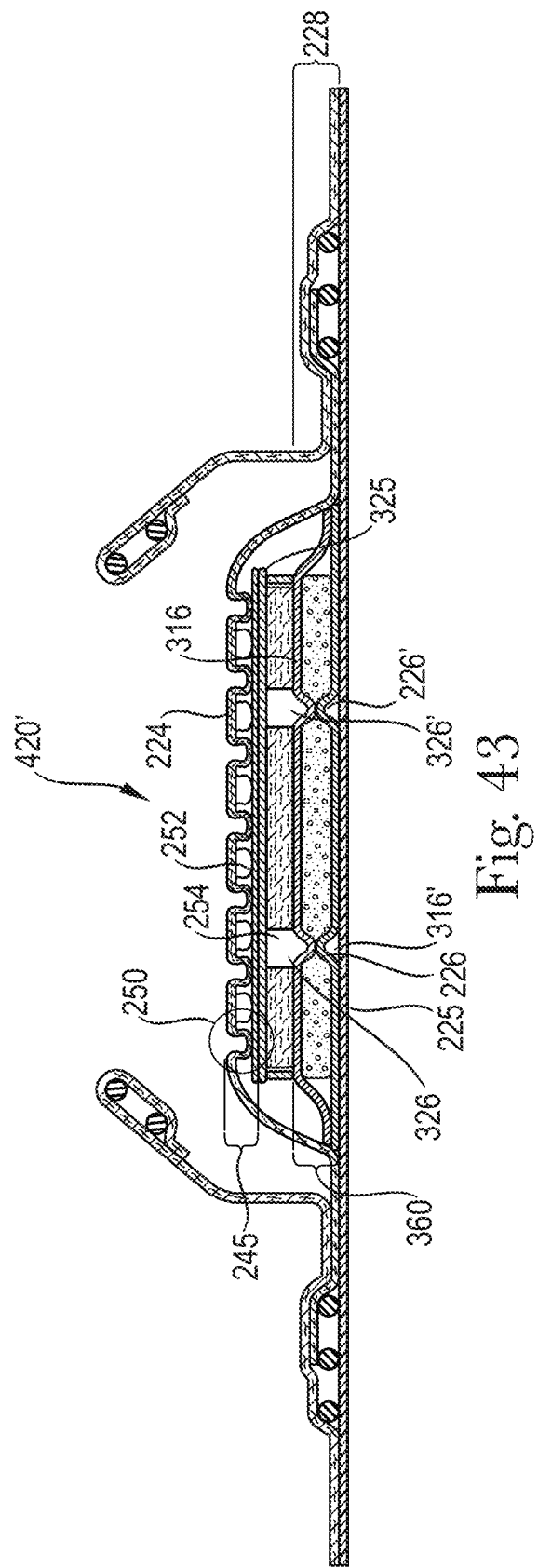
FIG. 43 is an example cross-sectional view of an absorbent article with a three-dimensional topsheet, an absorbent core, a generally planar acquisition layer, and two materials intermediate the absorbent core and the generally planar acquisition layer, wherein channels are present in the absorbent core and one of the materials intermediate the absorbent core and the generally planar acquisition layer in accordance with the present disclosure.
Figure 44:
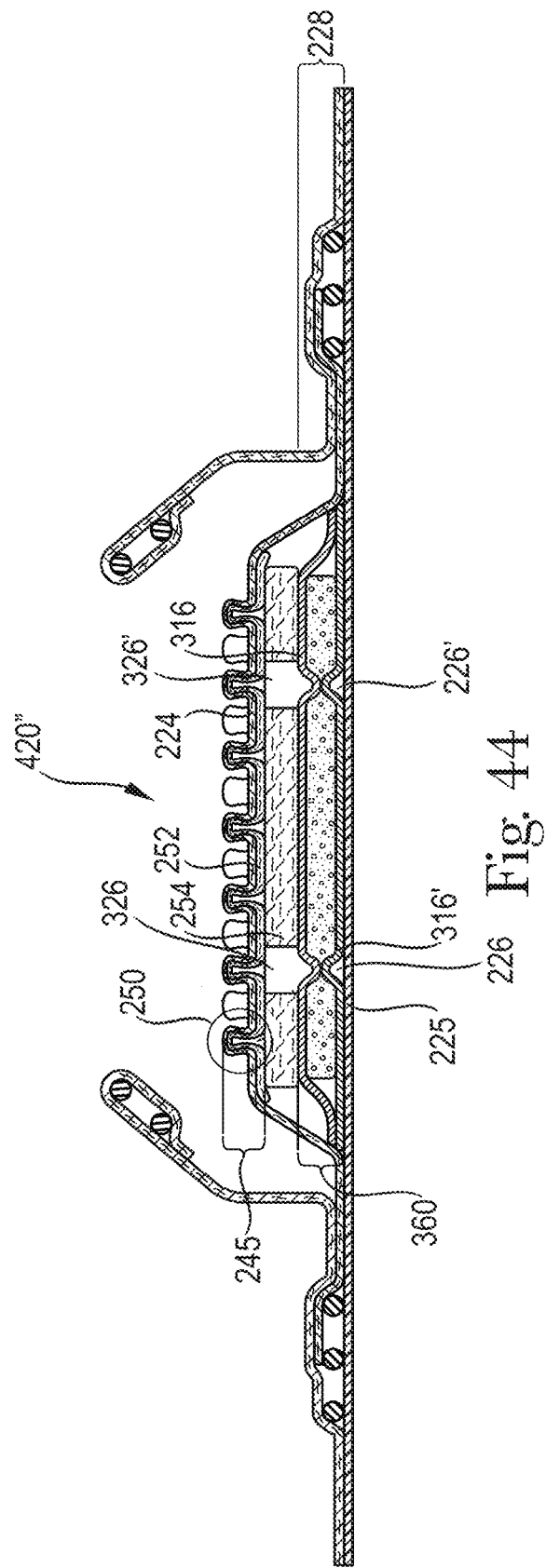
FIG. 44 is an example cross-sectional view of an absorbent article, with an absorbent core and a material intermediate the absorbent core and a multilayer nonwoven web, both having channels in accordance with the present disclosure.

In FIGS. 36-43 and 45-52 the protrusions 250 extend toward the absorbent core 228, while in FIG. 44 the protrusions 250 extend away from the absorbent core. The present disclosure encompasses forms where the protrusions extend away from the absorbent core and towards the absorbent core.

Figure 36:
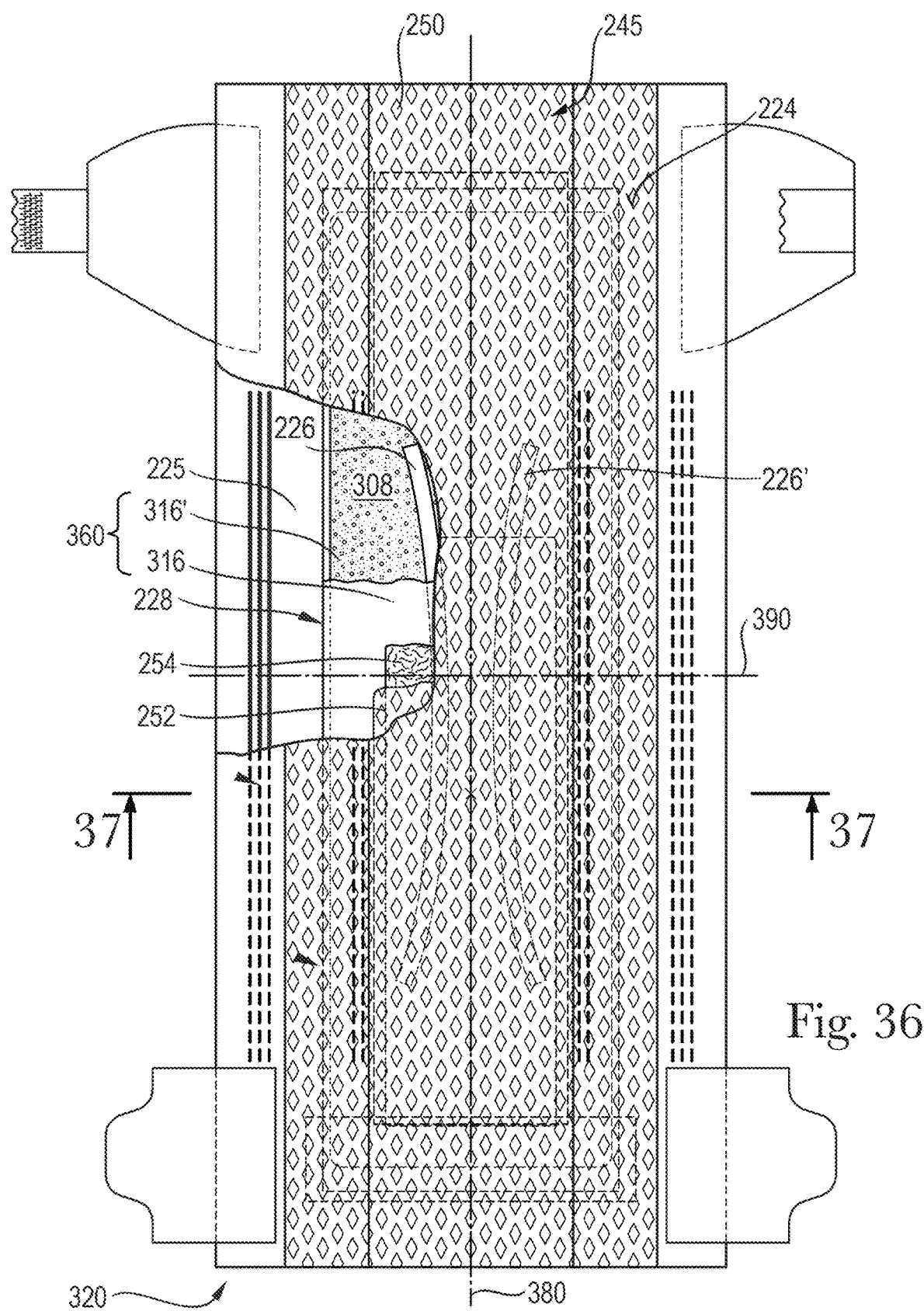
FIG. 36 is an example absorbent article in the form of a diaper comprising an example multilayer nonwoven web with the length of the acquisition layer being less than the length of the topsheet, with channels in an absorbent core, and with some layers partially removed in accordance with the present disclosure.

FIG. 36 illustrates an example absorbent article 320. The absorbent article 320 comprises a longitudinal axis 380 and a lateral axis 390. Absorbent core channels 226 and 226' are defined in an absorbent material 308 of the absorbent core 228. The absorbent material 308 is enclosed in a core bag 360 having two layers or nonwoven layers 316 and 316'. The two nonwoven layers 316 and 316' may form a C-wrap around the absorbent material 308 or otherwise enclose the absorbent material. The absorbent article 320 may comprise a distribution material 254. The absorbent article may also comprise a topsheet 224 and an acquisition layer 252 that are nested together to form a three-dimensional topsheet/acquisition layer laminate 245, as described in further detail herein. The three-dimensional topsheet/acquisition layer laminate may comprise a plurality of protrusions 250. The absorbent article 320 also comprises a backsheet 225. Other features (e.g., fastening system) of the absorbent article 320 may be the same as or similar to that described herein, and as such, will not be described again here for brevity.

Figure 37:
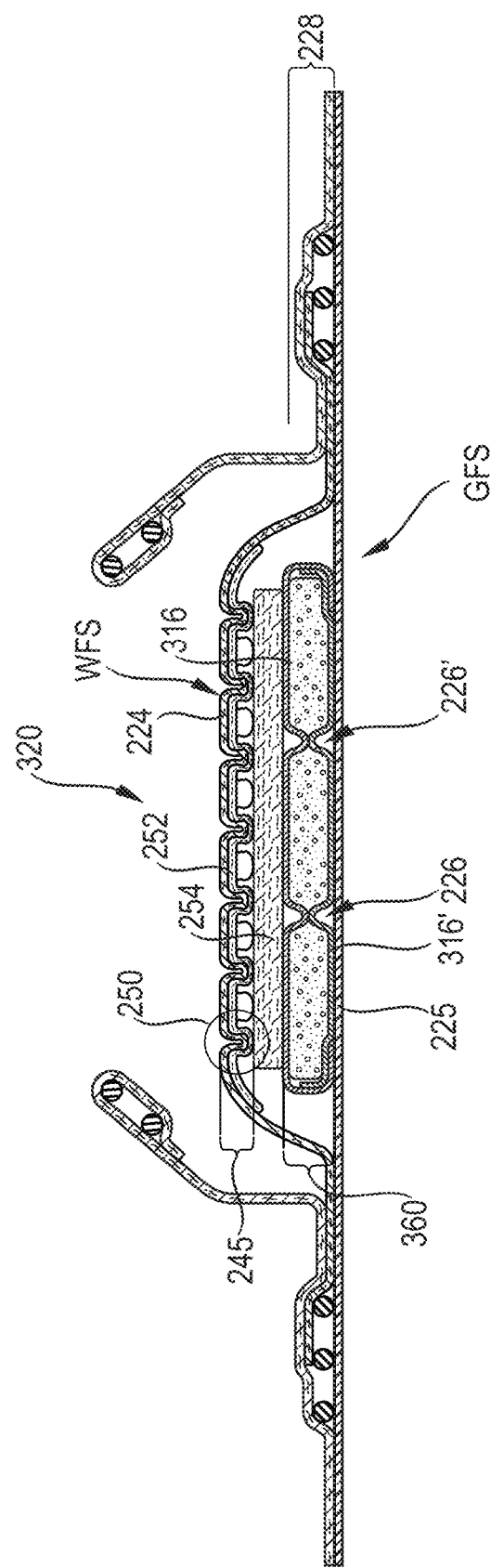
FIG. 37 is an example cross-sectional view of the absorbent article of FIG. 36, taken about line 37-37, with the absorbent core having channels, in accordance with the present disclosure.

FIG. 37 illustrates a cross-sectional view of the absorbent article 320 taken about line 37-37 of FIG. 36. As can be seen, the layering of the example absorbent article 320 from the wearer-facing surface ("WFS") to the garment-facing surface ("GFS") is as follows: a nested topsheet/acquisition layer laminate 245; a distribution material or layer 254; an absorbent core 228 (including the core bag 360); and a backsheet 225. An outer cover nonwoven material may also be provided on the GFS to cover the backsheet.

Figure 38:
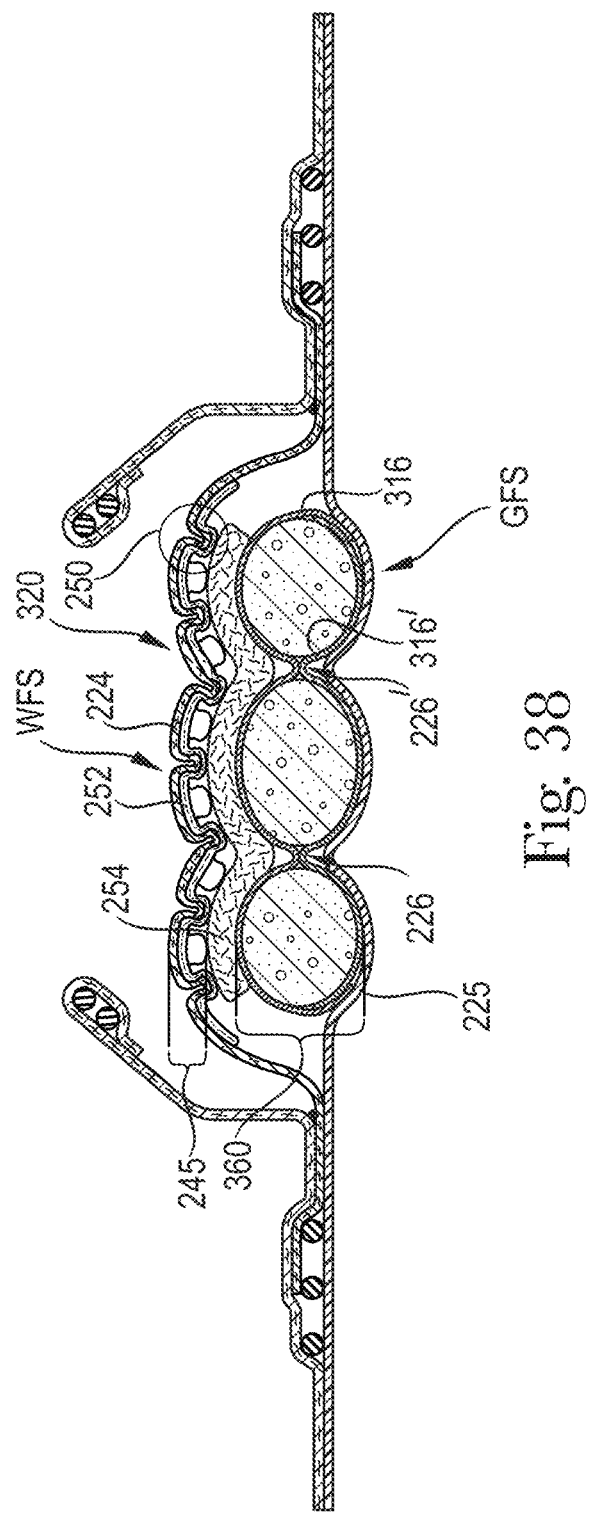
FIG. 38 is an example cross-sectional view of the absorbent article of FIG. 36, taken about line 37-37, with the absorbent core at least partially loaded with a fluid in accordance with the present disclosure.

FIG. 38 illustrates the cross-sectional view of FIG. 37 with the absorbent core 228 at least partially loaded with a fluid.

Figure 39:
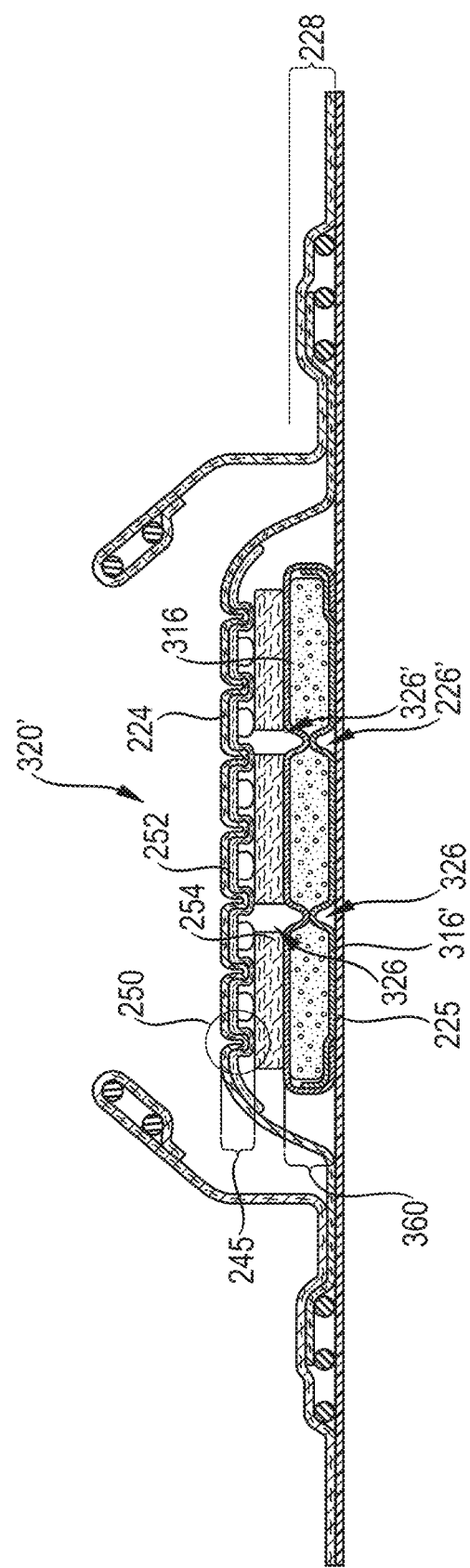
FIG. 39 is an example cross-sectional view of an absorbent article, with an absorbent core and a material intermediate the absorbent core and a multilayer nonwoven web, both having channels in accordance with the present disclosure.

FIG. 39 illustrates another example cross-sectional view of an absorbent article 320'. As can be seen, the distribution material 254 may comprise one or more channels 326 and 326'. Any suitable number of channels, such as one, two, three, or more, may be provided in the distribution material 254. This distribution material 254 may comprise air-felt or any other suitable material, such as the distribution materials described above. The channels 326 and 326' may have any suitable size, shape, and/or orientation. The channels 326 and 326' in the distribution material 254 may or may not overlap in the Z-direction with the channels 226 and 226' in the absorbent core 228. If the channels 326 and 326' and the channels 226 and 226' do overlap in the Z-direction they may partially overlap or fully overlap. For example, the channels 326 and 326' may not be as wide or as long as the channels 226 or 226' or vice versa. In an instance, only one of the channels 326 and 326' may at least partially overlap or be free of overlap in the Z-direction with only one of the channels 226 and 226'.

Figure 40:
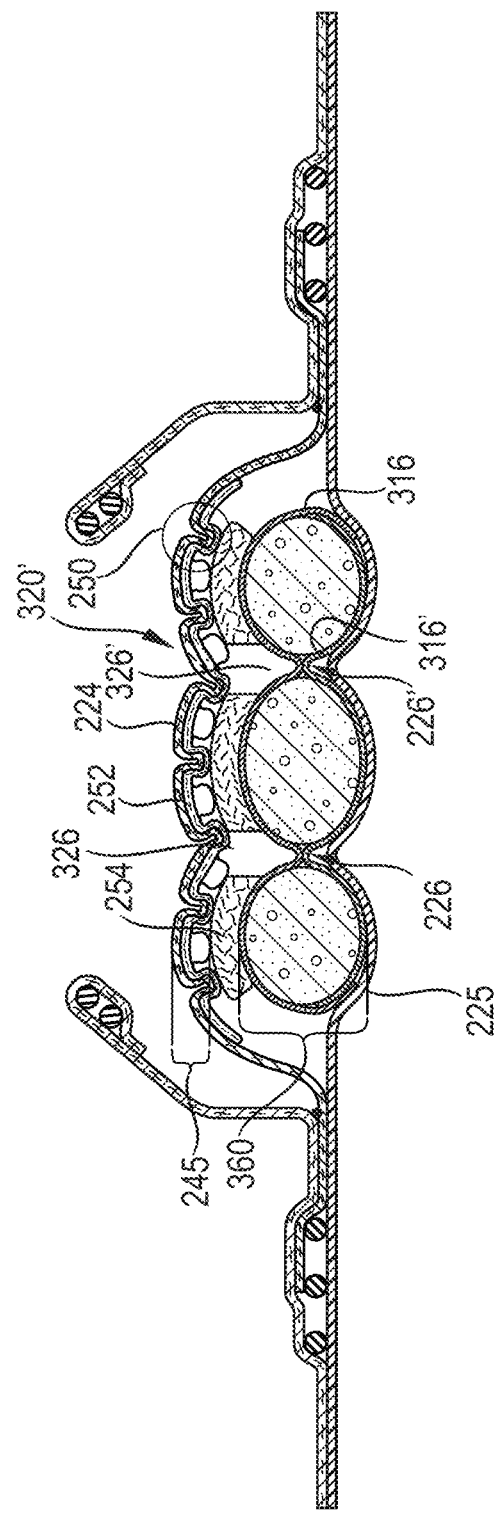
FIG. 40 is an example cross-sectional view of the absorbent article of FIG. 39 with the absorbent core at least partially loaded with a fluid in accordance with the present disclosure.

FIG. 40 is the cross-sectional view of the absorbent article 320' of FIG. 39 with the absorbent core 228 at least partially loaded with a fluid.

Figure 41:
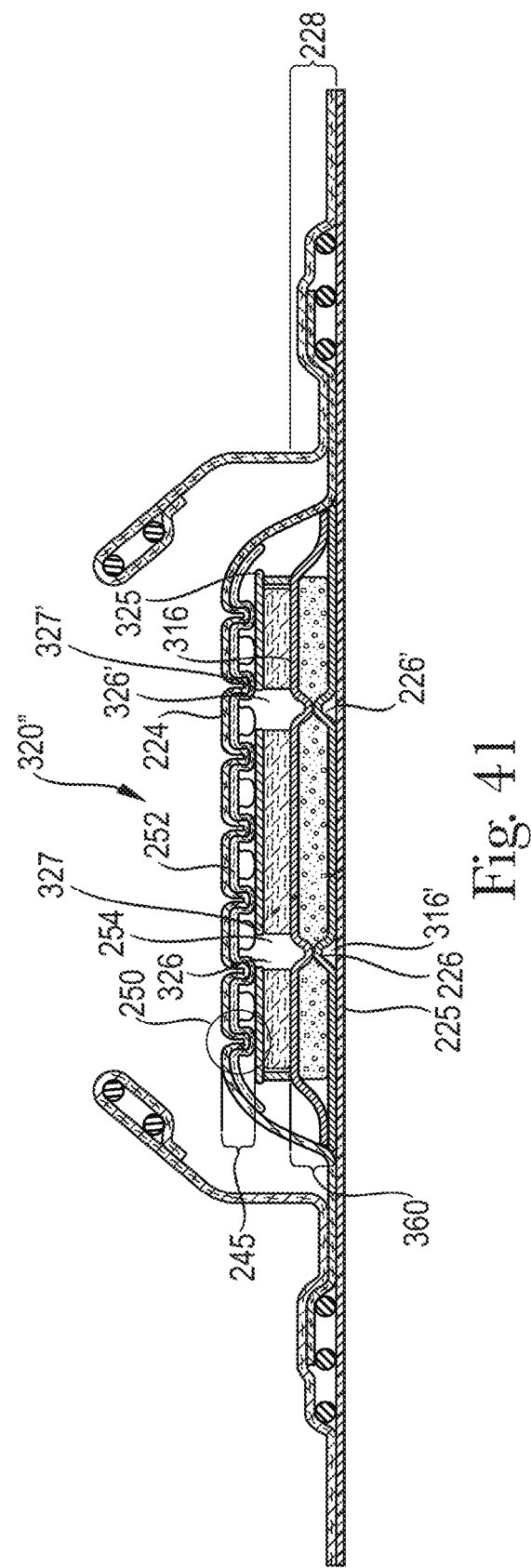
FIG. 41 is an example cross-sectional view of an absorbent article, with an absorbent core and two materials intermediate the absorbent core and a multilayer nonwoven web, all having channels in accordance with the present disclosure.

FIG. 41 illustrates another example cross-sectional view of an absorbent article 320". The distribution material 254 may comprise channels 326 and 326' that may be the same as or similar to the distribution material channels described above with respect to FIG. 39. In this instance, however, an optional carrier layer 325 may be provided. The carrier layer 325 may also comprise one or more channels 327 and 327'. The carrier layer 325 may comprise a nonwoven material, a cellulose fiber or pulp based material, and/or or any other suitable material. If the carrier layer 325 comprises a cellulose fiber or pulp based material, it may comprise at least 80%, at least 90%, at least 99%, or 100% cellulose fiber or pulp by weight. The carrier layer 325 may comprise a three-dimensional material comprising at least 80%, at least 90%, at least 99%, or 100% cellulose fiber or pulp by weight. In an instance, the three-dimensional material of the carrier layer 325 may be a variable basis weight and variable density material. The carrier layer 325 may be optional in some absorbent article forms. For example, a carrier layer may not be desired when the acquisition layer 252 is generally flat, for example. In some instances, it may be difficult to attach the distribution material 254 to a three-dimensional garment-facing surface of the three-dimensional material (whether an acquisition layer 252 or a topsheet/acquisition layer laminate). As such, the carrier layer 325 may be used to provide an attachment surface for the distribution material.

Any suitable number of channels, such as one, two, three, or more, may be provided in the carrier layer 325. The channels 327 and 327' may or may not overlap, in the Z-direction, with the channels 326 and 326' in the distribution material 254 and/or the channels 226 and 226' in the absorbent core 228. If any of the channels 327 and 327', 326 and 326', and 226 and 226' do overlap, in the Z-direction, they may partially overlap or fully overlap. For example, the channels 327 and 327' may not be as wide or as long as the channels 326 and 326' and/or the channels 226 or 226' or vice versa. Some of or all of the channels in the various layers may or may not at least partially or fully overlap in the Z-direction. In another instance, at least one channel in one layer (e.g., distribution material 254) may overlap, in the Z-direction, with at least one channel in another layer (e.g., the absorbent core 228), while at least one other channel in the one layer (e.g., the distribution material 254) may not overlap, in the Z-direction, with at least one channel in the another layer (e.g., the absorbent core 228).

Figure 42:
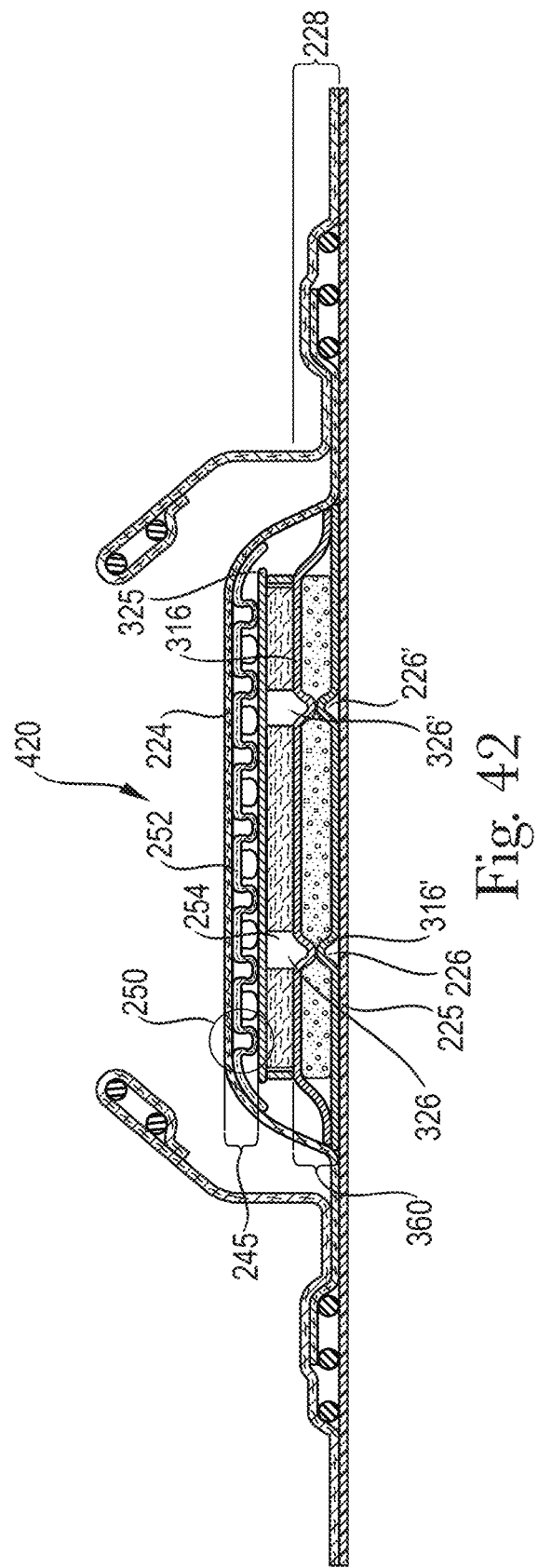
FIG. 42 is an example cross-sectional view of an absorbent article with an absorbent core, a generally planar topsheet, a three-dimensional acquisition layer, and two materials intermediate the absorbent core and the three-dimensional acquisition layer, wherein the absorbent core and one of the materials intermediate the absorbent core and the three-dimensional acquisition layer have channels in accordance with the present disclosure.

FIG. 42 illustrates an example cross-sectional view of an absorbent article 420 with the same channel configuration as the absorbent article 320' of FIG. 39, but with a carrier layer 325 and with a topsheet 224 comprising a generally planer or flat material. The acquisition layer 252, in this instance, comprises the three-dimensional nonwoven material.

FIG. 43 illustrates an example cross-sectional view of an absorbent article 420' with the same channel configuration as the absorbent article 320' of FIG. 39, but with a carrier layer 325, and with an acquisition layer 252 comprising a generally planer or flat material. The topsheet 224, in this instance, comprises the three-dimensional nonwoven material.

FIG. 44 illustrates an example cross-sectional view of an absorbent article 420" with the same channel configuration as the absorbent article 320' of FIG. 39, but with the protrusions 250 of the three-dimensional nonwoven material 245 extending away from the absorbent core 228.

Figure 45:
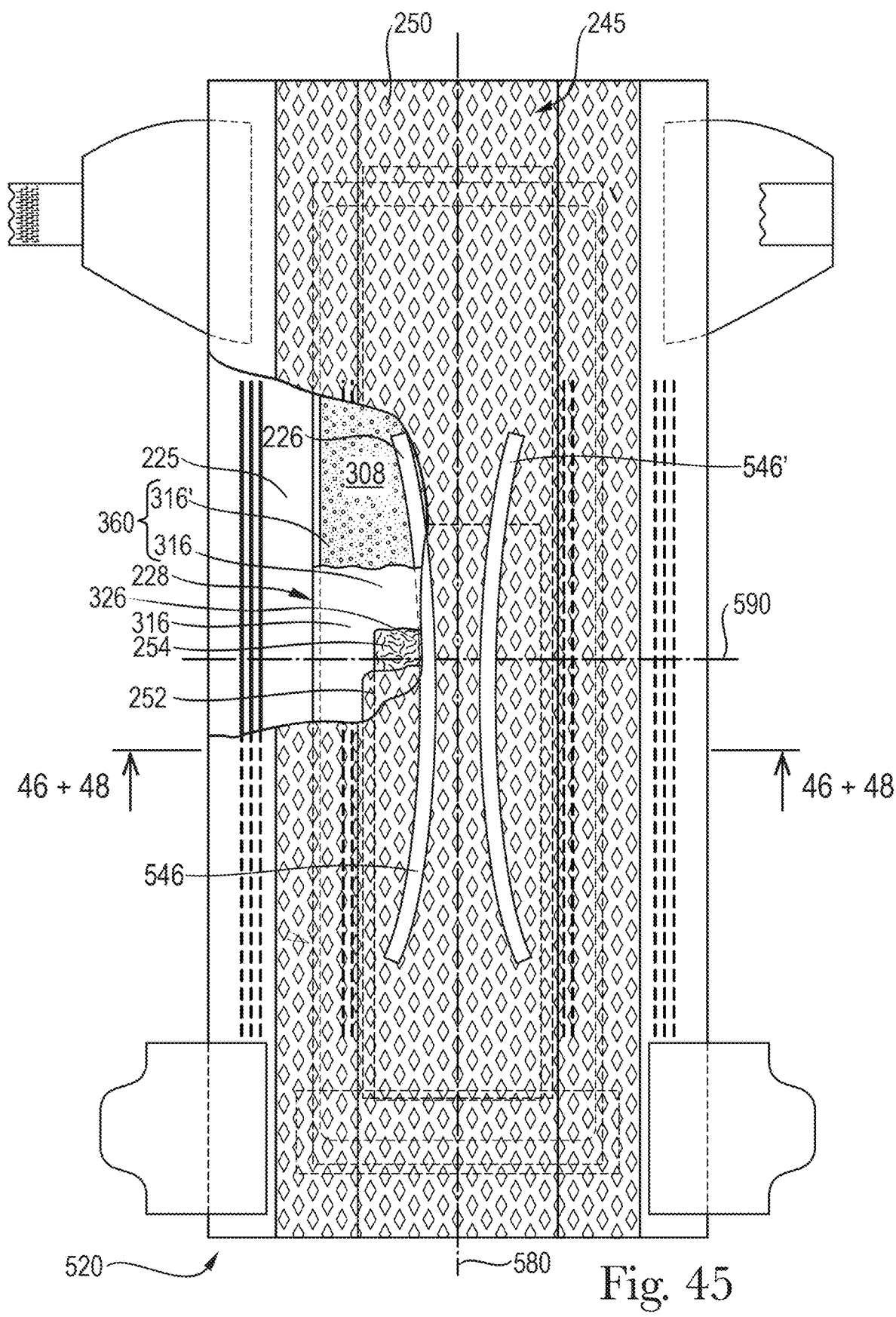
FIG. 45 is a plan view of an absorbent article having channels and the multilayer nonwoven web having a design in accordance with the present disclosure.

FIG. 45 illustrates a plan view of an absorbent article 520 having a longitudinal axis 580 and a lateral axis 590. The absorbent article 520 may comprise one or more channels 226 and 226' in an absorbent material 308 of an absorbent core 228 and one or more channels 326 and 326' in a distribution material 254. A carrier layer may also be provided intermediate an acquisition layer 252 and the distribution material 254, although not illustrated in FIG. 45. This carrier layer may comprise one or more channels (e.g., channels 327 and 327' of FIG. 41). The three-dimensional nonwoven material 245, the topsheet 224, and/or the acquisition layer 252 may comprise one or more designs 546 and 546'. The designs 546 and 546' are merely examples of some suitable designs. Other designs having different shapes, sizes, and/or orientations are also within the scope of the present disclosure. In an instance, one design may be the same as or different than the other design. Any suitable number of designs may be provided. The designs may differ in color, size, shape, orientation, or other visual aspect. In general, the designs should be visible from a wearer-facing surface of the absorbent article 520. In an instance, the protrusions 250 may only be present in an area of the absorbent article 520 that corresponds with the acquisition layer 252, or an area smaller than the acquisition layer 252, for example. In such instances, the protrusions 250 may not extend fully about the length of the absorbent article 520 or fully about the width of the absorbent article 520.

In some forms, the designs may comprise ink or a structural difference in the material, for example. The inks may comprise a pigment that is visibly distinct from remaining portions of the topsheet and/or acquisition material, for example. The inks may be printed on, applied to, or formed on either surface of the topsheet 224 or either surface of the acquisition layer 252. The structural difference in the material may be embossing or a different, size, shape, and/or orientation of the projections 250, for example. The structural difference should be visible from the wearer-facing surface. The structural difference may be areas without any protrusions as well.

In some instances, one or more certain designs may be on the topsheet 224 with one or more other certain designs on the acquisition layer, for example.

The designs 546 and 546' may be elongate and may or may not partially or fully overlap with channels in any of the layers.

Figure 46:
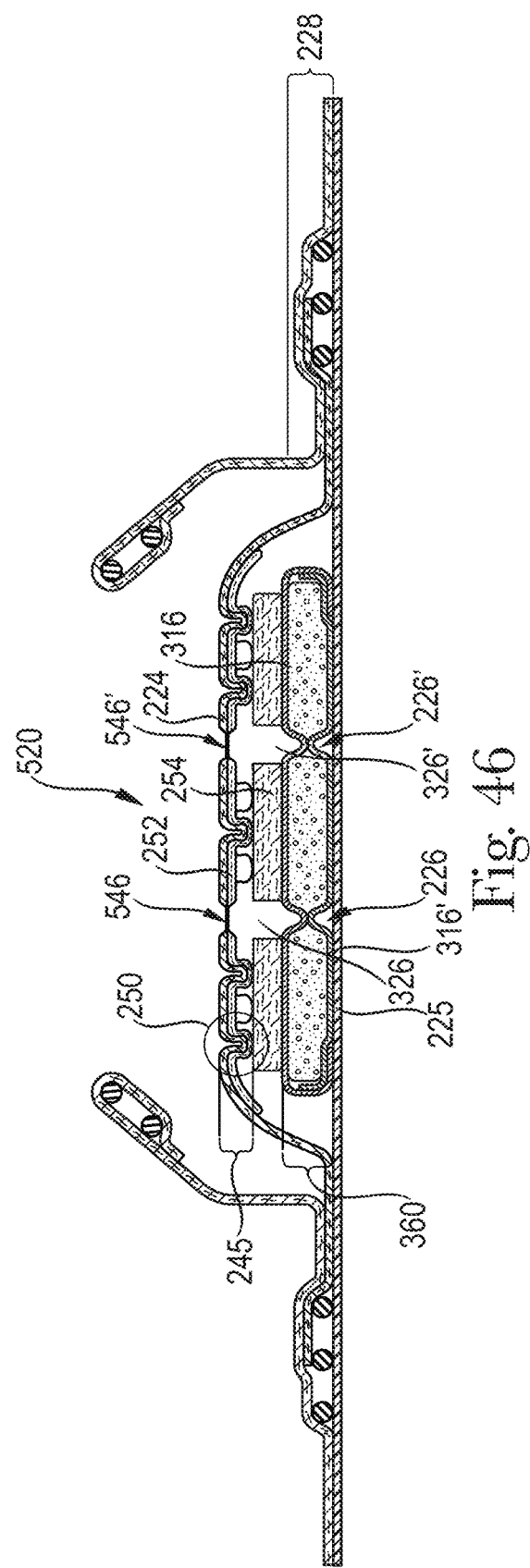
FIG. 46 is an example cross-sectional view of the absorbent article of FIG. 45, taken about line 46-46, in accordance with the present disclosure.

FIG. 46 is a cross-sectional view of the absorbent article 520 taken about line 46-46 of FIG. 45. In the example illustrated in FIG. 46, the designs 546 and 546' comprise a non-nested, compressed area in the three-dimensional nonwoven material 245. In some instances, the designs may be compressed areas or non-nested areas (e.g., FIG. 48) in the topsheet 224 and/or in the acquisition layer 252. In any event, the example designs 546 and 546', or other designs, may fully overlap with, at least partially overlap with, or be free of overlap with, all in the Z-direction, with the channels 226 and 226' in the absorbent core 228, the channels 326 and 326' in the distribution material 254, and/or the channels 327 and 327' in the carrier layer, if provided. In some instances, the designs 546 and 546' may be shorter, longer, wider, narrower, or have different shapes than any of the channels 226, 226', 326, 326', 327, and/or 327'. The designs 546 and 546' may comprise a color different than a remainder of the material they are part of, applied to, and/or printed on.

Figure 47:
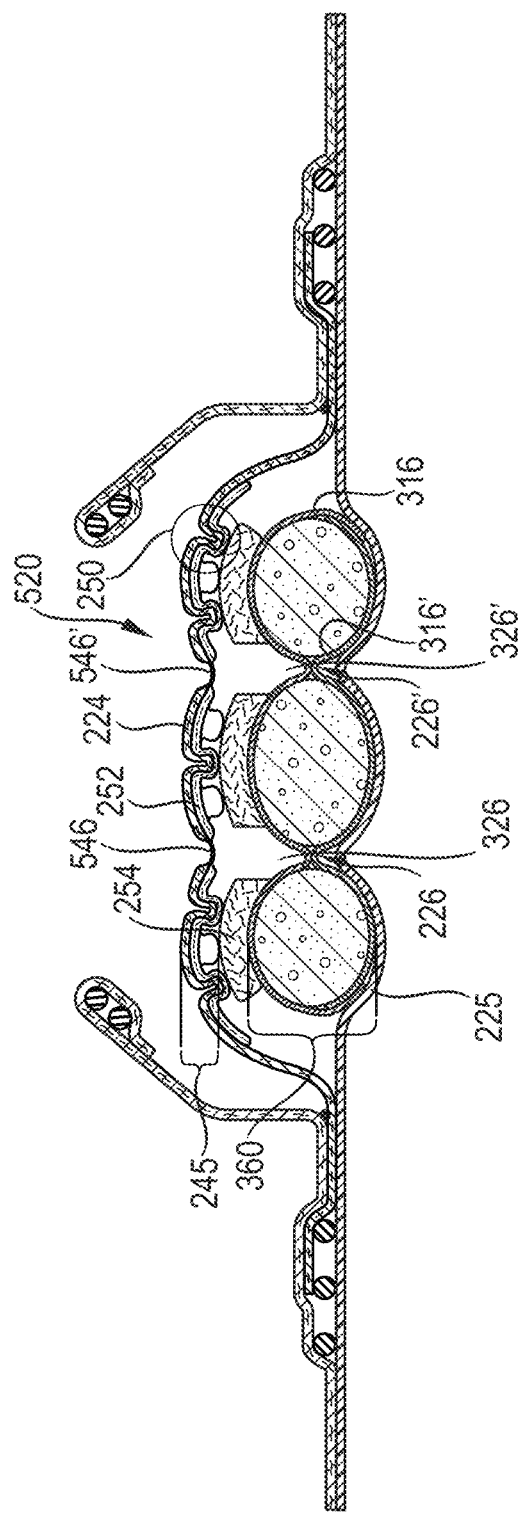
FIG. 47 is the cross-sectional view of the absorbent article of FIG. 46, with the absorbent core at least partially loaded with a fluid in accordance with the present disclosure.

FIG. 47 is the cross-sectional view of the absorbent article 520 of FIG. 46 with the absorbent core 228 at least partially loaded with a fluid.

Figure 48:
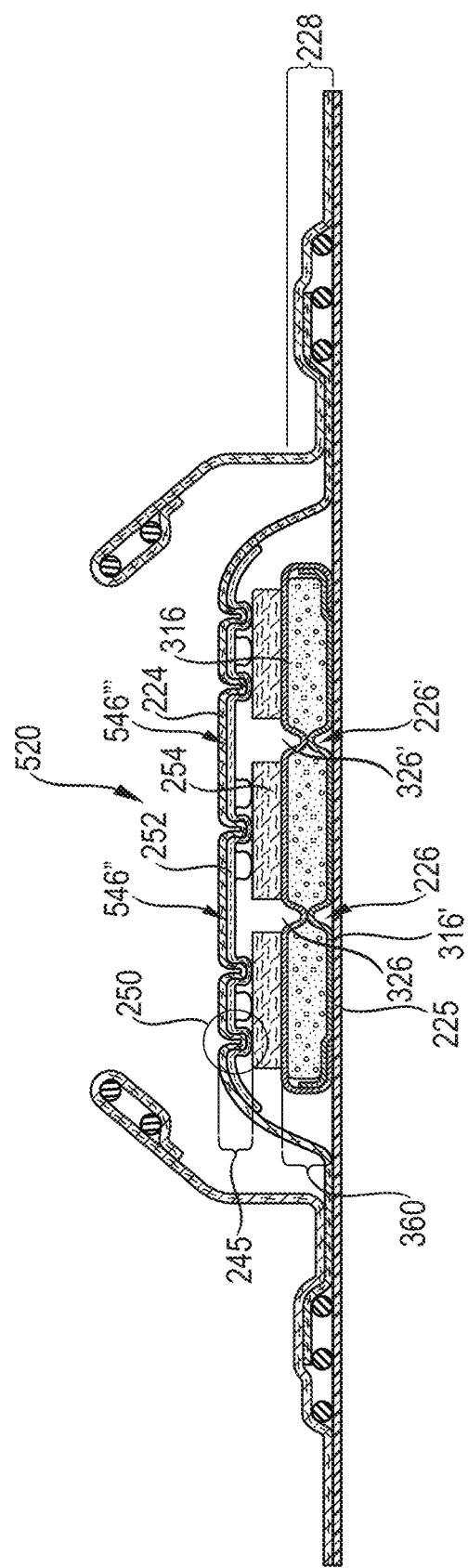
FIG. 48 is an example cross-sectional view of an absorbent article having channels and a multilayer nonwoven web having a design, in accordance with the present disclosure.

FIG. 48 is another example cross-sectional view of the absorbent article 520 of FIG. 45 taken about line 48-48. The example of FIG. 48 comprises the same channel configuration as the example of FIG. 46 and comprises designs 546" and 546'''. The designs 546" and 546''' are areas in the three-dimensional material that are free of, or at least mostly free of, three-dimensional protrusions 250. Stated another way, the designs 546" and 546''' are non-nested areas, or substantially non-nested areas.

Figure 49:
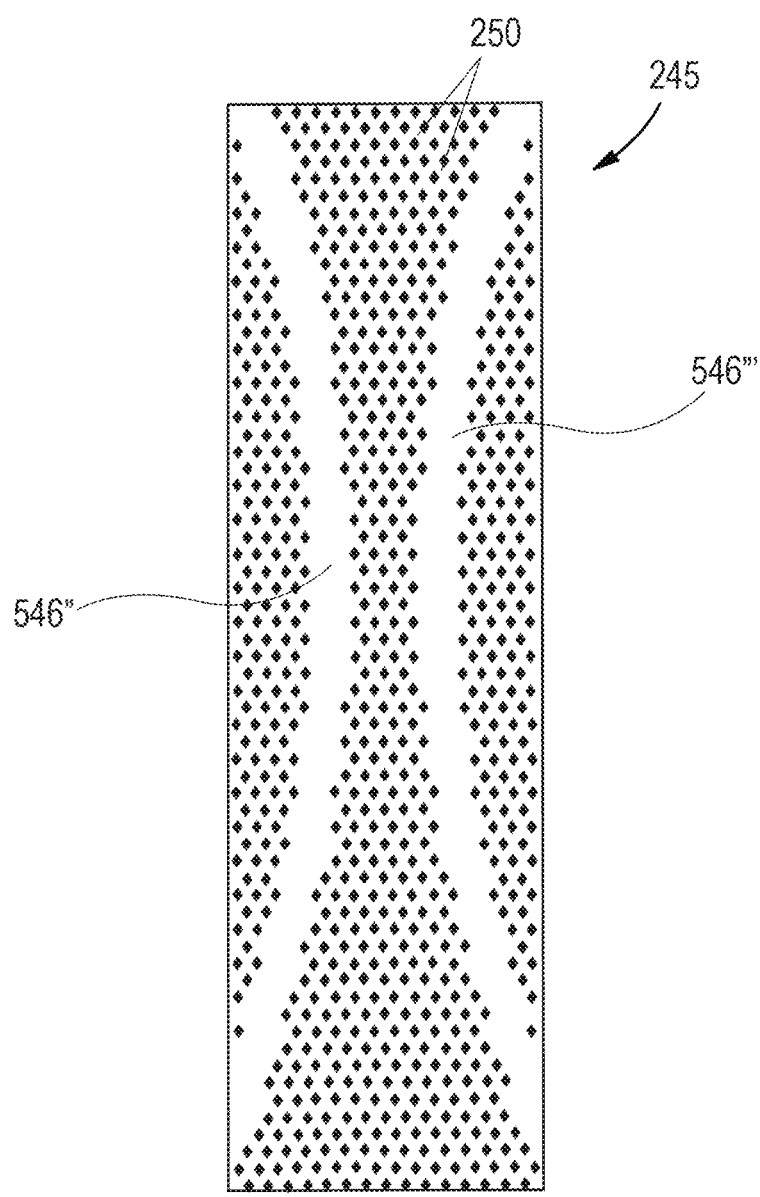
FIG. 49 is an example plan view of a portion of a wearer-facing surface of a nonwoven web of an absorbent article, wherein the nonwoven web comprises a design in accordance with the present disclosure.

FIG. 49 illustrates a schematic illustration of a three-dimensional material 245 with a wearer-facing surface towards the viewer. The three-dimensional material 245 comprises one or more designs 546" and 546''' formed in areas free of protrusions 250. In some instances, the designs 546" and 546''' may comprise an ink, adhesive, or other material that has a different color than a remaining portion of the topsheet 224 and/or a remaining portion of the acquisition layer 252. The protrusions 250 of the three-dimensional material 245 may be facing into the page, out of the page, or into or out of the page. If the designs 546" and 546''' comprise an ink, adhesive, or other material that has a different color than the remaining portion of the topsheet 224 and/or the remaining portion of the acquisition layer 252, the ink, adhesive, or other material may be applied to protrusions or non-protrusions areas, for example.

Figure 50:
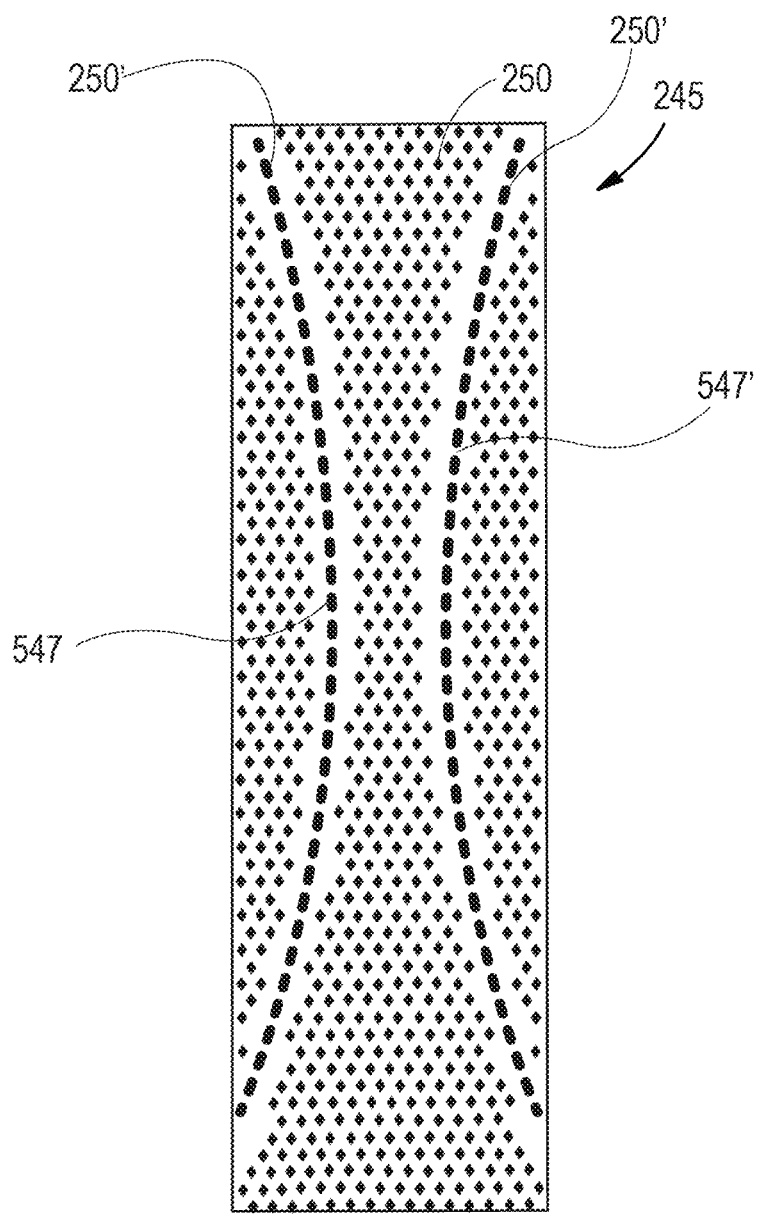
FIG. 50 is an example plan view of a portion of a wearer-facing surface of a nonwoven web of an absorbent article, wherein the nonwoven material comprises a design in accordance with the present disclosure.

FIG. 50 illustrates a schematic illustration of a three-dimensional material 245 with a wearer-facing surface towards the viewer. The three-dimensional material 245 may comprise one or more designs 547 and 547' that may be at least partially formed by a first pattern of protrusions 250'. Protrusions 250' may have the same or a different size, shape, and/or orientation compared to the other protrusions 250 in the three-dimensional material 245. The protrusions 250' may be smaller or larger than the protrusions 250. The protrusions 250' may be the same or different in one or more of the designs. The protrusions 250' may be continuous or discontinuous.

In a form, the designs 547 and 547' may comprise a first plurality of the protrusions 250' and a remaining portion of the three-dimensional nonwoven material 245 may comprise a second plurality of protrusions 250. The first plurality of the protrusions 250' may be the same as or different than the second plurality of the protrusions 250. The designs 547 and 547' may also comprise areas of the three-dimensional nonwoven material 245 that are free of any protrusions. The protrusions 250 and 250' may both be facing into the page, out of the page, or into and out of the page.

Figure 51:
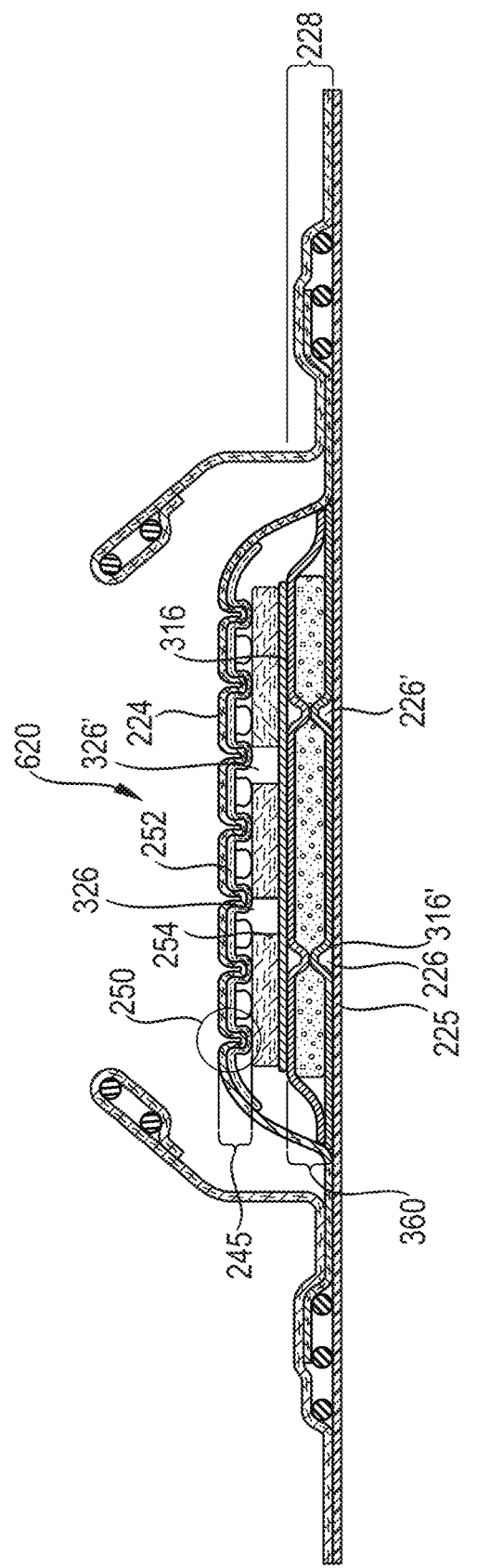
FIG. 51 is an example cross-sectional view of an absorbent article, with an absorbent core and two materials intermediate the absorbent core and a multilayer nonwoven web, wherein the absorbent core and one of the materials intermediate the absorbent core and the multilayer nonwoven web both have channels, and wherein the channels do not overlap each other in a Z-direction, in accordance with the present disclosure.

FIG. 51 is an example cross-sectional view of an absorbent article 620 have certain channel configurations that do not overlap in the Z-direction. The distribution material 254 may have one or more channels 326 and 326'. The absorbent core 228 may have one or more channels 226 and 226'. The channels 326 and 326' may be free of overlap in the Z-direction with the channels 226 and 226'.

Figure 52:
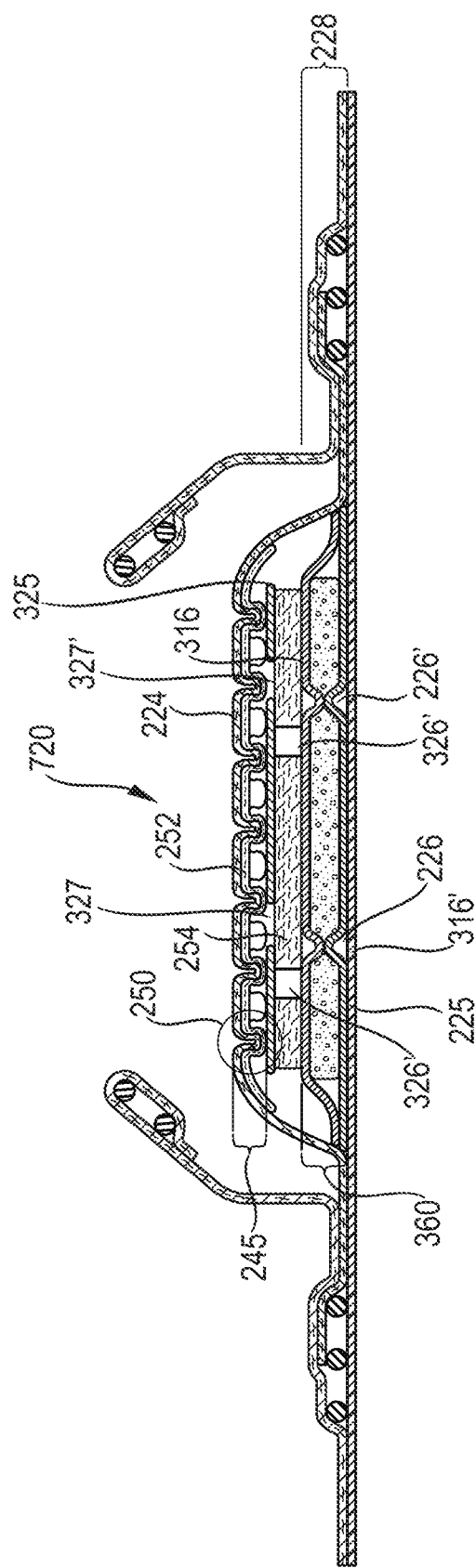
FIG. 52 is an example cross-sectional view of an absorbent article, with an absorbent core and two materials intermediate the absorbent core and a multilayer nonwoven web, wherein the absorbent core and both of the materials intermediate the absorbent core and the multilayer nonwoven web all have channels, and wherein the channels do not overlap each other in a Z-direction, in accordance with the present disclosure.

FIG. 52 is an example cross-sectional view of an absorbent article 720 have certain channel configurations that do not overlap in the Z-direction. The distribution material 254 may have one or more channels 326 and 326'. The absorbent core 228 may have one or more channels 226 and 226'. The carrier layer 325 may have one or more channels 327 and 327'. The channels 326 and 326' may be free of overlap in the Z-direction with the channels 226 and 226' and the channels 327 and 327'. In other instances, the channels may all at least partially overlap each other in the Z-direction, but not be completely overlapping in the Z-direction.

Indicia and/or Color

FIG. 52 will be referred to in this section to illustrate an example absorbent article configuration that may comprise indicia and/or color, although any of the example absorbent article configurations illustrated herein will also be within the scope of the present disclosure. For example, the carrier layer 325 may or may not be provided or the carrier layer 325 may be provided under the distribution material 254. In another example, the carrier layer 325 and the distribution material 254 may or may not be provided. In other instances, the topsheet 224 or the acquisition layer 254 may be generally flat or planer, as shown in previous figures. The carrier layer 325 may or may not have channels 327 and 327'. Also, the distribution material 254 may or may not have channels 326 and 326'. Further, the absorbent core 228 may or may not have channels 226 and 226'. All of the channels 327 and 327', 226 and 226', and 326 and 326', if provided, may at least partially overlap each other in the Z-direction, may not overlap each other in the Z-direction, and/or may fully overlap each other in the Z-direction. In some instances, a first set of channels (e.g. 226 and 226') may overlap a second set of channels (e.g., 326 and 326') in the Z-direction, while a third set of channels (e.g., 327 and 327') may not overlap with either of the first and second sets of channels, for example. The core bag 360 may be in the configuration shown in FIG. 52, in FIG. 48, or may be in any other suitable configuration.

The term "indicia", as used herein, may comprise one or more inks with pigments, adhesives with pigments, words, designs, trademarks, graphics, patterns, and/or pigmented areas, for example. Indicia is not merely a full colored or tinted layer, such as an acquisition layer, for example. The indicia may typically be a different color than: (1) the layer that it is printed on, positioned on, or applied to; or (2) a different color than other layers of an absorbent article. The phrase a "different color" means a different shade of the same color (e.g., dark blue and light blue) or may be completely different color (e.g., blue and gray). The indicia should be at least partially visible from either a wearer facing surface, a garment facing surface, or both of an absorbent article, although the indicia may not be printed on, positioned or, on applied to the wearer or garment facing surfaces of the absorbent articles. The indicia may be printed on, positioned on, or applied to protrusion areas and non-protrusion areas, protrusion areas only, or non-protrusion areas only, for example. The indicia may comprise a light activatable material, a liquid activatable material, a pH activatable material, a temperature activatable material, a menses activatable material, a urine activatable material, a BM activatable material, and/or an otherwise activatable material. These activatable materials may typically undergo a chemical reaction, or other reaction, to change the indicia from one color to a different color, from one color to a different shade of the same color, from a color that is not visually distinguishable or recognizable in an absorbent article to a color that is visually distinguishable or recognizable in an absorbent article, or from a color that is visually distinguishable or recognizable in an absorbent article to a color that is not visually distinguishable or recognizable in an absorbent article. In an instance, the indicia may grow or shrink or display a graphic/not display a graphic after the indicia undergoes the reaction. In other instances, the indicia may be activated by a stress or a strain during manufacture or wear. The indicia may be white or non-white. If the indicia is white in color, at least one layer may be non-white so that the indicia is visible from a wearer and/or garment facing surface of the absorbent articles, for example. The indicia may comprise embossments, fusion bonds, or other mechanical deformations. In other instances the indicia may at least partially overlap embossments, fusion bonds, or other mechanical deformations. In some instances, the indicia may be formed within either a sheath or a core of bicomponent fibers. For example, a core may be white, while a sheath may be blue, or vice versa.

The indicia may be on, positioned on, formed on, formed with, printed on, or applied to all of, or part of, a certain layer. The indicia may also be on, positioned on, formed on, formed with, printed on, or applied to one or more layers, or on all suitable layers of an absorbent article. The indicia may be on, positioned on, formed on, formed with, printed on, or applied to either side, or both sides, of the one or more layers of an absorbent article. In some instances, suitable layers for indicia placement comprise one or more of a topsheet, a secondary topsheet, an acquisition material, a distribution material, a carrier layer, a core bag, a wearer-facing side of the core bag, a garment-facing side of the core bag, and/or an additional layer positioned at least partially intermediate the topsheet and the wearer-facing side of the core bag (hereafter sometimes referred to as "suitable layers for indicia placement").

Either in addition to or separate from the indicia described above, any one or more of the suitable layers for indicia placement, or a portion thereof, may have a color different than any one or more of the remaining layers for indicia placement, or a portion thereof. The definition of the phrase "different color" above also applies to this part of the disclosure. In some instances, the indicia may be a different color than any one or more of the suitable layers for indicia placement. Alternatively, an indicia may be on one of the suitable layers for indicia placement while another one of the remaining suitable layers for indicia placement may be a different color than the indicia. One example may be a blue indicia on a white carrier layer with the acquisition layer or topsheet being teal. In another example, a blue indicia may be on a white carrier layer with the acquisition layer and topsheet also being white. As such, the blue indicia may be viewable from a wearer-facing surface. In another example, a blue indicia may be on an acquisition layer, wherein the topsheet and the acquisition layer are nested together in the protrusions 250. In an instance where the topsheet and the acquisition layer are nested together in the protrusions 250, the indicia may be applied to the acquisition layer or the topsheet before or after such nesting. In an example, two different indicia may be positioned on the same or different layers for indicia placement. The two different indicia may be different in color, pattern, and/or graphic, for example. If the two different indicia are on different layers for indicia placement, the two layers may be the same color or different colors, or have portions that are the same color or different colors.

In some instances, a visible color of a portion of, or all of, the interior (wearer-facing surface) of an absorbent article may be coordinated with and/or compliment a visible color of a portion of, or all of, the exterior (garment-facing surface) of the absorbent article, as described in further detail in U.S. Pat. No. 8,936,584. The indicia visible from the interior may also be coordinated with and/or compliment the indicia visible from the exterior of the absorbent article. In such an instance, the indicia visible from the exterior of the absorbent article may be on the outer cover nonwoven or the backsheet film. In still other instances, the visible indicia and/or color from the interior may also be coordinated with or compliment the indicia and/or color visible from the exterior of the absorbent article.

In addition to that described above, a first portion of one of the suitable layers for indicia placement may be a first color and a second portion of the same of the suitable layers for indicia placement may be a second color. The first and second colors may be a different color. In other instances, a first portion of one of the suitable layers for indicia placement may be a first color and a second portion of a different one of the suitable layers for indicia placement may be a second color. The first and second colors may be a different color.

In an instance, in an absorbent article, one of a topsheet, an acquisition material, a portion of a core bag, or an additional layer (e.g., a carrier layer) may be a different color than a different one of the topsheet, the acquisition material, the portion of the core bag, or the additional layer. In another instance, in an absorbent article one of a portion of a topsheet, a portion of an acquisition material, a portion of a core bag, or a portion of an additional layer may be a different color than a different one of the portion of the topsheet, the portion of the acquisition material, the portion of the core bag, or the portion of the additional layer. In another instance, in an absorbent article, a first portion of one of a topsheet, an acquisition material, a core bag, or an additional layer may be a different color as a second portion of the same one of the topsheet, the acquisition material, the core bag, or the additional layer.

Cellulose Fibers in Some Suitable Layers for Indicia Placement

Figure 53:
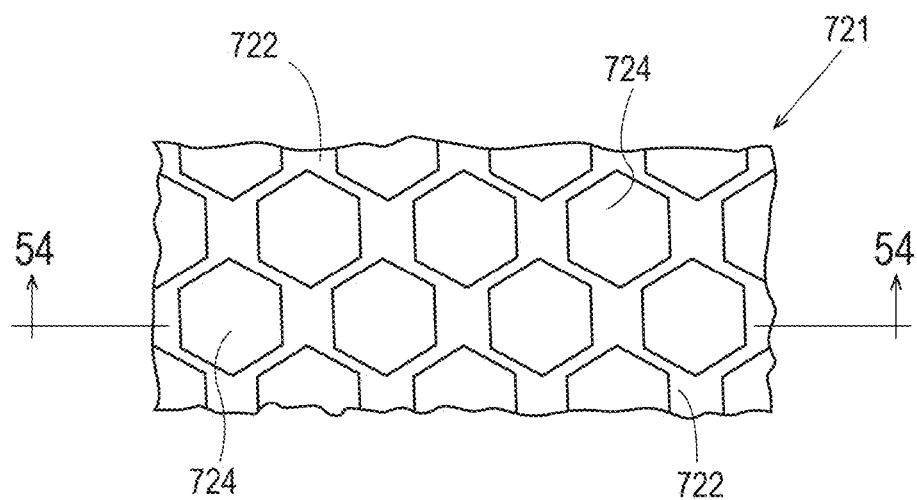
FIG. 53 is an example plan view of a cellulose based three-dimensional material for use as at least part of a carrier layer and/or a distribution material in accordance with the present disclosure.
Figure 54:
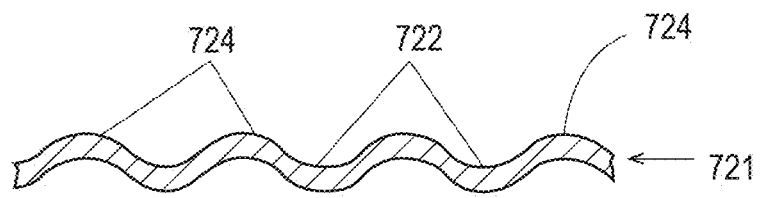
FIG. 54 is an example cross-sectional view of the cellulose based three-dimensional layer taken about line 54-54 of FIG. 53 in accordance with the present disclosure.
Figure 55:
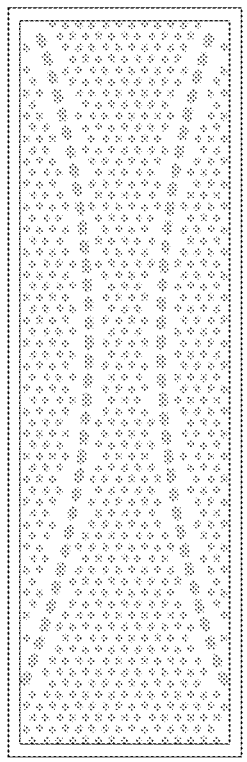
FIGS. 55, 58, 60, 63, 65, 68, 70, and 72 illustrate some example patterns of three-dimensional nonwoven webs in accordance with the present disclosure.

In certain instances, it may be desirable to use a carrier layer 325 or a distribution material 254 that comprises cellulose fibers or pulp. In some instances, the carrier layer 325 or the distribution material 254 may comprise at least 70%, at least 80%, at least 90%, at least 95% or more of cellulose fibers by weight of the respective layer or material. The carrier layer or the distribution material may comprise one or more layers comprising the cellulose fibers. The layers may be individual layers, or a single layer folded any suitable number of times over itself. The carrier layer comprising the cellulosic fibers may be generally planar or, in some instances, may be three-dimensional. The distribution material 254 may comprise one or more generally planar or three-dimensional layers comprising the cellulose fibers. These three-dimensional layers comprising the cellulose fibers may be wet formed using a papermaking process. Referring to FIGS. 53 and 54, an example three-dimensional material or layer is illustrated. FIG. 53 is a top view of the three-dimensional layer 721 and FIG. 54 is a cross-sectional view of the three-dimensional layer 721 taken about line 54-54 of FIG. 53. The three-dimensional layer 721 may comprise a continuous network region 722 and a plurality of discrete zones 724. The continuous network region 722 may comprise a first average density and the plurality of discrete zones 724 may each comprise a second average density. The plurality of discrete zones 724 may be dispersed throughout the continuous network region 722. The first and second average densities may be different. The three-dimensional layer or layers 721 may also comprise a wet strength resin.

The continuous network region 722 and the plurality of discrete zones 724 may have a common intensive property. The common intensive property of the continuous network region 722 may have a first value. The common intensive property of the plurality of discrete zones 724 may have a second value. The first value may be different than the second value. The common intensive property may be basis weight, caliper, opacity, average density, or elevation, for example. Such three-dimensional materials are described in greater details, in the context of a distribution material, in U.S. patent application Ser. No. 14/543,967 (P&G Case No. 13605Q), Ser. No. 14/543,973(P&G Case No. 13606Q) and Ser. No. 14/543,984 (P&G Case No. 13607Q), all filed on Nov. 18, 2014, but could also be used in the context of a carrier layer. These layers comprising cellulose fibers, whether three-dimensional or not, may be colored or may comprise indicia as described herein.

Bonding and Colored Layers

In some instances, it may be desirable to have a layer, such as a carrier layer 325, for example, under an acquisition layer/topsheet laminate (as described herein), where the carrier layer 325 has a different color than the acquisition layer/topsheet laminate. For instance, the laminate may be white and the carrier layer may be blue. In such an instance, when the acquisition layer/topsheet laminate are combined (as described herein) different opacity and density zones are present within the laminate. As such, the color of the carrier layer may be either more visible or less visible from a wearer-facing surface in the various zones of the laminate owing to the laminate having zones of high and low density and high and low opacity. In an instance where a bonded or apertured layer having a first color is positioned over a layer having second different color, the second different color of the layer may be more or less visible in the bonds or apertures compared to the remainder of the layer. In other instances, the laminate and the carrier layer may be different tones of the same color to enhance the depth layering perception when viewing a wearer-facing surface of an absorbent article. If a single three-dimensional nonwoven material is used as a topsheet or an acquisition material, the same as described above with respect to different color layers may also be true.

Indicia

Figure 56:
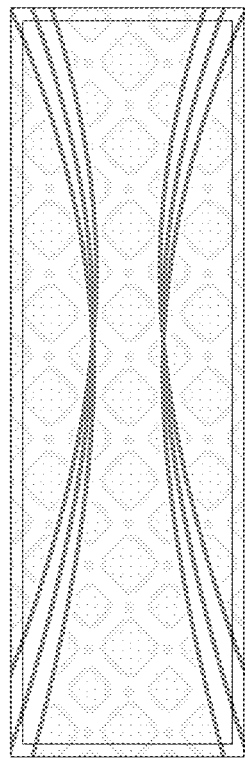
FIGS. 56, 59, 61, 64, 66, 69, 71, and 73 illustrate some example indicia that may underlie any of the example three-dimensional nonwoven webs having patterns of FIGS. 55, 58, 60, 63, 65, 68, 70, and 72 in accordance with the present disclosure.
Figure 57:
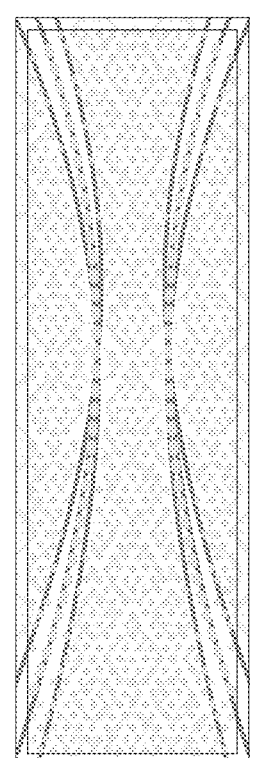
FIG. 57 illustrates the overlap of the pattern of the three-dimensional web of FIG. 55 with the indicia of FIG. 56 in accordance with the present disclosure.
Figure 58:
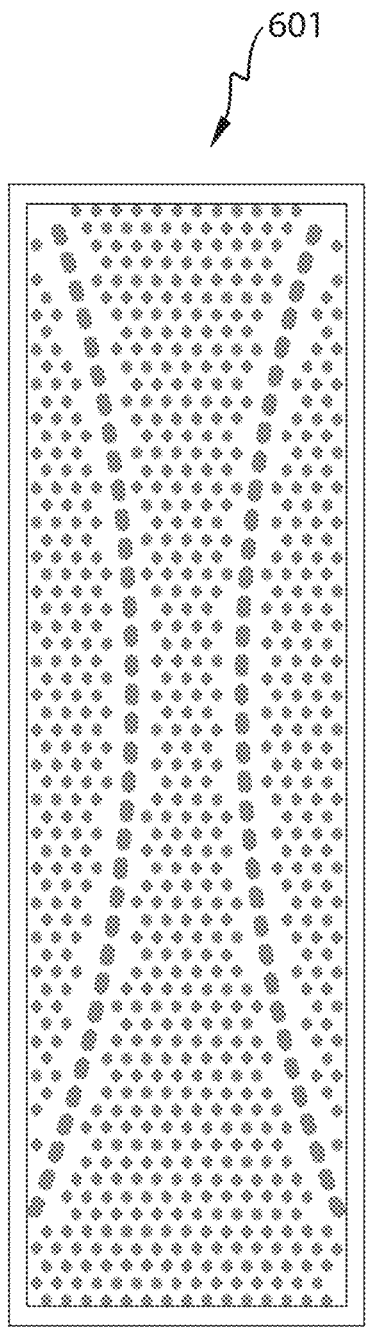
Figure 59:
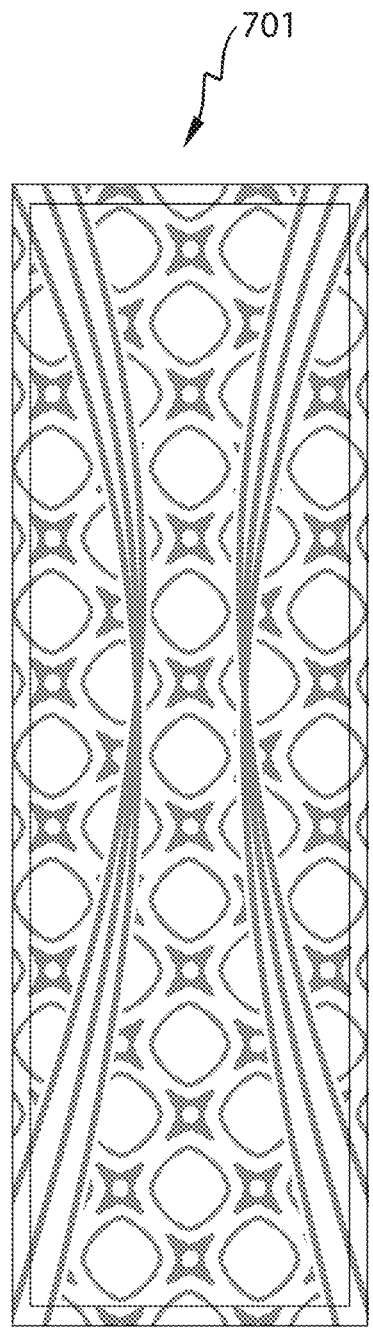
Figure 60:
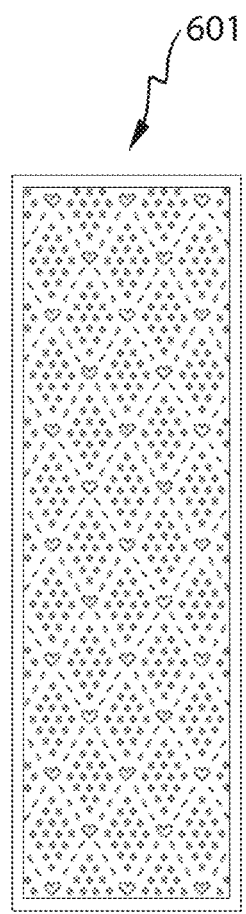
Figure 61:
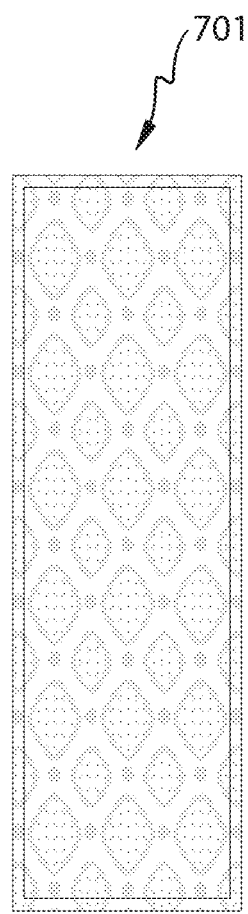
Figure 62:
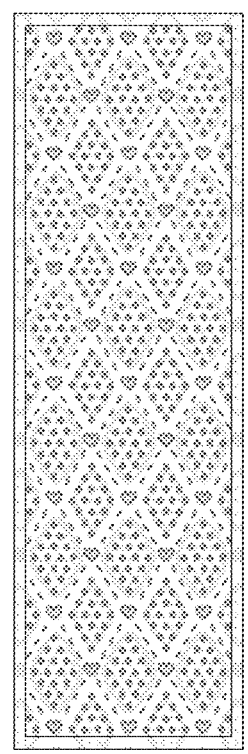
FIG. 62 illustrates the overlap of the pattern of the three-dimensional web of FIG. 60 with the indicia of FIG. 61 in accordance with the present disclosure.
Figures 63, 64:
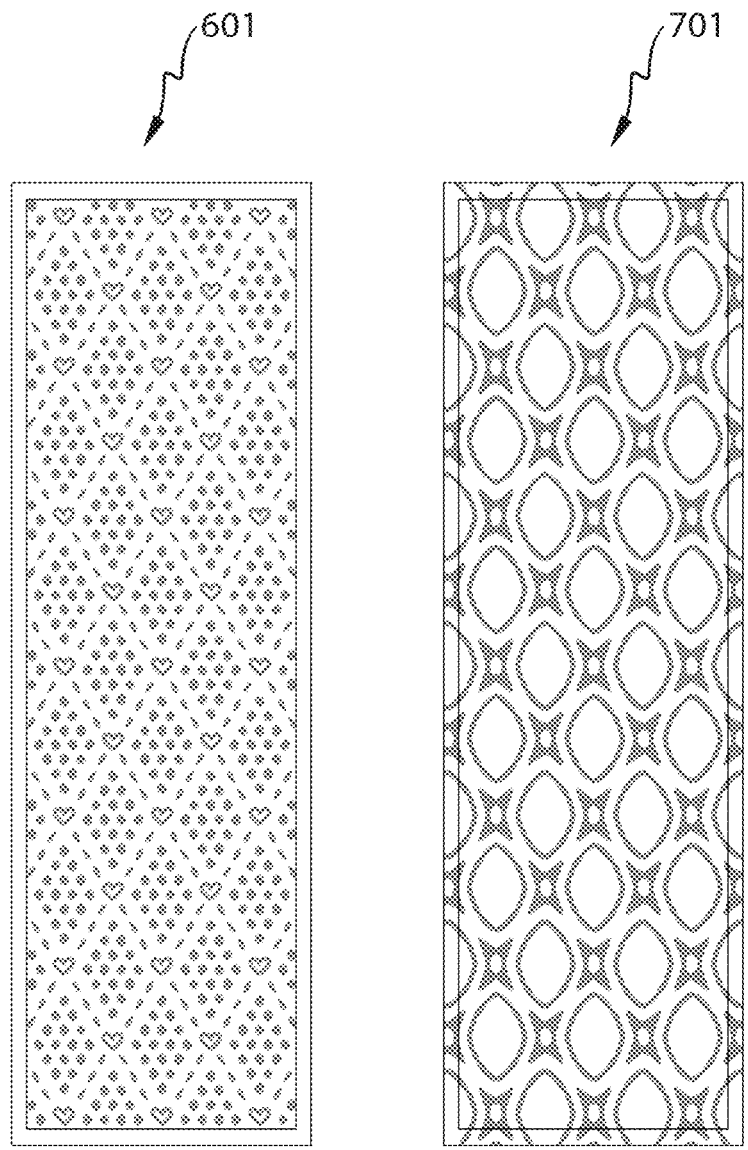
Figures 65, 66, 67:
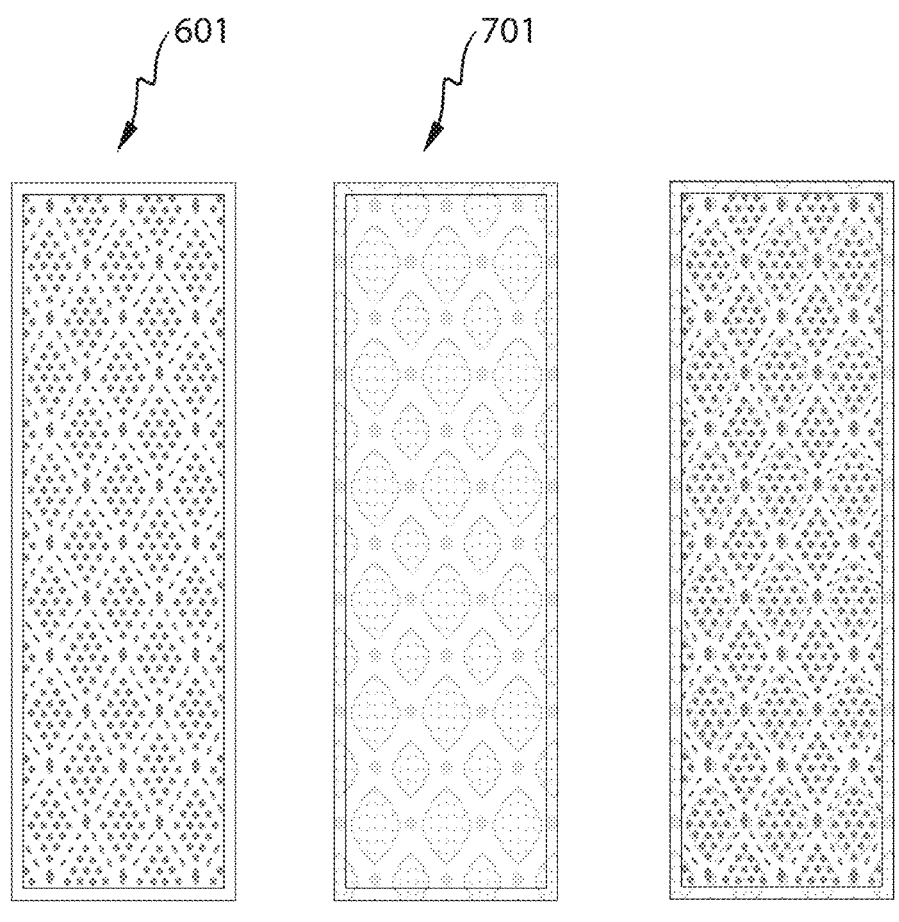
FIG. 67 illustrates the overlap of the pattern of the three-dimensional web of FIG. 65 with the indicia of FIG. 66 in accordance with the present disclosure.
Figure 68:
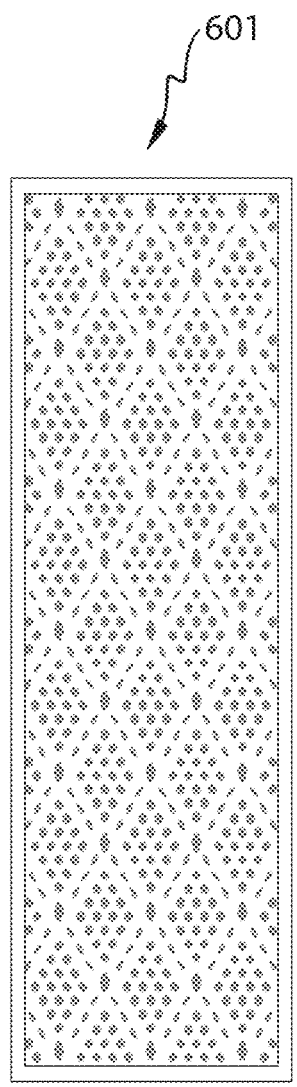
Figure 69:
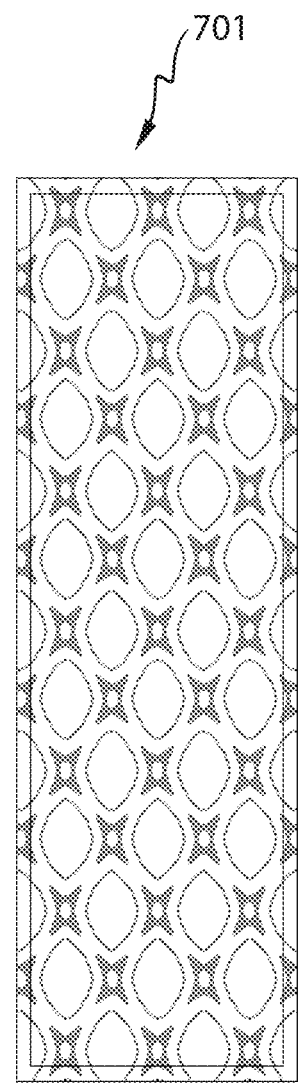
Figure 70:
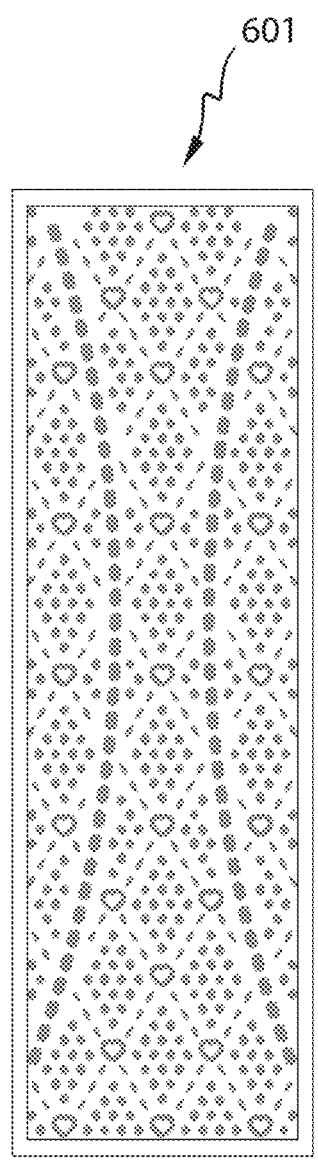
Figure 71:
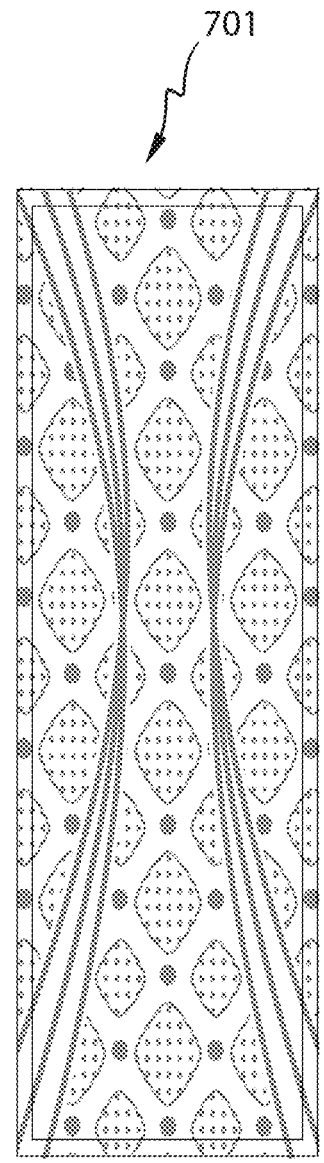
Figure 72:
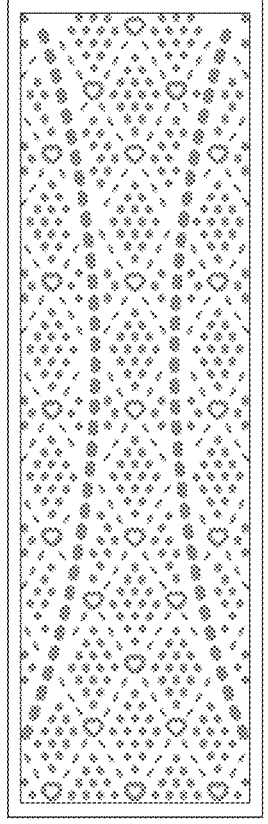
Figure 73:
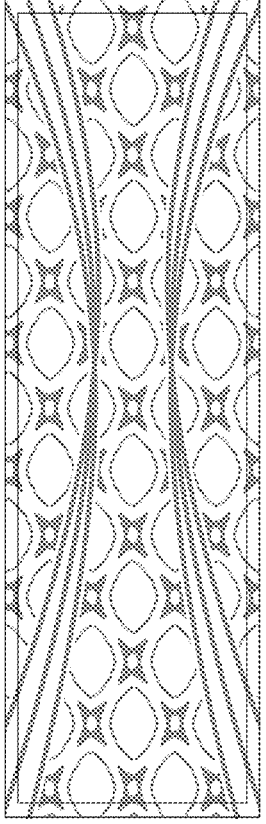

The three-dimensional nonwoven materials of the present disclosure may have a plurality of different patterns. At least portions of these patterns represent protrusions (e.g., like protrusions 250 described herein) and other portions may represent embossed areas or printed areas. Some example patterns 601 are shown in FIGS. 55, 58, 60, 63, 65, 68, 70, and 72. These figures may represent patterns in a topsheet, an acquisition layer, or a topsheet/acquisition layer laminate. These patterns 601 of the three-dimensional nonwoven materials may be combined with an underlying layer comprising indicia, such as a pigmented adhesive or ink, for example. Some example indicia patterns 701 are illustrated in FIGS. 56, 59, 61, 64, 66, 69, 71, and 73. These figures may represent an acquisition layer, a carrier layer, or another layer intermediate a topsheet and an absorbent core. The patterns of FIGS. 55, 58, 60, 63, 65, 68, 70, and 72 may be overlapped with, or at least partially overlapped with, in a Z-direction, any of the indicia patterns 701 of FIGS. 56, 59, 61, 64, 66, 69, 71, and 73. An example of the overlapping of the pattern 601 of FIG. 55 and the indicia pattern 701 of FIG. 56 is illustrated in FIG. 57. An example of the overlapping of the pattern 601 of FIG. 60 and the indicia pattern 701 of FIG. 61 is illustrated in FIG. 62. An example of the overlapping of the pattern 601 of FIG. 65 and the indicia pattern 701 of FIG. 66 is illustrated in FIG. 67. Any of the patterns 601 and indicia patterns 701 of FIGS. 58 and 59, FIGS. 63 and 64, FIGS. 68 and 69, FIGS. 70 and 71, and FIGS. 72 and 73 may be overlapped in the same or a similar fashion. Any of the patterns 601 of FIGS. 55, 58, 60, 63, 65, 68, 70, and 72 may also be overlapped with any of the indicia patterns 701 of FIGS. 56, 59, 61, 64, 66, 69, 71, and 73.

As can be seen in FIGS. 57, 62, and 67, the overlapped patterns 601 and indicia patterns 701 creates an aesthetically pleasing portion of an absorbent article structure that provides (1) a three dimensional topsheet, a three-dimensional acquisition layer, or a three-dimensional topsheet/acquisition layer laminate; (2) an impression of depth; (3) an impression of softness or softness; (4) an impression of absorbency or absorbency; (5) an impression that bodily exudates will be locked away; and (6) an impression that bodily exudates will not remain in contact with the skin. All of these factors are consumer preferred.

In addition to the patterns and indicia patterns illustrated in FIGS. 55-73, any of the layers of an absorbent article, or portions thereof, may have a different color than another layer of the absorbent article to further enhance the aesthetically pleasing look of absorbent articles.

The scale of the indicia patterns 701 may be larger than, smaller than, or the same as, the scale of the patterns 601 depending on the desired appearance of the overlapped pattern 601 and indicia pattern 701.

Sanitary Napkin

The three-dimensional nonwoven materials of the present disclosure may form a portion of a sanitary napkin, for instance, a portion of, or all of, a topsheet, a portion of, or all of, an acquisition layer (or secondary topsheet), or portion of, or all of, a topsheet and acquisition layer (or secondary topsheet) nested together. In other instances, the three-dimensional nonwoven materials may form a strip or patch placed on the topsheet of the sanitary napkin.

Figure 74:
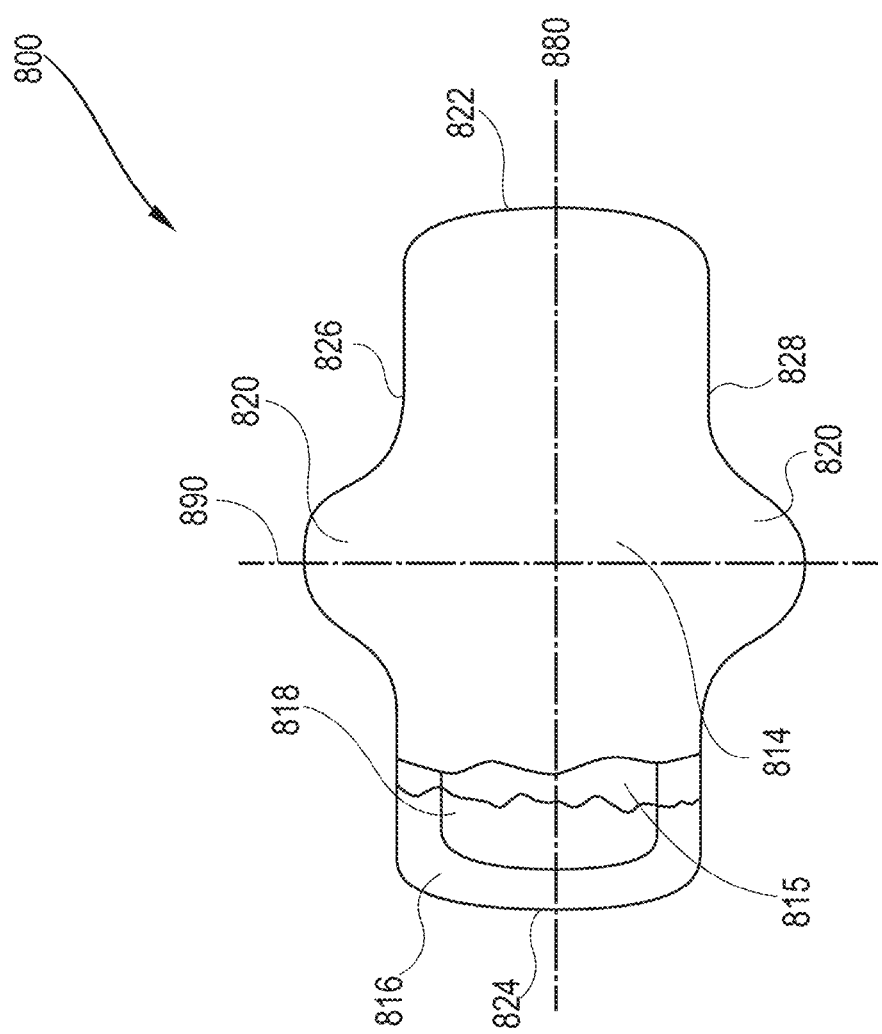
FIG. 74 is a plan view of another example absorbent article, wearer-facing surface facing the viewer, that is a sanitary napkin with some of the layers cut away in accordance with the present disclosure, the nonwoven webs of the present disclosure may be present on this example absorbent article structure.

An example sanitary napkin 800 is disclosed in FIG. 74. The sanitary napkin 800 may comprise a liquid permeable topsheet 814, a liquid impermeable, or substantially liquid impermeable, backsheet 816, and an absorbent core 818. The absorbent core 818 may have any or all of the features described herein with respect to the absorbent cores 228, including one or more channels. The acquisition layer 815 may have any or all of the features described herein with respect to the acquisition layers 252, including one more channels. A carrier layer (like carrier layer 325 herein) and a distribution material (like distribution material 254 herein) may also be optionally provided, including one or more channels in each layer. The sanitary napkin 800 may also comprise wings 820 extending outwardly with respect to a longitudinal axis 880 of the sanitary napkin 800. The sanitary napkin 800 may also comprise a lateral axis 890. The wings 820 may be joined to the topsheet 814, the backsheet 816, and/or the absorbent core 818. The sanitary napkin 800 may also comprise a front edge 822, a rear edge 824 longitudinally opposing the front edge 822, a first side edge 826, and a second side edge 828 longitudinally opposing the first side edge 826. The longitudinal axis 880 may extend from a midpoint of the front edge 822 to a midpoint of the rear edge 824. The lateral axis 890 may extend from a midpoint of the first side edge 826 to a midpoint of the second side edge 828. The sanitary napkin 800 may also be provided with additional features commonly found in sanitary napkins as is generally known in the art.

Spunbond Webs

In the case of spunbond webs, the webs may have a thermal point bond pattern that is not highly visible to the naked eye. For example, dense thermal point bond patterns that are equally and uniformly spaced are typically not highly visible to the naked eye. After the webs are processed through the mating male and female rolls, the thermal point bond patterns may still not be highly visible to the naked eye. Alternatively, the webs may have a thermal point bond pattern that is highly visible to the naked eye. For example, thermal point bonds that are arranged into a macro-pattern, such as a diamond pattern, for example, may be highly visible to the naked eye. After the webs are processed through the mating male and female rolls, the thermal point bond pattern is still highly visible to the naked eye and may provide a secondary visible texture element to the webs.

Fiber Concentration

In an instance, the topsheet may comprise a generally planar first region of the topsheet. The acquisition material may comprise a generally planar first region of the acquisition material. The three-dimensional protrusions of the respective topsheet and the acquisition material may comprise a plurality of discrete integral second regions. The term "generally planar" is not meant to imply any particular flatness, smoothness, or dimensionality. Thus, the first region of the topsheet may comprise other features that provide the first region of the topsheet with a topography. The first region of the acquisition material may comprise other features that provide the first region of the acquisition material with a topography. Such other features may comprise, but are not limited to small protrusions, raised network regions around the base forming an opening, and other types of features. Thus, the first region of the topsheet and/or the first region of the acquisition material may be generally planar when considered relative to the respective second regions. The first region of the topsheet and/or the first region of the acquisition material may comprise any suitable plan view configuration. In some instances, the first region of the topsheet and/or the first region of the acquisition material may be in the form of a continuous inter-connected network which comprises portions that surround each of, or some of, the three-dimensional protrusions.

The side walls and the area around the base of the majority of the three-dimensional protrusions may have a visibly significantly lower concentration of fibers per given area (which may be evidence of a lower basis weight or lower opacity) than the portions of the topsheet and/or the acquisition material in the unformed first region of the respective topsheet and the acquisition material. The majority of the three-dimensional protrusions may also have thinned fibers in the side walls. Thus, the fibers may have a first cross-sectional area when they are in the undeformed topsheet and the acquisition material, and a second cross-sectional area in the side walls of the majority of the three-dimensional protrusions of the topsheet/acquisition material laminate, wherein the first cross-sectional area is greater than the second cross-sectional area. The side walls may also comprise some broken fibers. In some examples, the side walls may comprise greater than or equal to about 10%, about 20%, about 30%, alternatively greater than or equal to about 50%, broken fibers.

As used herein, the term "fiber concentration" has a similar meaning as basis weight, but fiber concentration refers to the number of fibers/given area, rather than g/area as in basis weight.

The topsheet/acquisition material laminate may comprise the majority of the three-dimensional protrusions which are oriented with the base facing upward in which the concentration of fibers at the distal end of each respective topsheet and the acquisition material differs between the topsheet and the acquisition material.

The concentration of fibers in the first region of the acquisition material and in the distal ends of the majority of the three-dimensional protrusions may be greater than the concentration of fibers in the side walls of the majority of the three-dimensional protrusions in the acquisition material.

The concentration of fibers in the first region of the topsheet and in the distal ends of the majority of the three dimensional protrusions may be greater than the concentration of fibers in the side walls of the majority of the three dimensional protrusions in the topsheet.

Alternatively, the concentration of fibers in the first region of the acquisition material may be greater than the concentration of fibers in the side walls of the majority of the three-dimensional protrusions in the acquisition material, and the concentration of fibers in the side walls of the majority of the three-dimensional protrusions in the acquisition material may be greater than the concentration of fibers forming the distal ends of the majority of the three-dimensional protrusions in the acquisition material.

The concentration of fibers in the first region of the acquisition material may be greater than the concentration of fibers in the distal ends of the majority of the three-dimensional protrusions in the acquisition material, and the concentration of fibers in the first region of the topsheet and the distal ends of the majority of the three dimensional protrusions may be greater than the concentration of fibers in the side walls of the majority of the three-dimensional protrusions in the topsheet.

A portion of the fibers that form the first region fibers in the acquisition material and/or the topsheet may comprise thermal point bonds, and the portion of the fibers in the acquisition material and/or the topsheet forming the side walls and distal ends of the majority of the three-dimensional protrusions may be substantially free of thermal point bonds. In at least some of the three-dimensional protrusions, at least some of the fibers in the acquisition material and/or the topsheet may form a nest or circle around the perimeter of the three-dimensional protrusion at the transition between the side wall and the base of the three-dimensional protrusion.

In some instances, the topsheet or the acquisition material may have a plurality of bonds (such as thermal point bonds) therein to hold the fibers together. Any such bonds are typically present in the precursor materials or webs from which the respective topsheet or the acquisition material are formed.

Forming three-dimensional protrusions in the topsheet/acquisition material laminate may also affect the bonds (thermal point bonds) within the topsheet and/or the acquisition material.

The bonds within the distal end of the three-dimensional protrusions may remain intact (not be disrupted) by the mechanical deformation process that formed the three-dimensional protrusions. In the side walls of the three-dimensional protrusions, however, the bonds originally present in the precursor topsheet web and/or the precursor acquisition material web may be disrupted. When it is said that the bonds may be disrupted, this can take several forms. The bonds can be broken and leave remnants of a bond. In other instances, such as where the precursor materials of the respective topsheet web or the acquisition material web is underbonded, the fibers can disentangle from a lightly formed bond site (similar to untying a bow), and the bond site may essentially disappear. In some instances, after the mechanical deformation process, the side walls of the majority of the three-dimensional protrusions may be substantially free (or completely free) of thermal point bonds.

The bonds within the first region of the topsheet and the distal end of the three-dimensional protrusions may remain intact. In the side walls of the three-dimensional protrusions, however, the bonds originally present in the precursor topsheet web may be disrupted such that the side walls are substantially free of thermal point bonds. Such a topsheet could be combined with an acquisition material in which the concentration of fibers within the topsheet in the first region and the distal end of the three-dimensional protrusions is also greater than the concentration of fibers in the side walls of the three-dimensional protrusions.

The acquisition material may have thermal point bonds within the first region of the acquisition material and the distal end of the three-dimensional protrusions that remain intact. In the side walls of the three-dimensional protrusions, however, the bonds originally present in the precursor acquisition material web comprising the acquisition material may be disrupted such that the side walls of the acquisition layer are substantially free of thermal point bonds.

Packages

The absorbent articles of the present disclosure comprising the three-dimensional nonwoven material and certain channels configurations may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 100 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 75:
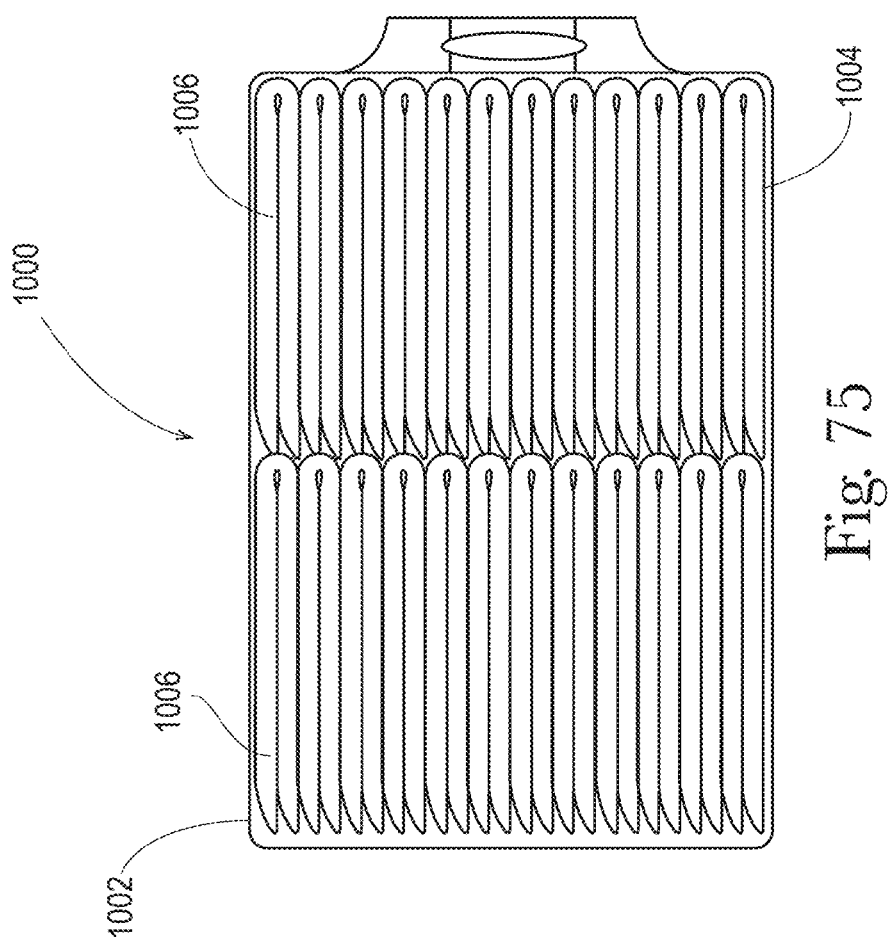
FIG. 75 is a side view of a package of absorbent articles showing the package width in accordance with the present disclosure, with the outer surface illustrated as transparent for purposes of clarity.

FIG. 75 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

EXAMPLES

Comparative Example 1

In Comparative Example 1, the material is a composite of two materials glued together using H.B. Fuller of St. Paul, Minn. U.S.A. D3166ZP hot melt adhesive applied in a spiral pattern at a 1 gsm add on level. The composite material is processed through a nip formed by one of The Procter & Gamble Company's SELF rolls and a ring roll as described in U.S. Pat. No. 7,410,683 B2, Curro, et al., at 25 feet/minute (fpm) (7.6 meters per minute) and 0.135″ (3.43 mm) DOE. The material layer in contact with the SELF roll is a 20 gsm spunbond nonwoven produced by Fitesa of Simpsonville, S.C., U.S.A. Such a material is described in Fitesa's U.S. patent application Ser. No. 14/206,699 entitled "Extensible Nonwoven Fabric" and is comprised of 2.5 denier fibers comprising a blend of PP and PE fibers. The material layer in contact with the ring roll is a 43 gsm spunbond nonwoven produced by Reicofil of Troisdorf, Germany, comprised of 7 denier co-PET/PET tipped-trilobal bicomponent fibers.

Example 1

Single Layer

In Example 1, the material is a 50 grams/m$^2$ (gsm) PE/PP sheath/core bicomponent spunbond nonwoven from Fitesa. It is processed at 25 fpm (7.6 meters per minute) speed at 0.155 inch (3.94 mm) depth of engagement (DOE) through male/female tooling (forming members). The teeth on the male tool have a rounded diamond shape like that shown in FIG. 21, with vertical sidewalls and a radiused or rounded edge at the transition between the top and the sidewalls of the tooth. The teeth are 0.186 inch (4.72 mm) long and 0.125 inch (3.18 mm) wide with a CD spacing of 0.150 inch (3.81 mm) and an MD spacing of 0.346 inch (8.79 mm). The recesses in the mating female roll also have a rounded diamond shape, similar to that of the male roll, with a clearance between the rolls of 0.032-0.063 inch (0.813-1.6 mm), varying slightly around the perimeter of the recess.

Example 2

Two Layers

In Example 2, the material is a composite of two materials glued together using the same hot melt adhesive applied in a spiral pattern as described in Comparative Example 1. It is processed through the male/female tooling described in Example 1, at 800 feet per minute (fpm) (24.4 meters per minute) and 0.155 inch (3.94 mm) DOE. The material layer in contact with the male roll is the 20 gsm spunbond nonwoven produced by Fitesa comprised of 2.5 denier fibers with a blend of PP and PE described in Comparative Example 1. The material layer in contact with the female roll is a 60 gsm through-air bonded carded nonwoven produced by Beijing Dayuan Non-Woven Fabric Co, LTD of Beijing, China, comprised of 5 denier PE/PET sheath/core bicomponent fibers.

Example 3

Two Layers

In Example 3, the material is a composite of two materials glued together using the same hot melt adhesive applied in a spiral pattern as described in Comparative Example 1. It is processed through the male/female tooling described in Example 1, at 800 fpm and 0.155 inch (3.94 mm) DOE. The material layer in contact with the male roll is a 20 gsm spunbond nonwoven produced by Fitesa comprised of 2.5 denier fibers with a blend of PP and PE described in Example 2. The material layer in contact with the female roll is an 86 gsm spunbond nonwoven produced by Reicofil comprised of 7 denier co-PET/PET tipped-trilobal bicomponent fibers.

The samples are compressed according to the Accelerated Compression Method, with a 7 kPa weight). The pre-compression caliper and the post-compression caliper of the samples are measured following the Accelerated Compression Method. The dimensions of the protrusions and openings are measured using a microscope at 20× magnification. The exterior dimensions of the cap are measured from a perspective view with the protrusions facing up, like that shown in FIG. 5. The protrusion depth and the interior cap width is measured from the cross-section of the material like that shown in FIG. 11.

the deformed samples. The samples should be oriented so the edges of each of the specimens and each of the paper towels are relatively aligned, and the protrusions in the specimens are all oriented the same direction.

4. Place the stack of samples into a 40° C. oven and place a weight on top of the stack. The weight must be larger than the foot of the thickness tester. To simulate high pressures or low in-bag stack heights, apply 35 kPa (e.g. 17.5 kg weight over a 70×70 mm area). To simulate low pressures or high in-bag stack heights, apply 7 kPa (e.g. 3.5 kg weight over a 70×70 mm area).
5. Leave the samples in the oven for 15 hours. After the time period has elapsed, remove the weight from the samples and remove the samples from the oven.
6. Within 30 minutes of removing the samples from the oven, measure the post-compression caliper as directed in step 2 above, making sure to maintain the same order in which the pre-compression caliper was recorded. Record the post-compression caliper of each of the 10 specimens to the nearest 0.01 mm.
7. Let the samples rest at 23±2° C. and at 50±2% relative humidity for 24 hours without any weight on them.
8. After 24 hours, measure the post-recovery caliper of each of the 10 specimens as directed in step 2 above, making sure to maintain the same order in which the pre-compression and post-compression calipers were recorded. Record the post-recovery caliper of each of

| Example | First Layer (Contacts Male Tool) | Second Layer (Contacts Female Tool) | Measured Before or After Compression | Caliper at 2.1 kPa (7 kPa) (mm) | Protrusion Depth (mm) | Base Opening Width ($W_0$) (mm) | Base Opening Length (mm) | Cap Width-Interior ($W_I$) (mm) | Cap Width-Exterior (mm) | Cap Length-Exterior (mm) | Ratio of Cap width-Interior to Base Opening Width |
|---|---|---|---|---|---|---|---|---|---|---|---|
| Comp. Ex. 1 | 20 gsm Spunbond PE/PP Blend | 43 gsm co-PET/PET Spunbond | Before Compression | 1.2 | 1.1 (Tuft) | 0.5 | 4.7 | <0.1* (Tuft) | 1.5 (Tuft) | 4.6 (Tuft) | — |
|  |  |  | After Compression | 0.7 | 0.3 | 0* (opening was closed) | 4.7 | 0* (opening was closed) | 0.7 | 4.0 | — |
| Ex. 1 | 50 gsm PE/PP Bico Spunbond | None | Before Compression | 0.48 | 1.3 | 1.5 | 3.3 | 1.7 | 2.4 | 4.2 | 1.1 |
|  |  |  | After Compression | 0.39 | 0.4 | 1.7 | 3.0 | 2.1 | 2.9 | 4.3 | 1.2 |
| Ex. 2 | 20 gsm Spunbond PE/PP Blend | 60 gsm PET Carded Through-air Bonded | Before Compression | 1.6 | 1.9 | 1.9 | 3.5 | 2.4 | 3.2 | 4.5 | 1.3 |
|  |  |  | After Compression | 0.88 | 0.5 | 1.6 | 3.3 | 1.8 | 2.7 | 4.4 | 1.1 |
| Ex. 3 | 20 gsm Spunbond PE/PP Blend | 86 gsm co-PET/PET Spunbond | Before Compression | 2.0 | 1.9 | 1.8 | 3.8 | 2.2 | 3.8 | 4.8 | 1.2 |
|  |  |  | After Compression | 1.3 | 0.7 | 1.5 | 3.6 | 2.5 | 3.7 | 5.2 | 1.7 |

*Difficult to measure because measurement was so small

Test Methods:

A. Accelerated Compression Method
1. Cut 10 samples of the specimen to be tested and 11 pieces of a paper towel into a 3 inch×3 inch (7.6 cm×7.6 cm) square.
2. Measure the caliper of each of the 10 specimens at 2.1 kPa and a dwell time of 2 seconds using a Thwing-Albert ProGage Thickness Tester or equivalent with a 50-60 millimeter diameter circular foot. Record the pre-compression caliper to the nearest 0.01 mm.
3. Alternate the layers of the specimens to be tested with the pieces of paper towel, starting and ending with the paper towels. The choice of paper towel does not matter and is present to prevent "nesting" of the protrusions in the 10 specimens to the nearest 0.01 mm. Calculate the amount of caliper recovery by subtracting the post-compression caliper from the post-recovery caliper and record to the nearest 0.01 mm.
9. If desired, an average of the 10 specimens can be calculated for the pre-compression, post-compression and post-recovery calipers.

B. Tensile Method

The MD and CD tensile properties are measured using method WSP 110.4 (05) Option B, with a 50 mm sample width, 60 mm gauge length, and 60 mm/min rate of extension. Note that the gauge length, rate of extension and resultant strain rate are different from that specified within the method.

C. In-Bag Stack Height Test

The in-bag stack height of a package of the absorbent articles of the present disclosure is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 75). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "90°" is intended to mean "about 90°".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a liquid permeable topsheet;
   an absorbent core;
   an acquisition material positioned between the topsheet and the absorbent core;
   wherein the liquid permeable topsheet and the acquisition material form a three-dimensional material comprising:
   a first surface facing the topsheet;
   a second surface facing the absorbent core;
   a generally planar first region; and
   a plurality of discrete integral second regions that comprise deformations forming protrusions comprising fibers extending outwardly in a Z-direction and toward the absorbent core from the second surface of the three-dimensional material and openings in the first surface of the three-dimensional material, wherein at least some protrusions each comprise:
   a base proximate to the second surface;
   a distal end extending outwardly in the Z-direction from the base;
   side walls between the base and the distal end of the protrusion; and
   a cap comprising at least a portion of the side walls and the distal end of the protrusion said fibers surrounding the side walls and cap of the protrusions, wherein the side walls have interior surfaces, wherein the interior surfaces of the side walls define one of said openings in the first surface, wherein the cap has a portion with a maximum interior width, wherein the base opening has a width measured in the same direction as the maximum interior width, and wherein the maximum interior width of the cap of the protrusion is greater than the width of the base opening;
   a liquid impermeable backsheet;
   wherein said absorbent core is positioned at least partially intermediate the three-dimensional material and the liquid impermeable backsheet, wherein the absorbent core comprises an absorbent material at least partially surrounded by a core bag;
   wherein each of the topsheet and the acquisition material comprises a nonwoven material; and
   wherein any of the topsheet, core bag and the acquisition material comprises indicia that are visible when viewing a wearer-facing surface of the absorbent article.

2. The absorbent article of claim 1, wherein the absorbent core comprises at least one channel disposed within the absorbent core that is substantially free of absorbent material.

* * * * *